US012813155B2

(12) United States Patent
Cui et al.

(10) Patent No.: US 12,813,155 B2
(45) Date of Patent: *Nov. 24, 2026

(54) ORGANIC ELECTROLUMINESCENT MATERIAL AND DEVICE THEREOF

(71) Applicant: BEIJING SUMMER SPROUT TECHNOLOGY CO., LTD., Beijing (CN)

(72) Inventors: Zhihao Cui, Beijing (CN); Renjie Zheng, Beijing (CN); Juntao Hu, Beijing (CN); Hualong Ding, Beijing (CN); Chi Yuen Raymond Kwong, Beijing (CN); Chuanjun Xia, Beijing (CN)

(73) Assignee: Beijing Summer Sprout Technology Co., Ltd., Beijing (CN)

( * ) Notice: Subject to any disclaimer, the term of this patent is extended or adjusted under 35 U.S.C. 154(b) by 1065 days.

This patent is subject to a terminal disclaimer.

(21) Appl. No.: 17/973,703

(22) Filed: Oct. 26, 2022

(65) Prior Publication Data

US 2023/0137110 A1 May 4, 2023

(30) Foreign Application Priority Data

Oct. 29, 2021 (CN) ......................... 202111252563.6

(51) Int. Cl.

*H10K 85/60* (2023.01)
*C07D 263/56* (2006.01)

(Continued)

(52) U.S. Cl.

CPC ......... *H10K 85/657* (2023.02); *C07D 263/56* (2013.01); *H10K 50/15* (2023.02); *H10K 50/155* (2023.02); *H10K 50/17* (2023.02)

(58) Field of Classification Search

CPC .... H10K 85/657; H10K 50/15; H10K 50/155; H10K 50/17; H10K 30/30; H10K 50/11;

(Continued)

(56) References Cited

U.S. PATENT DOCUMENTS 5,703,436 A 12/1997 Forrest et al.
5,707,745 A 1/1998 Forrest et al.

(Continued)

FOREIGN PATENT DOCUMENTS

CN 87101634 A 9/1987
CN 1848479 A 10/2006

(Continued)

OTHER PUBLICATIONS

Baxter, I., D. W. Cameron, and M. R. Thoseby. "Preparation and some reactions of 6-arylsulphonimidobenzoxazol-2 (3 H)-ones." Journal of the Chemical Society C: Organic 6 (1970): 850-853. (Year: 1970).*

(Continued)

*Primary Examiner* — Braelyn R Watson
(74) *Attorney, Agent, or Firm* — KDW Firm PLLC

(57) ABSTRACT

Provided are an organic electroluminescent material and device. The organic electroluminescent material is a novel compound containing a dehydrobenzooxazole, dehydrobenzothiazole, dehydrobenzoselenazole, dehydrobenzimidazole structure or a similar structure. These novel compounds have properties such as a deep LUMO, strong electron acceptability, a strong charge transfer ability and low volatility. Due to unique properties, these novel compounds have the prospect for wide applications in the field of organic semiconductors, especially the potential for use as p-type conductive doping materials, charge transporting layer materials, hole injection layer materials and electrode materials of the organic semiconductors.

23 Claims, 1 Drawing Sheet

(51) Int. Cl.

| | |
|---|---|
| ***H10K 50/15*** | (2023.01) |
| ***H10K 50/155*** | (2023.01) |
| ***H10K 50/17*** | (2023.01) |

(58) Field of Classification Search

CPC ............. H10K 85/621; H10K 85/6572; H10K 85/6576; H10K 85/6574; C07D 263/56; C07D 495/04; C07D 495/14; C07D 495/22; C07D 519/00; C07D 277/64; C07D 293/12; C07D 413/10; C07D 413/14; C07D 417/04; C07D 421/04; C07D 498/04; C07D 487/04; C07D 487/14; C07D 498/14; C07D 513/04; C07D 513/14; C07D 487/00–22; C07D 498/00–22; C07D 513/00–22; Y02E 10/549; C09K 11/06; C09K 2211/1007; C09K 2211/1033; C09K 2211/1037; C09K 2211/104; C09K 2211/1059; H01L 51/0072; H01L 51/0073; H01L 51/0074

See application file for complete search history.

(56) References Cited

U.S. PATENT DOCUMENTS

| | | | | |
|---|---|---|---|---|
| 5,844,363 | A | 12/1998 | Gu et al. | |
| 6,097,147 | A | 8/2000 | Baldo et al. | |
| 6,303,238 | B1 | 10/2001 | Thompson et al. | |
| 7,279,704 | B2 | 10/2007 | Walters et al. | |
| 7,968,416 | B2 | 6/2011 | Böttner et al. | |
| 12,239,018 | B2 * | 2/2025 | Cui | C09K 11/06 |
| 2003/0230980 | A1 | 12/2003 | Forrest et al. | |
| 2004/0174116 | A1 | 9/2004 | Lu et al. | |
| 2014/0246661 | A1 | 9/2014 | Yoon et al. | |
| 2015/0349273 | A1 | 12/2015 | Hung et al. | |
| 2016/0359122 | A1 | 12/2016 | Boudreault et al. | |
| 2020/0062778 | A1 | 2/2020 | Cui et al. | |
| 2020/0087311 | A1 | 3/2020 | Cui et al. | |
| 2021/0167298 | A1 | 6/2021 | Pang et al. | |
| 2021/0280795 | A1 * | 9/2021 | Cui | H10K 85/6574 |

FOREIGN PATENT DOCUMENTS

| | | | |
|---|---|---|---|
| CN | 109912619 | A | 6/2019 |
| CN | 112745333 | A | 5/2021 |
| CN | 113087711 | A | 7/2021 |
| CN | 113321620 | A | 8/2021 |

OTHER PUBLICATIONS

El-Shaieb, Kamal M., et al. "Facile Synthesis of Thiazole, Thiazine and Isoindole Derivatives via EDA Approach and Conventional Methods." Zeitschrift für Naturforschung B 68.8 (2013): 905-912. (Year: 2013).*

R. Stenutz, Hammett substituent constants, 2025. <https://www.stenutz.eu/chem/group_hammett.php> (Year: 2025).*

Koech et al., "Synthesis and Application of 1,3,4,5,7,8-Hexafluorotetracyanonaphthoquinodimethane (F6-TNAP): A Conductivity Dopant for Organic Light-Emitting Devices," Chem. Mater., vol. 22, pp. 3926-3932, 2010.

Tang and Vanslyke, "Organic electroluminescent diodes," Applied Physics Letters, vol. 51, No. 12, pp. 913-915, 1987.

Uoyama et al., "Highly efficient organic light-emitting diodes from delayed fluorescence," Nature, vol. 492, pp. 234-240, 2012.

Chinese First Office Action issued in CN Application No. 202111252563.6 on Apr. 9, 2024 and English translation, 11 pages.

Chinese First Search Report issued in CN Application No. 202111252563.6 on Apr. 9, 2024 and English translation, 4 pages.

Chinese Supplemental Search Report issued in CN Application No. 202111252563.6 on Apr. 9, 2024 and English translation, 4 pages.

* cited by examiner

ORGANIC ELECTROLUMINESCENT MATERIAL AND DEVICE THEREOF

CROSS-REFERENCE TO RELATED APPLICATION(S)

This application claims priority to Chinese Patent Application No. 202111252563.6 filed on Oct. 29, 2021, the disclosure of which is incorporated herein by reference in its entirety.

TECHNICAL FIELD

The present disclosure relates to compounds for organic electronic devices such as organic light-emitting devices. In particular, the present disclosure relates to a compound having a structure of Formula 1, an organic electroluminescent device comprising the compound and a compound combination comprising the compound.

BACKGROUND

Organic electronic devices include, but are not limited to, the following types: organic light-emitting diodes (OLEDs), organic field-effect transistors (O-FETs), organic light-emitting transistors (OLETs), organic photovoltaic devices (OPVs), dye-sensitized solar cells (DSSCs), organic optical detectors, organic photoreceptors, organic field-quench devices (OFQDs), light-emitting electrochemical cells (LECs), organic laser diodes and organic plasmon emitting devices.

In 1987, Tang and Van Slyke of Eastman Kodak reported a bilayer organic electroluminescent device, which comprises an arylamine hole transporting layer and a tris-8-hydroxyquinolate-aluminum layer as the electron and emitting layer (Applied Physics Letters, 1987, 51 (12): 913-915). Once a bias is applied to the device, green light was emitted from the device. This device laid the foundation for the development of modern organic light-emitting diodes (OLEDs). State-of-the-art OLEDs may comprise multiple layers such as charge injection and transporting layers, charge and exciton blocking layers, and one or multiple emissive layers between the cathode and anode. Since the OLED is a self-emitting solid state device, it offers tremendous potential for display and lighting applications. In addition, the inherent properties of organic materials, such as their flexibility, may make them well suited for particular applications such as fabrication on flexible substrates.

The OLED can be categorized as three different types according to its emitting mechanism. The OLED invented by Tang and van Slyke is a fluorescent OLED. It only utilizes singlet emission. The triplets generated in the device are wasted through nonradiative decay channels. Therefore, the internal quantum efficiency (IQE) of the fluorescent OLED is only 25%. This limitation hindered the commercialization of OLED. In 1997, Forrest and Thompson reported phosphorescent OLED, which uses triplet emission from heavy metal containing complexes as the emitter. As a result, both singlet and triplets can be harvested, achieving 100% IQE. The discovery and development of phosphorescent OLED contributed directly to the commercialization of active-matrix OLED (AMOLED) due to its high efficiency. Recently, Adachi achieved high efficiency through thermally activated delayed fluorescence (TADF) of organic compounds. These emitters have small singlet-triplet gap that makes the transition from triplet back to singlet possible. In the TADF device, the triplet excitons can go through reverse intersystem crossing to generate singlet excitons, resulting in high IQE.

OLEDs can also be classified as small molecule and polymer OLEDs according to the forms of the materials used. A small molecule refers to any organic or organometallic material that is not a polymer. The molecular weight of the small molecule can be large as long as it has well defined structure. Dendrimers with well-defined structures are considered as small molecules. Polymer OLEDs include conjugated polymers and non-conjugated polymers with pendant emitting groups. Small molecule OLED can become the polymer OLED if post polymerization occurred during the fabrication process.

There are various methods for OLED fabrication. Small molecule OLEDs are generally fabricated by vacuum thermal evaporation. Polymer OLEDs are fabricated by solution process such as spin-coating, inkjet printing, and slit printing. If the material can be dissolved or dispersed in a solvent, the small molecule OLED can also be produced by solution process.

The emitting color of the OLED can be achieved by emitter structural design. An OLED may comprise one emitting layer or a plurality of emitting layers to achieve desired spectrum. In the case of green, yellow, and red OLEDs, phosphorescent emitters have successfully reached commercialization. Blue phosphorescent device still suffers from non-saturated blue color, short device lifetime, and high operating voltage. Commercial full-color OLED displays normally adopt a hybrid strategy, using fluorescent blue and phosphorescent yellow, or red and green. At present, efficiency roll-off of phosphorescent OLEDs at high brightness remains a problem. In addition, it is desirable to have more saturated emitting color, higher efficiency, and longer device lifetime.

At present, most electron acceptor materials have various problems and are difficult to commercialize. For example, commonly used inorganic materials such as $FeCl_3$ and $MoO_3$ have a very high sublimation temperature, are unstable in a manufacturing process, or have poor thermal stability. Moreover, $FeCl_3$ has strong corrosion and causes great damage to evaporation equipment. For another example, an organic material HATCN has a relatively shallow LUMO, weak electron acceptability and a weak charge transfer ability. Thus, when used as a p-type conductive dopant, HATCN has a very poor effect. Moreover, HATCN has a strong crystallization property and has the problem of film formability in devices. Although F4-TCNQ and F6-TCNNQ have relatively deep LUMOs and very strong charge transfer abilities and are widely used as p-type conductive dopants in the field of electroluminescence, the high volatility (the sublimation temperature of F4-TCNQ is only 120° C. at a vacuum degree of $2.2\times10^{-4}$ Pa) and low evaporation temperature of F4-TCNQ and F6-TCNNQ affect the control of deposition of the materials in the manufacturing process of OLED devices, the reproducibility in a production process and the thermal stability of devices. Thus, F4-TCNQ and F6-TCNNQ are applied more cautiously in the commercial field. Since a hole injection layer has a very great impact on the voltage, efficiency and lifetime of an OLED device, it is very important and urgent to develop a p-type conductive doping material having high thermal stability, high film formability and a deep LUMO. HATCN, F4-TCNQ and F6-TCNNQ have the following structures:

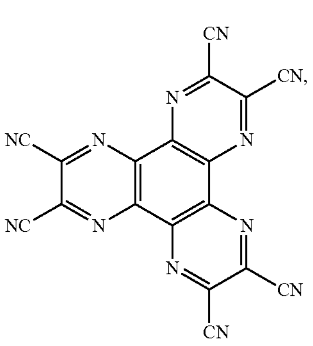

HATCN

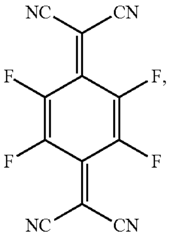

F4-TCNQ

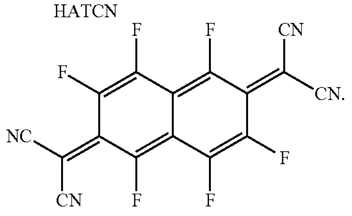

F6-TCNNQ

SUMMARY

The present disclosure aims to provide a series of compounds each having a structure of Formula 1 to solve at least part of the preceding problems. The compounds are novel compounds containing a dehydrobenzooxazole, dehydrobenzothiazole, dehydrobenzoselenazole, dehydrobenzimidazole structure or a similar structure. These novel compounds have strong electron acceptability and relatively high electron affinity. Due to unique properties, these novel compounds have the potential for wide applications in the field of organic semiconductors, especially the potential for use as p-type conductive doping materials, charge transporting layer materials, hole injection layer materials and electrode materials of the organic semiconductors.

According to an embodiment of the present disclosure, disclosed is a compound having a structure of Formula 1:

Formula 1

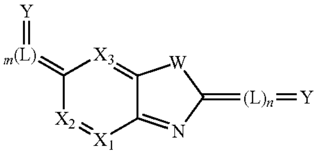

wherein Y is, at each occurrence identically or differently, selected from CR"R"', NR', O, S or Se;

W is, at each occurrence identically or differently, selected from O, S, Se or $NR_N$;

$X_1$ to $X_3$ are, at each occurrence identically or differently, selected from CR or N;

L is, at each occurrence identically or differently, selected from a cyclic conjugated structure comprising 4 to 30 ring atoms and comprising at least one intracyclic double bond and substituted by one or more substituents $R_L$';

R, $R_N$, R', R", R"' and $R_L$' are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, a hydroxyl group, a sulfanyl group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted alkylgermanyl having 3 to 20 carbon atoms, substituted or unsubstituted arylgermanyl having 6 to 20 carbon atoms and combinations thereof;

at least one of R, $R_N$, R', R" and R"' is a group having at least one electron-withdrawing group;

m and n are each selected from an integer from 0 to 1; and adjacent substituents R, $R_N$, R', R", R"' and $R_L$' can be optionally joined to form a ring.

According to another embodiment of the present disclosure, further disclosed is an electroluminescent device comprising an anode, a cathode and an organic layer disposed between the anode and the cathode, wherein the organic layer comprises the compound in the preceding embodiment.

According to another embodiment of the present disclosure, further disclosed is a compound combination comprising the compound in the preceding embodiment.

The compounds each having a structure of Formula 1 and disclosed in the present disclosure are novel compounds containing a dehydrobenzooxazole, dehydrobenzothiazole, dehydrobenzoselenazole, dehydrobenzimidazole structure or a similar structure. These novel compounds have properties such as a deep LUMO, strong electron acceptability, a strong charge transfer ability and low volatility. Due to unique properties, these novel compounds have the potential for wide applications in the field of organic semiconductors, especially the potential for use as the p-type conductive doping materials, charge transporting layer materials, hole injection layer materials and electrode materials of the organic semiconductors.

DETAILED DESCRIPTION

Figure 1:
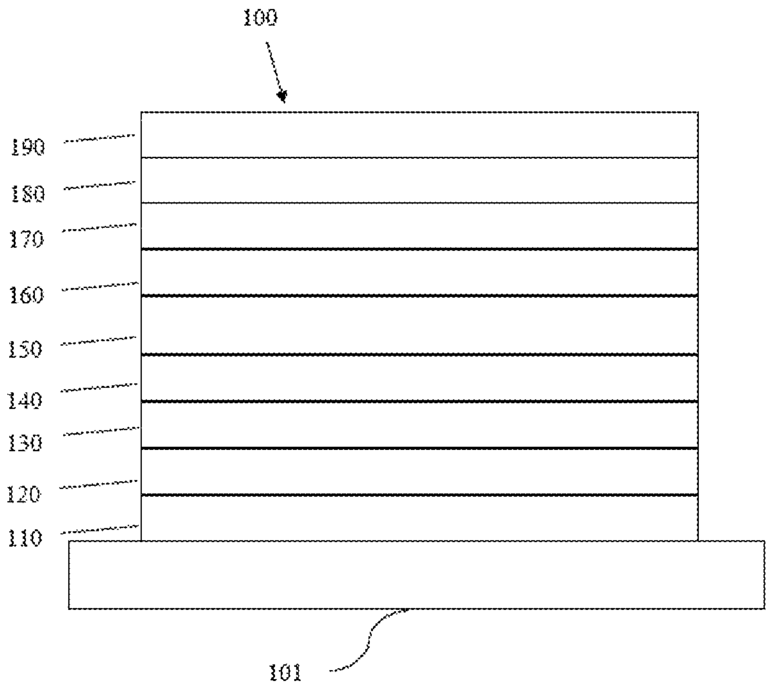
FIG. 1 is a schematic diagram of an organic light-emitting apparatus that may contain a compound and a compound combination disclosed herein.

OLEDs can be fabricated on various types of substrates such as glass, plastic, and metal foil. FIG. 1 schematically shows an organic light-emitting device 100 without limitation. The figures are not necessarily drawn to scale. Some of the layers in the figures can also be omitted as needed. Device 100 may include a substrate 101, an anode 110, a hole injection layer 120, a hole transport layer 130, an electron blocking layer 140, an emissive layer 150, a hole blocking layer 160, an electron transport layer 170, an electron injection layer 180 and a cathode 190. Device 100 may be fabricated by depositing the layers described in order. The properties and functions of these various layers, as well as example materials, are described in more detail in U.S. Pat. No. 7,279,704 at cols. 6-10, the contents of which are incorporated by reference herein in its entirety.

More examples for each of these layers are available. For example, a flexible and transparent substrate-anode combination is disclosed in U.S. Pat. No. 5,844,363, which is incorporated by reference herein in its entirety. An example of a p-doped hole transport layer is m-MTDATA doped with F4-TCNQ at a molar ratio of 50:1, as disclosed in U.S. Patent Application Publication No. 2003/0230980, which is incorporated by reference herein in its entirety. Examples of host materials are disclosed in U.S. Pat. No. 6,303,238 to Thompson et al., which is incorporated by reference herein in its entirety. An example of an n-doped electron transport layer is BPhen doped with Li at a molar ratio of 1:1, as disclosed in U.S. Patent Application Publication No. 2003/0230980, which is incorporated by reference herein in its entirety. U.S. Pat. Nos. 5,703,436 and 5,707,745, which are incorporated by reference herein in their entireties, disclose examples of cathodes including composite cathodes having a thin layer of metal such as Mg:Ag with an overlying transparent, electrically-conductive, sputter-deposited ITO layer. The theory and use of blocking layers are described in more detail in U.S. Pat. No. 6,097,147 and U.S. Patent Application Publication No. 2003/0230980, which are incorporated by reference herein in their entireties. Examples of injection layers are provided in U.S. Patent Application Publication No. 2004/0174116, which is incorporated by reference herein in its entirety. A description of protective layers may be found in U.S. Patent Application Publication No. 2004/0174116, which is incorporated by reference herein in its entirety.

The layered structure described above is provided by way of non-limiting examples. Functional OLEDs may be achieved by combining the various layers described in different ways, or layers may be omitted entirely. It may also include other layers not specifically described. Within each layer, a single material or a mixture of multiple materials can be used to achieve optimum performance. Any functional layer may include several sublayers. For example, the emissive layer may have two layers of different emitting materials to achieve desired emission spectrum.

In one embodiment, an OLED may be described as having an "organic layer" disposed between a cathode and an anode. This organic layer may include a single layer or multiple layers.

Figure 2:
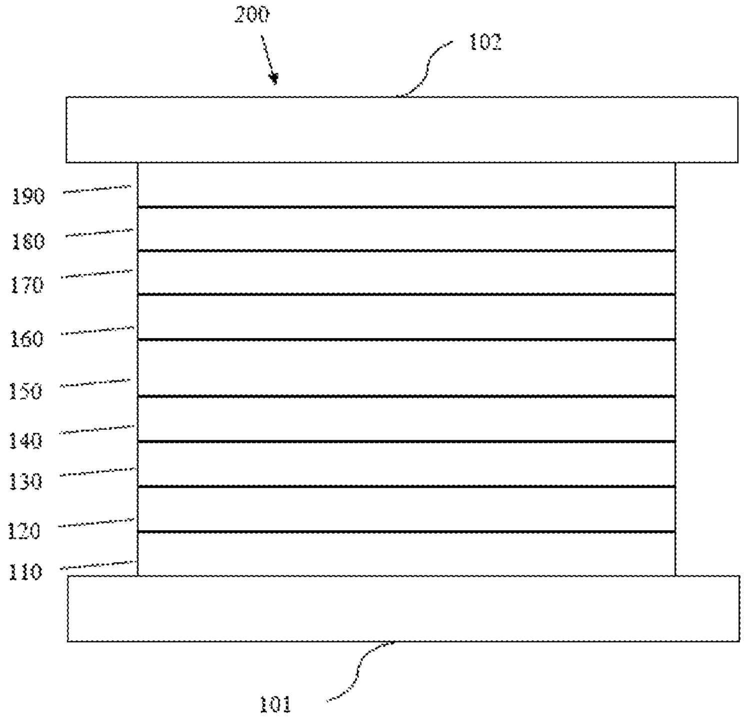
FIG. 2 is a schematic diagram of another organic light-emitting apparatus that may contain a compound and a compound combination disclosed herein.

An OLED can be encapsulated by a barrier layer. FIG. 2 schematically shows an organic light emitting device 200 without limitation. FIG. 2 differs from FIG. 1 in that the organic light emitting device include a barrier layer 102, which is above the cathode 190, to protect it from harmful species from the environment such as moisture and oxygen. Any material that can provide the barrier function can be used as the barrier layer such as glass or organic-inorganic hybrid layers. The barrier layer should be placed directly or indirectly outside of the OLED device. Multilayer thin film encapsulation was described in U.S. Pat. No. 7,968,146, which is incorporated by reference herein in its entirety.

Devices fabricated in accordance with embodiments of the present disclosure can be incorporated into a wide variety of consumer products that have one or more of the electronic component modules (or units) incorporated therein. Some examples of such consumer products include flat panel displays, monitors, medical monitors, televisions, billboards, lights for interior or exterior illumination and/or signaling, heads-up displays, fully or partially transparent displays, flexible displays, smart phones, tablets, phablets, wearable devices, smart watches, laptop computers, digital cameras, camcorders, viewfinders, micro-displays, 3-D displays, vehicles displays, and vehicle tail lights.

The materials and structures described herein may be used in other organic electronic devices listed above.

As used herein, "top" means furthest away from the substrate, while "bottom" means closest to the substrate. Where a first layer is described as "disposed over" a second layer, the first layer is disposed further away from the substrate. There may be other layers between the first and second layers, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

It is believed that the internal quantum efficiency (IQE) of fluorescent OLEDs can exceed the 25% spin statistics limit through delayed fluorescence. As used herein, there are two types of delayed fluorescence, i.e. P-type delayed fluorescence and E-type delayed fluorescence. P-type delayed fluorescence is generated from triplet-triplet annihilation (TTA).

On the other hand, E-type delayed fluorescence does not rely on the collision of two triplets, but rather on the transition between the triplet states and the singlet excited states. Compounds that are capable of generating E-type delayed fluorescence are required to have very small singlet-triplet gaps to convert between energy states. Thermal energy can activate the transition from the triplet state back to the singlet state. This type of delayed fluorescence is also known as thermally activated delayed fluorescence (TADF). A distinctive feature of TADF is that the delayed component increases as temperature rises. If the reverse intersystem crossing (RISC) rate is fast enough to minimize the non-radiative decay from the triplet state, the fraction of back populated singlet excited states can potentially reach 75%. The total singlet fraction can be 100%, far exceeding 25% of the spin statistics limit for electrically generated excitons.

E-type delayed fluorescence characteristics can be found in an exciplex system or in a single compound. Without being bound by theory, it is believed that E-type delayed fluorescence requires the luminescent material to have a small singlet-triplet energy gap ($\Delta E_{S-T}$). Organic, non-metal containing, donor-acceptor luminescent materials may be able to achieve this. The emission in these materials is generally characterized as a donor-acceptor charge-transfer (CT) type emission. The spatial separation of the HOMO and LUMO in these donor-acceptor type compounds generally results in small $\Delta E_{S-T}$. These states may involve CT states. Generally, donor-acceptor luminescent materials are constructed by connecting an electron donor moiety such as amino- or carbazole-derivatives and an electron acceptor moiety such as N-containing six-membered aromatic rings.

Definition of Terms of Substituents

Halogen or halide—as used herein includes fluorine, chlorine, bromine, and iodine.

Alkyl—as used herein includes both straight and branched chain alkyl groups. Alkyl may be alkyl having 1 to 20 carbon atoms, preferably alkyl having 1 to 12 carbon atoms, and more preferably alkyl having 1 to 6 carbon atoms. Examples of alkyl groups include a methyl group, an ethyl group, a propyl group, an isopropyl group, a n-butyl group, an s-butyl group, an isobutyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, a neopentyl group, a 1-methylpentyl group, a 2-methylpentyl group, a 1-pentylhexyl group, a 1-butylpentyl group, a 1-heptyloctyl group, and a 3-methylpentyl group. Of the above, preferred are a methyl group, an ethyl group, a propyl group, an isopropyl group, a n-butyl group, an s-butyl group, an isobutyl group, a t-butyl group, an n-pentyl group, a neopentyl group, and an n-hexyl group. Additionally, the alkyl group may be optionally substituted.

Cycloalkyl—as used herein includes cyclic alkyl groups. The cycloalkyl groups may be those having 3 to 20 ring carbon atoms, preferably those having 4 to 10 carbon atoms. Examples of cycloalkyl include cyclobutyl, cyclopentyl, cyclohexyl, 4-methylcyclohexyl, 4,4-dimethylcyclohexyl, 1-adamantyl, 2-adamantyl, 1-norbornyl, 2-norbornyl, and the like. Of the above, preferred are cyclopentyl, cyclohexyl, 4-methylcyclohexyl, and 4,4-dimethylcyclohexyl. Additionally, the cycloalkyl group may be optionally substituted.

Heteroalkyl—as used herein, includes a group formed by replacing one or more carbons in an alkyl chain with a hetero-atom(s) selected from the group consisting of a nitrogen atom, an oxygen atom, a sulfur atom, a selenium atom, a phosphorus atom, a silicon atom, a germanium atom, and a boron atom. Heteroalkyl may be those having 1 to 20 carbon atoms, preferably those having 1 to 10 carbon atoms, and more preferably those having 1 to 6 carbon atoms. Examples of heteroalkyl include methoxymethyl, ethoxymethyl, ethoxyethyl, methylthiomethyl, ethylthiomethyl, ethylthioethyl, methoxymethoxymethyl, ethoxymethoxymethyl, ethoxyethoxyethyl, hydroxymethyl, hydroxyethyl, hydroxypropyl, mercaptomethyl, mercaptoethyl, mercaptopropyl, aminomethyl, aminoethyl, aminopropyl, dimethylaminomethyl, trimethylgermanylmethyl, trimethylgermanylethyl, trimethylgermanylisopropyl, dimethylethylgermanylmethyl, dimethylisopropylgermanylmethyl, tert-butyldimethylgermanylmethyl, triethylgermanylmethyl, triethylgermanylethyl, triisopropylgermanylmethyl, triisopropylgermanylethyl, trimethylsilylmethyl, trimethylsilylethyl, trimethylsilylisopropyl, triisopropylsilylmethyl and triisopropylsilylethyl. Additionally, the heteroalkyl group may be optionally substituted.

Alkenyl—as used herein includes straight chain, branched chain, and cyclic alkene groups. Alkenyl may be those having 2 to 20 carbon atoms, preferably those having 2 to 10 carbon atoms. Examples of alkenyl include vinyl, 1-propenyl group, 1-butenyl, 2-butenyl, 3-butenyl, 1,3-butanedienyl, 1-methylvinyl, styryl, 2,2-diphenylvinyl, 1,2-diphenylvinyl, 1-methylallyl, 1,1-dimethylallyl, 2-methylallyl, 1-phenylallyl, 2-phenylallyl, 3-phenylallyl, 3,3-diphenylallyl, 1,2-dimethylallyl, 1-phenyl-1-butenyl, 3-phenyl-1-butenyl, cyclopentenyl, cyclopentadienyl, cyclohexenyl, cycloheptenyl, cycloheptatrienyl, cyclooctenyl, cyclooctatetraenyl, and norbornenyl. Additionally, the alkenyl group may be optionally substituted.

Alkynyl—as used herein includes straight chain alkynyl groups. Alkynyl may be those having 2 to 20 carbon atoms, preferably those having 2 to 10 carbon atoms. Examples of alkynyl groups include ethynyl, propynyl, propargyl, 1-butynyl, 2-butynyl, 3-butynyl, 1-pentynyl, 2-pentynyl, 3,3-dimethyl-1-butynyl, 3-ethyl-3-methyl-1-pentynyl, 3,3-diisopropyl-1-pentynyl, phenylethynyl, phenylpropynyl, etc. Of the above, preferred are ethynyl, propynyl, propargyl, 1-butynyl, 2-butynyl, 3-butynyl, 1-pentynyl, and phenylethynyl. Additionally, the alkynyl group may be optionally substituted.

Aryl or an aromatic group—as used herein includes non-condensed and condensed systems. Aryl may be those having 6 to 30 carbon atoms, preferably those having 6 to 20 carbon atoms, and more preferably those having 6 to 12 carbon atoms. Examples of aryl groups include phenyl, biphenyl, terphenyl, triphenylene, tetraphenylene, naphthalene, anthracene, phenalene, phenanthrene, fluorene, pyrene, chrysene, perylene, and azulene, preferably phenyl, biphenyl, terphenyl, triphenylene, fluorene, and naphthalene. Examples of non-condensed aryl groups include phenyl, biphenyl-2-yl, biphenyl-3-yl, biphenyl-4-yl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-(2-phenylpropyl)phenyl, 4'-methylbiphenylyl, 4"-t-butyl-p-terphenyl-4-yl, o-cumenyl, m-cumenyl, p-cumenyl, 2,3-xylyl, 3,4-xylyl, 2,5-xylyl, mesityl, and m-quarterphenyl. Additionally, the aryl group may be optionally substituted.

Heterocyclic groups or heterocycle—as used herein include non-aromatic cyclic groups. Non-aromatic heterocyclic groups include saturated heterocyclic groups having 3 to 20 ring atoms and unsaturated non-aromatic heterocyclic groups having 3 to 20 ring atoms, where at least one ring atom is selected from the group consisting of a nitrogen atom, an oxygen atom, a sulfur atom, a selenium atom, a silicon atom, a phosphorus atom, a germanium atom, and a boron atom. Preferred non-aromatic heterocyclic groups are those having 3 to 7 ring atoms, each of which includes at least one hetero-atom such as nitrogen, oxygen, silicon, or sulfur. Examples of non-aromatic heterocyclic groups include oxiranyl, oxetanyl, tetrahydrofuranyl, tetrahydropyranyl, dioxolanyl, dioxanyl, aziridinyl, dihydropyrrolyl, tetrahydropyrrolyl, piperidinyl, oxazolidinyl, morpholinyl, piperazinyl, oxepinyl, thiepinyl, azepinyl, and tetrahydrosilolyl. Additionally, the heterocyclic group may be optionally substituted.

Heteroaryl—as used herein, includes non-condensed and condensed hetero-aromatic groups having 1 to 5 hetero-atoms, where at least one hetero-atom is selected from the group consisting of a nitrogen atom, an oxygen atom, a sulfur atom, a selenium atom, a silicon atom, a phosphorus atom, a germanium atom, and a boron atom. A hetero-aromatic group is also referred to as heteroaryl. Heteroaryl may be those having 3 to 30 carbon atoms, preferably those having 3 to 20 carbon atoms, and more preferably those having 3 to 12 carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridoindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Alkoxy—as used herein, is represented by —O-alkyl, —O-cycloalkyl, —O-heteroalkyl, or —O-heterocyclic group. Examples and preferred examples of alkyl, cycloalkyl, heteroalkyl, and heterocyclic groups are the same as those described above. Alkoxy groups may be those having 1 to 20 carbon atoms, preferably those having 1 to 6 carbon atoms. Examples of alkoxy groups include methoxy, ethoxy, propoxy, butoxy, pentyloxy, hexyloxy, cyclopropyloxy, cyclobutyloxy, cyclopentyloxy, cyclohexyloxy, tetrahydrofuranyloxy, tetrahydropyranyloxy, methoxypropyloxy, ethoxyethyloxy, methoxymethyloxy, and ethoxymethyloxy. Additionally, the alkoxy group may be optionally substituted.

Aryloxy—as used herein, is represented by —O-aryl or —O-heteroaryl. Examples and preferred examples of aryl and heteroaryl are the same as those described above. Aryloxy groups may be those having 6 to 30 carbon atoms, preferably those having 6 to 20 carbon atoms. Examples of aryloxy groups include phenoxy and biphenyloxy. Additionally, the aryloxy group may be optionally substituted.

Arylalkyl—as used herein, contemplates alkyl substituted with an aryl group. Arylalkyl may be those having 7 to 30 carbon atoms, preferably those having 7 to 20 carbon atoms, and more preferably those having 7 to 13 carbon atoms. Examples of arylalkyl groups include benzyl, 1-phenylethyl, 2-phenylethyl, 1-phenylisopropyl, 2-phenylisopropyl, phenyl-t-butyl, alpha-naphthylmethyl, 1-alpha-naphthylethyl, 2-alpha-naphthylethyl, 1-alpha-naphthylisopropyl, 2-alpha-naphthylisopropyl, beta-naphthylmethyl, 1-beta-naphthylethyl, 2-beta-naphthylethyl, 1-beta-naphthylisopropyl, 2-beta-naphthylisopropyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-hydroxybenzyl, m-hydroxybenzyl, o-hydroxybenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-hydroxy-2-phenylisopropyl, and 1-chloro-2-phenylisopropyl. Of the above, preferred are benzyl, p-cyanobenzyl, m-cyanobenzyl, o-cyanobenzyl, 1-phenyl ethyl, 2-phenylethyl, 1-phenylisopropyl, and 2-phenylisopropyl. Additionally, the arylalkyl group may be optionally substituted.

Alkylsilyl—as used herein, contemplates a silyl group substituted with an alkyl group. Alkylsilyl groups may be those having 3 to 20 carbon atoms, preferably those having 3 to 10 carbon atoms. Examples of alkylsilyl groups include trimethylsilyl, triethylsilyl, methyldiethylsilyl, ethyldimethyl silyl, tripropyl silyl, tributyl silyl, triisopropylsilyl, methyldiisopropylsilyl, dimethylisopropylsilyl, tri-t-butylsilyl, triisobutylsilyl, dimethyl t-butylsilyl, and methyldi-t-butylsilyl. Additionally, the alkylsilyl group may be optionally substituted.

Arylsilyl—as used herein, contemplates a silyl group substituted with at least one aryl group. Arylsilyl groups may be those having 6 to 30 carbon atoms, preferably those having 8 to 20 carbon atoms. Examples of arylsilyl groups include triphenylsilyl, phenyldibiphenylylsilyl, diphenylbiphenylsilyl, phenyldiethylsilyl, diphenylethylsilyl, phenyldimethylsilyl, diphenylmethylsilyl, phenyldiisopropylsilyl, diphenylisopropylsilyl, diphenylbutylsilyl, diphenylisobutylsilyl, diphenyl t-butylsilyl. Additionally, the arylsilyl group may be optionally substituted.

Alkylgermanyl—as used herein contemplates germanyl substituted with an alkyl group. The alkylgermanyl may be those having 3 to 20 carbon atoms, preferably those having 3 to 10 carbon atoms. Examples of alkylgermanyl include trimethylgermanyl, triethylgermanyl, methyldiethylgermanyl, ethyldimethylgermanyl, tripropylgermanyl, tributylgermanyl, triisopropylgermanyl, methyldiisopropylgermanyl, dimethylisopropylgermanyl, tri-t-butylgermanyl, triisobutylgermanyl, dimethyl-t-butylgermanyl, and methyldi-t-butylgermanyl. Additionally, the alkylgermanyl may be optionally substituted.

Arylgermanyl—as used herein contemplates a germanyl substituted with at least one aryl group or heteroaryl group. Arylgermanyl may be those having 6 to 30 carbon atoms, preferably those having 8 to 20 carbon atoms. Examples of arylgermanyl include triphenylgermanyl, phenyldibiphenylylgermanyl, diphenylbiphenylgermanyl, phenyldiethylgermanyl, diphenylethylgermanyl, phenyldimethylgermanyl, diphenylmethylgermanyl, phenyldiisopropylgermanyl, diphenylisopropylgermanyl, diphenylbutylgermanyl, diphenylisobutylgermanyl, and diphenyl-t-butylgermanyl. Additionally, the arylgermanyl may be optionally substituted.

The term "aza" in azadibenzofuran, azadibenzothiophene, etc. means that one or more of C—H groups in the respective aromatic fragment are replaced by a nitrogen atom. For example, azatriphenylene encompasses dibenzo[f,h]quinoxaline, dibenzo[f,h]quinoline and other analogs with two or more nitrogens in the ring system. One of ordinary skill in the art can readily envision other nitrogen analogs of the aza-derivatives described above, and all such analogs are intended to be encompassed by the terms as set forth herein.

In the present disclosure, unless otherwise defined, when any term of the group consisting of substituted alkyl, substituted cycloalkyl, substituted heteroalkyl, substituted heterocyclic group, substituted arylalkyl, substituted alkoxy, substituted aryloxy, substituted alkenyl, substituted alkynyl, substituted aryl, substituted heteroaryl, substituted alkylsilyl, substituted arylsilyl, substituted alkylgermanyl, substituted arylgermanyl, substituted amino, substituted acyl, substituted carbonyl, a substituted carboxylic acid group, a substituted ester group, substituted sulfinyl, substituted sulfonyl, and substituted phosphino is used, it means that any group of alkyl, cycloalkyl, heteroalkyl, heterocyclic group, arylalkyl, alkoxy, aryloxy, alkenyl, alkynyl, aryl, heteroaryl, alkylsilyl, arylsilyl, alkylgermanyl, arylgermanyl, amino, acyl, carbonyl, a carboxylic acid group, an ester group, sulfinyl, sulfonyl, and phosphino may be substituted with one or more groups selected from the group consisting of deuterium, halogen, unsubstituted alkyl having 1 to 20 carbon atoms, unsubstituted cycloalkyl having 3 to 20 ring carbon atoms, unsubstituted heteroalkyl having 1 to 20 carbon atoms, an unsubstituted heterocyclic group having 3 to 20 ring atoms, unsubstituted arylalkyl having 7 to 30 carbon atoms, unsubstituted alkoxy having 1 to 20 carbon atoms, unsubstituted aryloxy having 6 to 30 carbon atoms, unsubstituted alkenyl having 2 to 20 carbon atoms, unsubstituted alkynyl having 2 to 20 carbon atoms, unsubstituted aryl having 6 to 30 carbon atoms, unsubstituted heteroaryl having 3 to 30 carbon atoms, unsubstituted alkylsilyl having 3 to 20 carbon atoms, unsubstituted arylsilyl group having 6 to 20 carbon atoms, unsubstituted alkylgermanyl group having 3 to 20 carbon atoms, unsubstituted arylgermanyl group having 6 to 20 carbon atoms, unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or an attached fragment are considered to be equivalent.

In the compounds mentioned in the present disclosure, hydrogen atoms may be partially or fully replaced by deuterium. Other atoms such as carbon and nitrogen may also be replaced by their other stable isotopes. The replacement by other stable isotopes in the compounds may be preferred due to its enhancements of device efficiency and stability.

In the compounds mentioned in the present disclosure, multiple substitutions refer to a range that includes di-substitutions, up to the maximum available substitutions. When substitution in the compounds mentioned in the present disclosure represents multiple substitutions (including di-, tri-, and tetra-substitutions etc.), that means the substituent may exist at a plurality of available substitution positions on its linking structure, the substituents present at a plurality of available substitution positions may have the same structure or different structures.

In the compounds mentioned in the present disclosure, adjacent substituents in the compounds cannot be joined to form a ring unless otherwise explicitly defined, for example, adjacent substituents can be optionally joined to form a ring. In the compounds mentioned in the present disclosure, the expression that adjacent substituents can be optionally joined to form a ring includes a case where adjacent substituents may be joined to form a ring and a case where adjacent substituents are not joined to form a ring. When adjacent substituents can be optionally joined to form a ring, the ring formed may be monocyclic or polycyclic (including spirocyclic, endocyclic, fusedcyclic, and etc.), as well as alicyclic, heteroalicyclic, aromatic, or heteroaromatic. In such expression, adjacent substituents may refer to substituents bonded to the same atom, substituents bonded to carbon atoms which are directly bonded to each other, or substituents bonded to carbon atoms which are more distant from each other. Preferably, adjacent substituents refer to substituents bonded to the same carbon atom and substituents bonded to carbon atoms which are directly bonded to each other.

In the present disclosure, the number of ring atoms represents the number of atoms constituting a ring itself in a compound (e.g., a monocyclic compound, a fused ring compound, a crosslinking compound, a carbocyclic compound, a heterocyclic compound) whose atoms are bonded into the ring. When the ring is substituted by a substituent, atoms included in the substituent are not included in the number of ring atoms. The "number of ring atoms" recorded herein has the same meaning unless otherwise specified.

The expression that adjacent substituents can be optionally joined to form a ring is also intended to mean that two substituents bonded to the same carbon atom are joined to each other via a chemical bond to form a ring, which can be exemplified by the following formula:

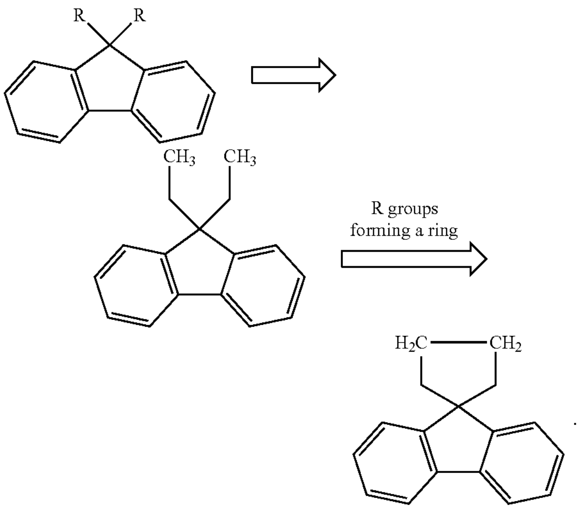

The expression that adjacent substituents can be optionally joined to form a ring is also intended to mean that two substituents bonded to carbon atoms which are directly bonded to each other are joined to each other via a chemical bond to form a ring, which can be exemplified by the following formula:

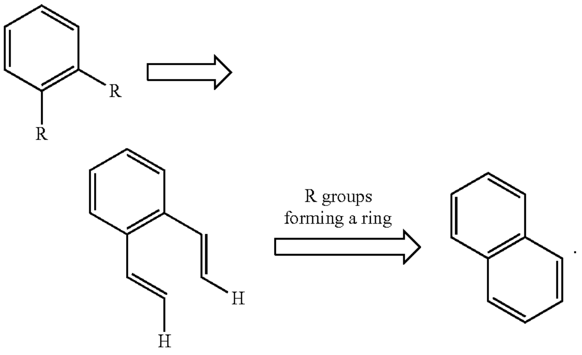

The expression that adjacent substituents can be optionally joined to form a ring is also intended to mean that two substituents bonded to further distant carbon atoms are joined to each other via a chemical bond to form a ring, which can be exemplified by the following formula:

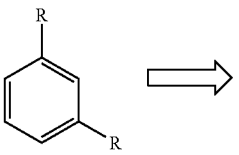

-continued

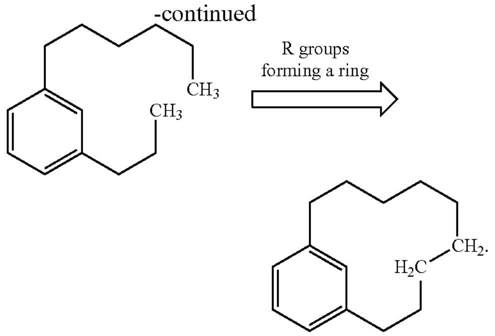

Furthermore, the expression that adjacent substituents can be optionally joined to form a ring is also intended to mean that, in the case where one of the two substituents bonded to carbon atoms which are directly bonded to each other represents hydrogen, the second substituent is bonded at a position at which the hydrogen atom is bonded, thereby forming a ring. This is exemplified by the following formula:

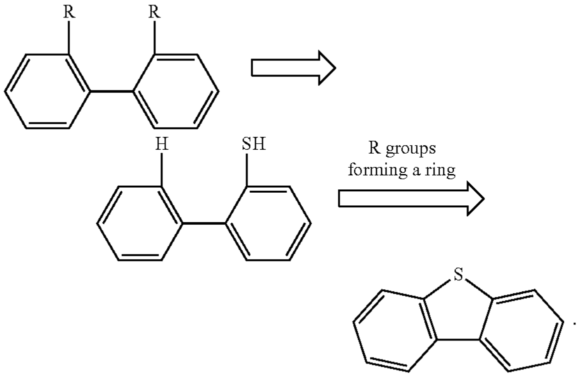

According to an embodiment of the present disclosure, disclosed is a compound having a structure of Formula 1:

Formula 1

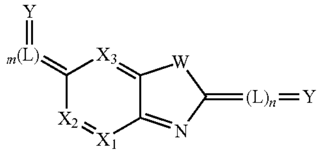

wherein Y is, at each occurrence identically or differently, selected from CR''R''', NR', O, S or Se;

W is, at each occurrence identically or differently, selected from O, S, Se or $NR_N$;

$X_1$ to $X_3$ are, at each occurrence identically or differently, selected from CR or N;

L is, at each occurrence identically or differently, selected from a cyclic conjugated structure comprising 4 to 30 ring atoms and comprising at least one intracyclic double bond and substituted by one or more substituents $R_L$';

R, $R_N$, R', R'', R''' and $R_L$' are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, SF5, a boranyl group, a sulfinyl group, a sulfonyl group, a phosphoroso group, a hydroxyl group, a sulfanyl group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted alkylgermanyl having 3 to 20 carbon atoms, substituted or unsubstituted arylgermanyl having 6 to 20 carbon atoms and combinations thereof;

at least one of R, $R_N$, R', R'' and R''' is a group having at least one electron-withdrawing group;

m and n are each selected from an integer from 0 to 1; and adjacent substituents R, $R_N$, R', R'', R''' and $R_L$' can be optionally joined to form a ring.

In this embodiment, the expression that "adjacent substituents R, $R_N$, R', R'', R''' and $R_L$' can be optionally joined to form a ring" is intended to mean that any one or more of any two adjacent substituents among the substituents R, $R_N$, R', R'', R''' and $R_L$', such as two R, two $R_L$', R and $R_N$, and R'' and R''', can be optionally joined to form a ring. Obviously, it is possible that these adjacent substituents R, $R_N$, R', R'', R''' and $R_L$' are not joined to form a ring.

In this embodiment, when m or n is 0, which means that L does not exist, Y is directly connected to the six-membered and five-membered conjugated ring comprising $X_1$ to $X_3$ and W in Formula 1.

According to an embodiment of the present disclosure, W is, at each occurrence identically or differently, selected from O, S or Se.

According to an embodiment of the present disclosure, W is, at each occurrence identically or differently, selected from O or S.

According to an embodiment of the present disclosure, W is, at each occurrence identically or differently, selected from O.

According to an embodiment of the present disclosure, $m+n \leq 1$.

According to an embodiment of the present disclosure, $m+n=0$.

According to an embodiment of the present disclosure, at least one of $X_1$ to $X_3$ is selected from CR.

According to an embodiment of the present disclosure, at least two of $X_1$ to $X_3$ are selected from CR.

According to an embodiment of the present disclosure, Y is, at each occurrence identically or differently, selected from CR''R''' or NR', and each of R', R'' and R''' is the group having at least one electron-withdrawing group.

According to an embodiment of the present disclosure, Y is, at each occurrence identically or differently, selected from CR''R''' or NR', and each of R, $R_N$, R', R'' and R''' is the group having at least one electron-withdrawing group.

According to an embodiment of the present disclosure, Y is, at each occurrence identically or differently, selected from CR''R''' or NR', and each of R, $R_N$, R', R'', R''' and $R_L$' is the group having at least one electron-withdrawing group.

According to an embodiment of the present disclosure, a Hammett constant of the electron-withdrawing group is ≥0.05, preferably ≥0.3, and more preferably ≥0.5.

In the present disclosure, the electron-withdrawing group has a Hammett substituent constant greater than or equal to 0.05. The relatively strong electron withdrawing ability can significantly reduce the LUMO energy level of the compound and improve charge mobility.

It is to be noted that the Hammett substituent constant includes a para constant and/or a meta constant of a Hammett substituent, and as long as one of the para constant and the meta constant is greater than or equal to 0.05, the Hammett substituent can be used as the preferred electron-withdrawing group of the present disclosure.

According to an embodiment of the present disclosure, the electron-withdrawing group is selected from the group consisting of: halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, an aza-aromatic ring group and any one of the following groups substituted by one or more of halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group and an aza-aromatic ring group: alkyl having 1 to 20 carbon atoms, cycloalkyl having 3 to 20 ring carbon atoms, heteroalkyl having 1 to 20 carbon atoms, arylalkyl having 7 to 30 carbon atoms, alkoxy having 1 to 20 carbon atoms, aryloxy having 6 to 30 carbon atoms, alkenyl having 2 to 20 carbon atoms, alkynyl having 2 to 20 carbon atoms, aryl having 6 to 30 carbon atoms, heteroaryl having 3 to 30 carbon atoms, alkylsilyl having 3 to 20 carbon atoms, arylsilyl having 6 to 20 carbon atoms, substituted or unsubstituted alkylgermanyl having 3 to 20 carbon atoms, substituted or unsubstituted arylgermanyl having 6 to 20 carbon atoms and combinations thereof.

According to an embodiment of the present disclosure, the electron-withdrawing group is selected from the group consisting of: F, $CF_3$, $OCF_3$, $SF_5$, $SO_2CF_3$, cyano, isocyano, SCN, OCN, pyrimidinyl, triazinyl and combinations thereof.

According to an embodiment of the present disclosure, Y is, at each occurrence identically or differently, selected from the group consisting of the following structures:

O, S, Se,

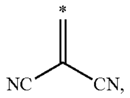
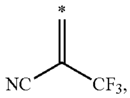
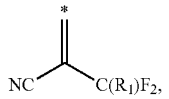
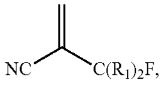
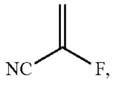
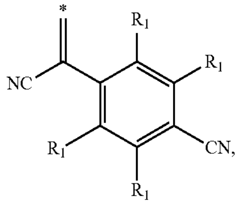
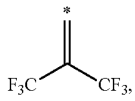

-continued

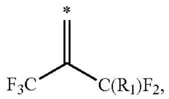
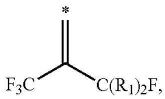
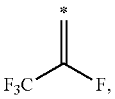
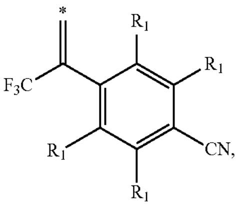
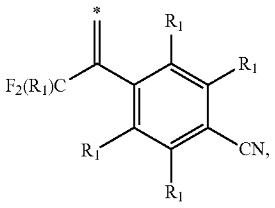
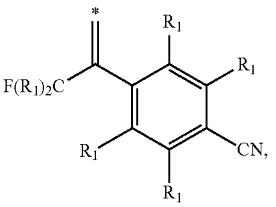
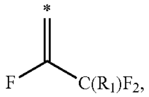
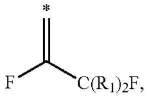
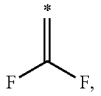
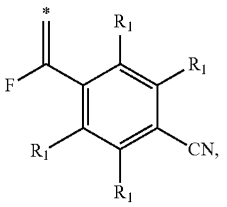
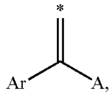
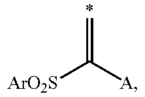
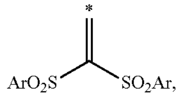
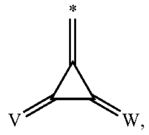
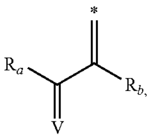
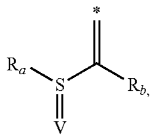
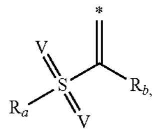
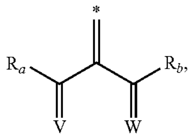
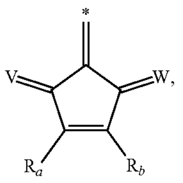
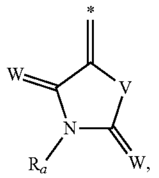
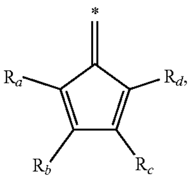

-continued

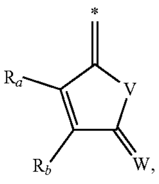

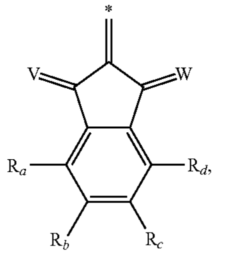

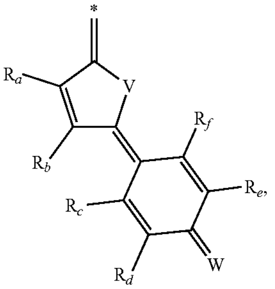

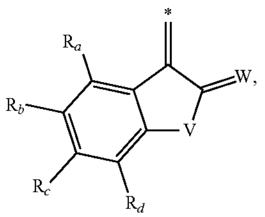

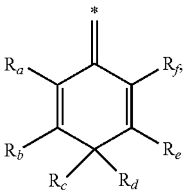

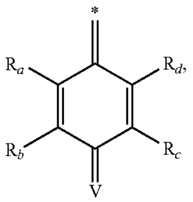

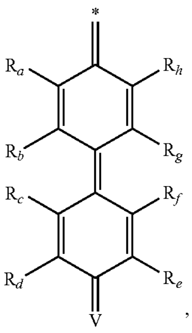

,

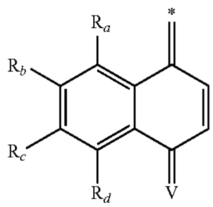

,

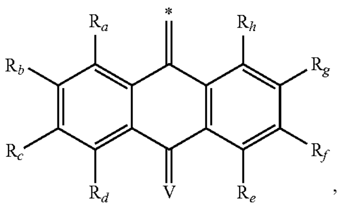

,

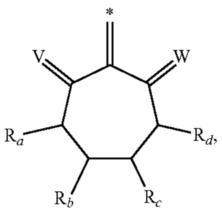

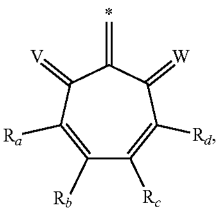

-continued

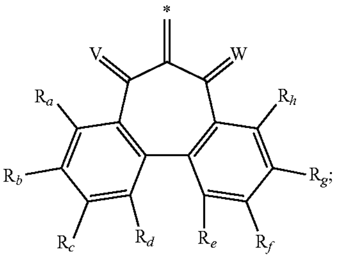

wherein $R_1$ is, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted alkylgermanyl having 3 to 20 carbon atoms, substituted or unsubstituted arylgermanyl having 6 to 20 carbon atoms and combinations thereof;

preferably, $R_1$ is, at each occurrence identically or differently, selected from the group consisting of: F, $CF_3$, $OCF_3$, $SF_5$, $SO_2CF_3$, cyano, isocyano, SCN, OCN, pentafluorophenyl, 4-cyanotetrafluorophenyl, tetrafluoropyridyl, pyrimidinyl, triazinyl and combinations thereof;

wherein V and W are, at each occurrence identically or differently, selected from $CR_vR_w$, $NR_v$, O, S or Se;

wherein Ar is, at each occurrence identically or differently, selected from substituted or unsubstituted aryl having 6 to 30 carbon atoms or substituted or unsubstituted heteroaryl having 3 to 30 carbon atoms;

wherein A, $R_a$, $R_b$, $R_c$, $R_d$, $R_e$, $R_f$, $R_g$, $R_h$, $R_v$ and $R_w$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted alkylgermanyl having 3 to 20 carbon atoms, substituted or unsubstituted arylgermanyl having 6 to 20 carbon atoms and combinations thereof;

wherein A is a group having at least one electron-withdrawing group, and for any one of the structures, when one or more of $R_a$, $R_b$, $R_c$, $R_d$, $R_e$, $R_f$, $R_g$, $R_h$, $R_v$ and $R_w$ are present, at least one of $R_a$, $R_b$, $R_c$, $R_d$, $R_e$, $R_f$, $R_g$, $R_h$, $R_v$ and $R_w$ is a group having at least one electron withdrawing group; preferably, the group having at least one electron withdrawing group is selected from the group consisting of: F, $CF_3$, $OCF_3$, $SF_5$, $SO_2CF_3$, cyano, isocyano, SCN, OCN, pentafluorophenyl, 4-cyanotetrafluorophenyl, tetrafluoropyridyl, pyrimidinyl, triazinyl and combinations thereof.

In this embodiment, "*" represents a position where Y is connected to L or the six-membered and five-membered conjugated ring comprising $X_1$ to $X_3$ and W in Formula 1. When m or n is 0, "*" represents a position where Y is connected to the six-membered and five-membered conjugated ring comprising $X_1$ to $X_3$ and Win Formula 1. When m or n is 1, "*" represents a position where Y is connected to L in Formula 1.

According to an embodiment of the present disclosure, Y is, at each occurrence identically or differently, selected from the group consisting of:

O, S, Se,

A1

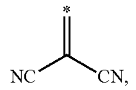

A2

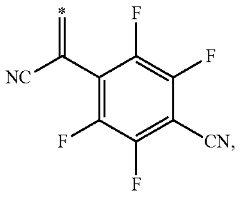

A3

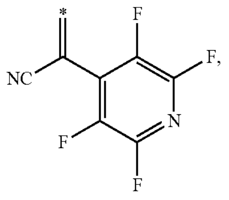

A4

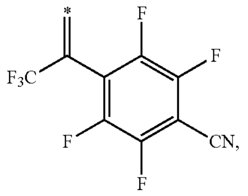

A5

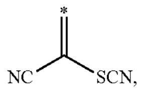

-continued

A6

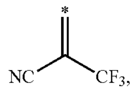

A7

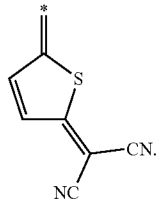

In this embodiment, "*" represents a position where Y is connected to L or the six-membered and five-membered conjugated ring comprising $X_1$ to $X_3$ and W in Formula 1. When m or n is 0, "*" represents a position where Y is connected to the six-membered and five-membered conjugated ring comprising $X_1$ to $X_3$ and Win Formula 1. When m or n is 1, "*" represents a position where Y is connected to L in Formula 1.

According to an embodiment of the present disclosure, Y is selected from

A1

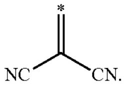

In this embodiment, "*" represents a position where Y is connected to L or the six-membered and five-membered conjugated ring comprising $X_1$ to $X_3$ and W in Formula 1. When m or n is 0, "*" represents a position where Y is connected to the six-membered and five-membered conjugated ring comprising $X_1$ to $X_3$ and Win Formula 1. When m or n is 1, "*" represents a position where Y is connected to L in Formula 1.

According to an embodiment of the present disclosure, R and $R_N$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, unsubstituted alkyl having 1 to 20 carbon atoms, unsubstituted cycloalkyl having 3 to 20 ring carbon atoms, unsubstituted alkoxy having 1 to 20 carbon atoms, unsubstituted alkenyl having 2 to 20 carbon atoms, unsubstituted aryl having 6 to 30 carbon atoms, unsubstituted heteroaryl having 3 to 30 carbon atoms, any one of the following groups substituted by one or more of halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group and a phosphoroso group: alkyl having 1 to 20 carbon atoms, cycloalkyl having 3 to 20 ring carbon atoms, alkoxy having 1 to 20 carbon atoms, alkenyl having 2 to 20 carbon atoms, aryl having 6 to 30 carbon atoms and heteroaryl having 3 to 30 carbon atoms, and combinations thereof.

According to an embodiment of the present disclosure, R and $R_N$ are, at each occurrence identically or differently, selected from the group consisting of: hydrogen, deuterium, methyl, isopropyl, $NO_2$, $SO_2CH_3$, $SCF_3$, $C_2F_5$, $OC_2F_5$, $OCH_3$, diphenylmethylsilyl, phenyl, methoxyphenyl, p-methylphenyl, 2,6-diisopropylphenyl, biphenyl, polyfluorophenyl, difluoropyridyl, nitrophenyl, dimethylthiazolyl, vinyl substituted by one or more of CN or $CF_3$, acetenyl substituted by one of CN or $CF_3$, dimethylphosphoroso, diphenylphosphoroso, F, $CF_3$, $OCF_3$, $SF_5$, $SO_2CF_3$, cyano, isocyano, SCN, OCN, trifluoromethylphenyl, trifluoromethoxyphenyl, bis(trifluoromethyl)phenyl, bis(trifluoromethoxy)phenyl, 4-cyanotetrafluorophenyl, phenyl or biphenyl substituted by one or more of F, CN or $CF_3$, tetrafluoropyridyl, pyrimidinyl, triazinyl, diphenylboranyl, oxaboraanthryl and combinations thereof.

According to an embodiment of the present disclosure, wherein L is, at each occurrence identically or differently, selected from the group consisting of the following structures:

L-1

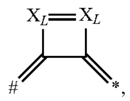

L-2

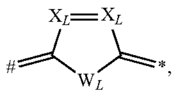

L-3

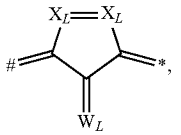

L-4

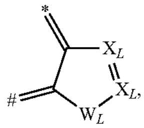

L-5

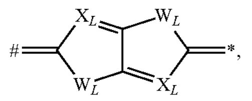

L-6

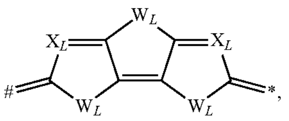

L-7

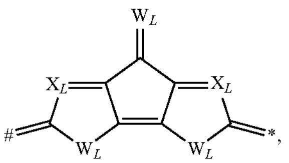

L-8

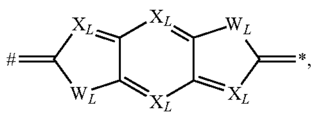

L-9

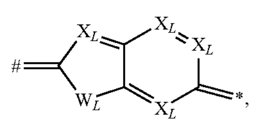

-continued

L-10

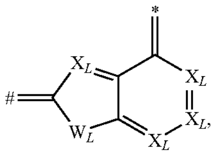

L-11

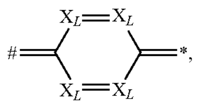

L-12

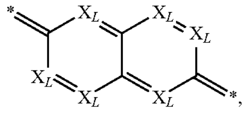

L-13

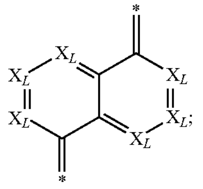

wherein $W_L$ is, at each occurrence identically or differently, selected from O, S, Se or $NR_N'$;

$X_L$ is, at each occurrence identically or differently, selected from $CR_L$ or N;

$R_L$ and $R_N'$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, a hydroxyl group, a sulfanyl group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted alkylgermanyl having 3 to 20 carbon atoms, substituted or unsubstituted arylgermanyl having 6 to 20 carbon atoms and combinations thereof;

"*" represents a position where Formula L-1 to Formula L-13 are connected to the group Yin Formula 1;

"#" represents a position where Formula L-1 to Formula L-13 are connected to the six-membered and five-membered conjugated ring comprising $X_1$ to $X_3$ and W in Formula 1; and adjacent substituents $R_L$ and $R_N'$ can be optionally joined to form a ring.

In this embodiment, the expression that "adjacent substituents $R_L$ and $R_N'$ can be optionally joined to form a ring" is intended to mean that any one or more of any two adjacent substituents among the substituents $R_L$ and $R_N'$, such as two $R_L$, and $R_L$ and $R_N'$, can be optionally joined to form a ring. Obviously, it is possible that these adjacent substituents $R_L$ and $R_N'$ are not joined to form a ring.

According to an embodiment of the present disclosure, wherein L is, at each occurrence identically or differently, selected from L-2, L-11 or L-12.

According to an embodiment of the present disclosure, wherein the compound has a structure represented by any one of Formula F1 to Formula F10:

F1

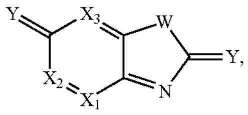

F2

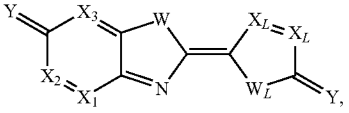

F3

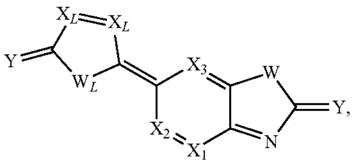

F4

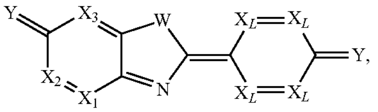

F5

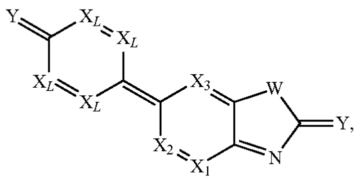

F6

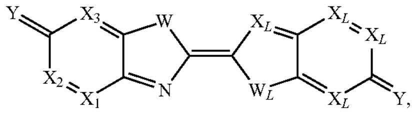

F7

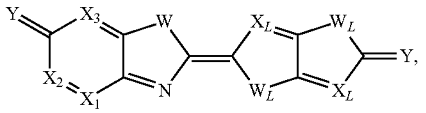

F8

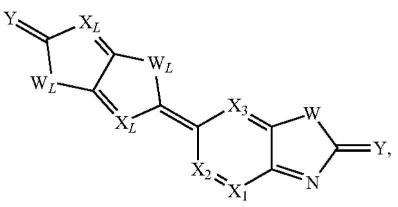

-continued

F9

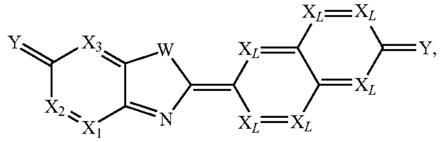

F10

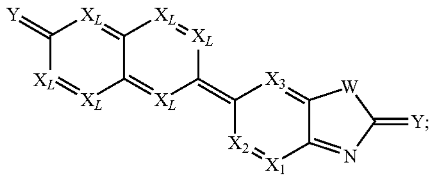

wherein

Y is, at each occurrence identically or differently, selected from O, S, Se, CR"R"' or NR';

W is, at each occurrence identically or differently, selected from O, S, Se or $NR_N$;

$X_1$ to $X_3$ are, at each occurrence identically or differently, selected from CR or N;

$W_L$ is, at each occurrence identically or differently, selected from O, S, Se or $NR_N'$;

$X_L$ is, at each occurrence identically or differently, selected from $CR_L$ or N;

R, $R_N$, $R_L$, R', R", R"' and $R_N'$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted alkylgermanyl having 3 to 20 carbon atoms, substituted or unsubstituted arylgermanyl having 6 to 20 carbon atoms and combinations thereof;

at least one of R, $R_N$, R', R" and R"' is a group having at least one electron-withdrawing group; and adjacent substituents R, $R_N$, $R_L$, R', R", R"' and $R_N'$ can be optionally joined to form a ring.

In this embodiment, the expression that "adjacent substituents R, $R_N$, $R_L$, R', R", R"' and $R_N'$ can be optionally joined to form a ring" is intended to mean that any one or more of any two adjacent substituents among the substituents R, $R_N$, $R_L$, R', R", R"' and $R_N'$, such as two R, two $R_L$, R and $R_N$, R" and R"', and $R_L$ and $R_N'$, can be optionally joined to form a ring. Obviously, it is possible that these adjacent substituents R, $R_N$, $R_L$, R', R", R"' and $R_N'$ are not joined to form a ring.

According to an embodiment of the present disclosure, wherein R, $R_L$, $R_N$ and $R_N'$ are, at each occurrence identically or differently, selected from the group consisting of the following structures:
B1
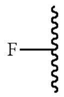
B2
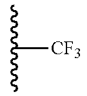
B3
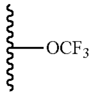
B4
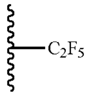
B5
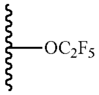
B6
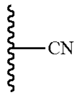
B7
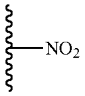
B8
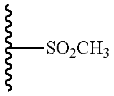
B9
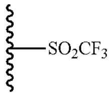
B10
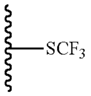
B11
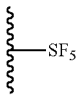
B12
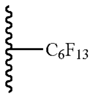
B13
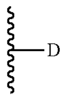
-continued
B14
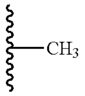
B15
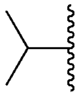
B16
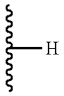
B17
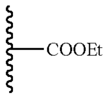
B18
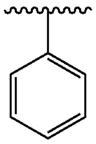
B19
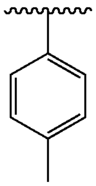
B20
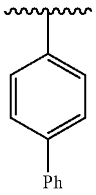
B21
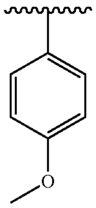
B22
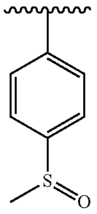

-continued
B23
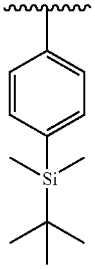
B24
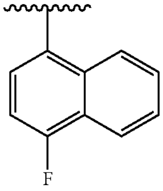
B25
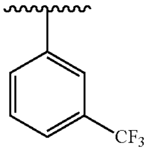
B26
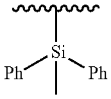
B27
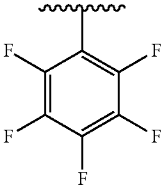
B28
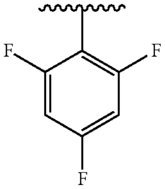
B29
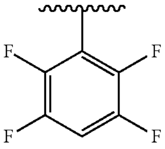
B30
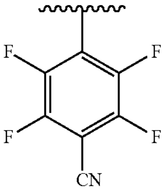
-continued
B31
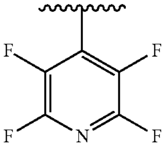
B32
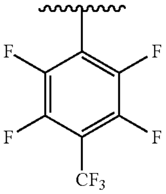
B33
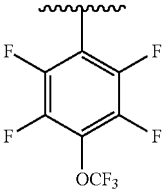
B34
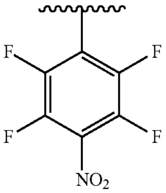
B35
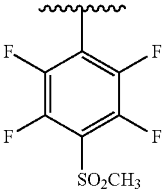
B36
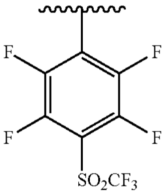
B37
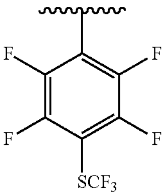
B38
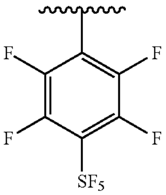

-continued
B39
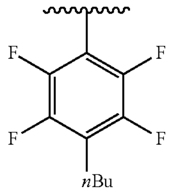
B40
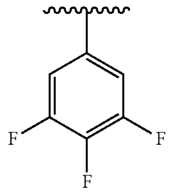
B41
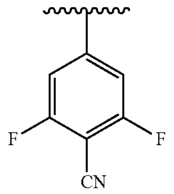
B42
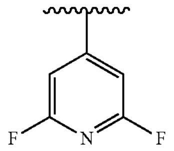
B43
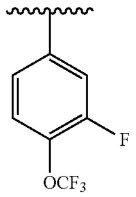
B44
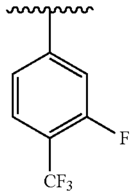
B45
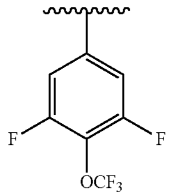
B46
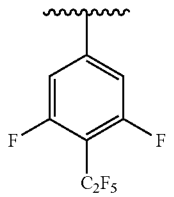
-continued
B47
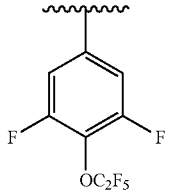
B48
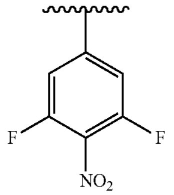
B49
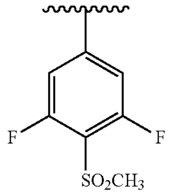
B50
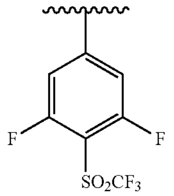
B51
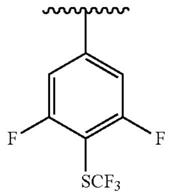
B52
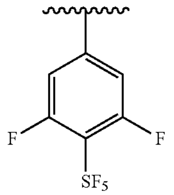
B53
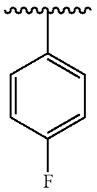
B54
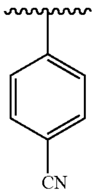

-continued
B55
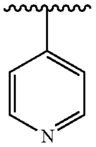
B56
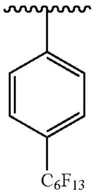
B57
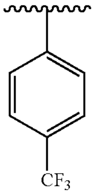
B58
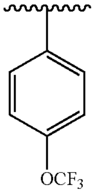
B59
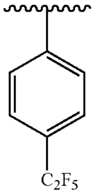
B60
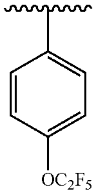
B61
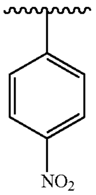
B62
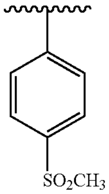
-continued
B63
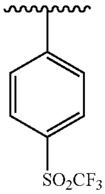
B64
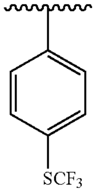
B65
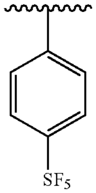
B66
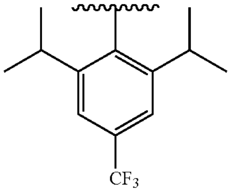
B67
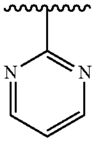
B68
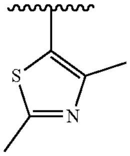
B69
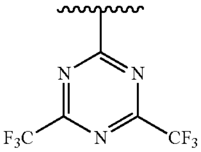
B70
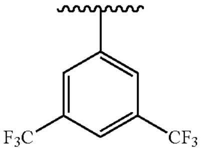
B71
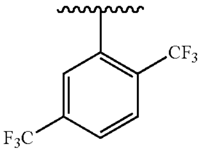

-continued
B72
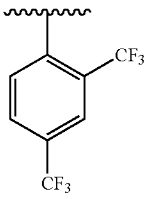
B73
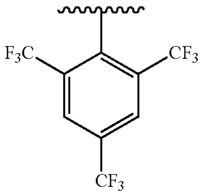
B74
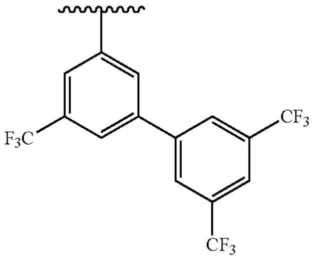
B75
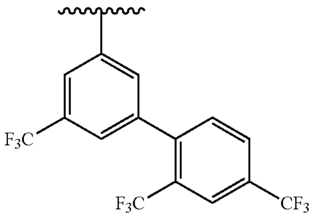
B76
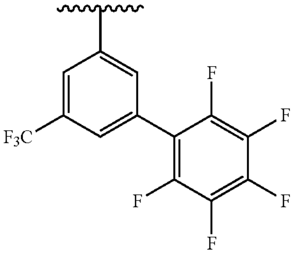
B77
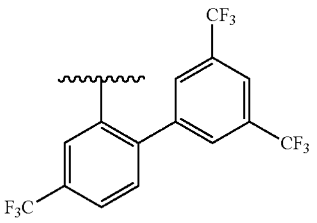
B78
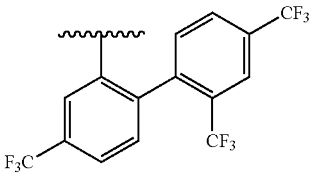
-continued
B79
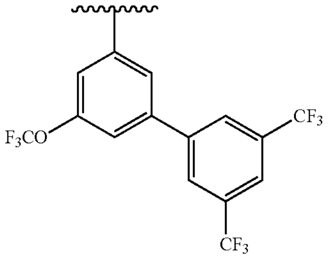
B80
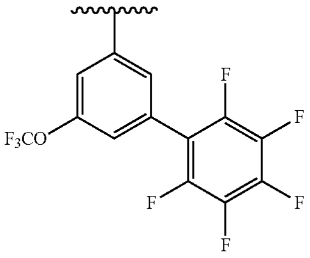
B81
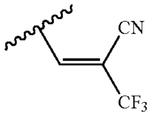
B82
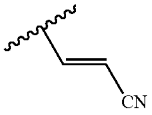
B83
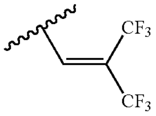
B84
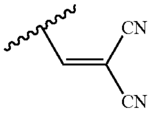
B85
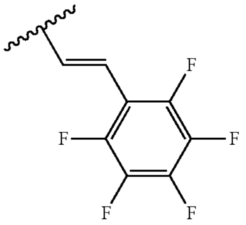
B86
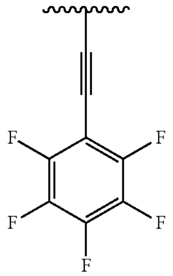

-continued
B87
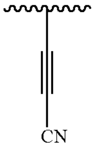
B88
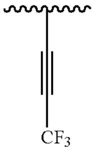
B89
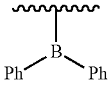
B90
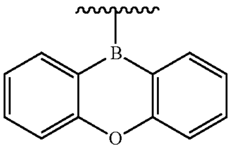
B91
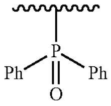
B92
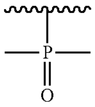
B93
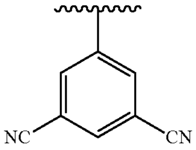
B94
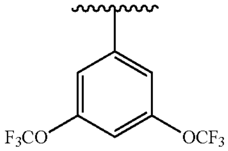
B95
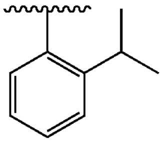
B96
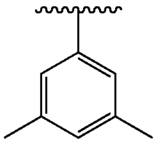
-continued
B97
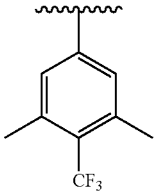
B98
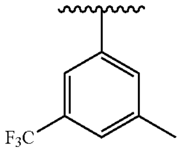
B99
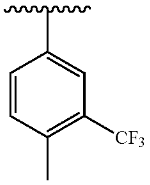
B100
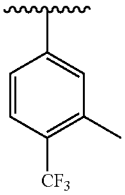
B101
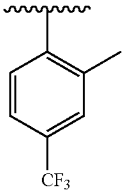
B102
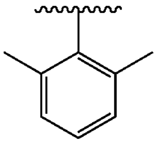
B103
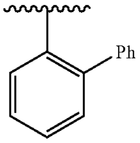
B104
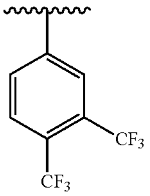

-continued
B105
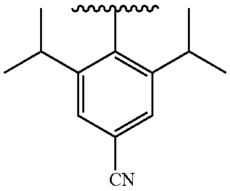
B106
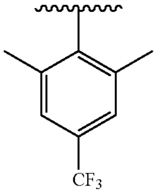
B107
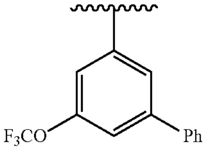
B108
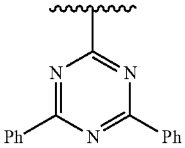
B109
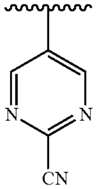
B110
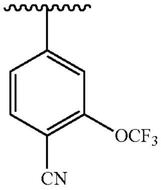
B111
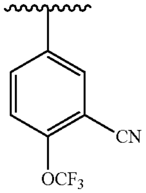
B112
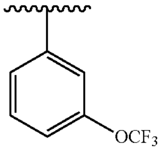
-continued
B113
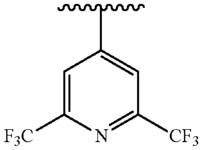
B114
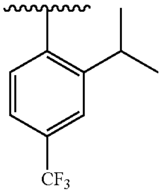
B115
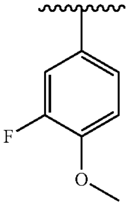
B116
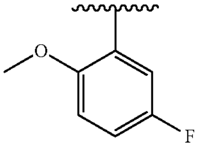
B117
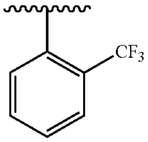
B118
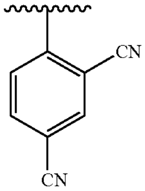
B119
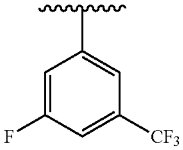
B120
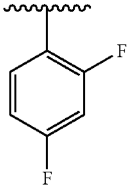
B121
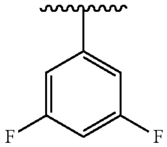

-continued

B122

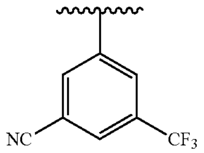

B123

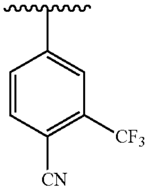

B124

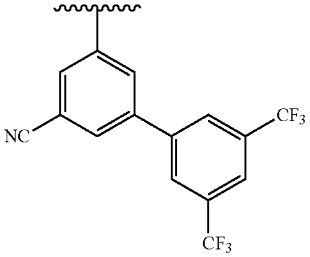

wherein “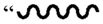” represents a position where the group R having the above structure is connected to the six-membered ring comprising $X_1$ to $X_3$ in Formula 1, or represents a position where the group $R_L$ having the above structure is connected to the group L, or represents a position where $R_N$ is connected to N when W is selected from $NR_N$, or represents a position where $R_N'$ is connected to N when $W_L$ is selected from $NR_N'$.

According to an embodiment of the present disclosure, wherein the compound is selected from the group consisting of Compound F1-1 to Compound F1-436, Compound F2-1 to Compound F2-160, Compound F3-1 to Compound F3-160, Compound F4-1 to Compound F4-96, Compound F5-1 to Compound F5-96, Compound F6-1 to Compound F6-96 and Compound F7-1 to Compound F7-96; wherein for the specific structures of Compound F1-1 to Compound F1-436, Compound F2-1 to Compound F2-160, Compound F3-1 to Compound F3-160, Compound F4-1 to Compound F4-96, Compound F5-1 to Compound F5-96, Compound F6-1 to Compound F6-96 and Compound F7-1 to Compound F7-96, referred to claim 14.

In this embodiment, Compound F1-1 has a structure represented by Formula F1:

F1

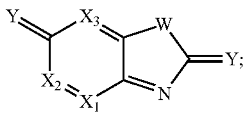

wherein two Y are the same, and both are A1

A1

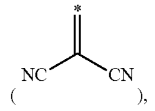

$X_1$ is C-B1 (C represents a carbon atom, and B1 is

B1

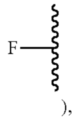

$X_2$ and $X_3$ are C-B16 (C represents a carbon atom, and B16 is

B16

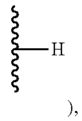

and W is O. That is, the structure of Compound F1-1 is

F1-1

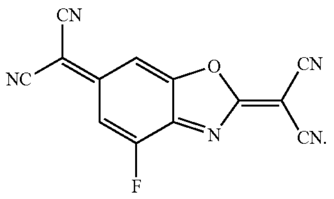

Similarly, the structure of any other compound in this embodiment may be clearly known.

According to an embodiment of the present disclosure, further disclosed is an electroluminescent device comprising an anode, a cathode and an organic layer disposed between the anode and the cathode, wherein the organic layer comprises the compound in any one of the preceding embodiments.

According to an embodiment of the present disclosure, wherein the organic layer is a hole injection layer or a hole transporting layer, and the hole injection layer or the hole transporting layer is formed by the compound alone.

According to an embodiment of the present disclosure, wherein the organic layer is a hole injection layer or a hole transporting layer, wherein the hole injection layer or the hole transporting layer further comprises at least one hole transporting material; wherein a molar doping ratio of the compound to the hole transporting material is 10000:1 to 1:10000.

According to an embodiment of the present disclosure, wherein the organic layer is a hole injection layer or a hole transporting layer, which further comprises at least one hole transporting material; wherein a molar doping ratio of the compound to the hole transporting material is 10:1 to 1:100.

According to an embodiment of the present disclosure, wherein the electroluminescent device comprises at least two emissive units and the organic layer is a charge generation layer and disposed between the at least two emissive units, wherein the charge generation layer comprises a p-type charge generation layer and an n-type charge generation layer.

According to an embodiment of the present disclosure, wherein the p-type charge generation layer comprises the compound.

According to an embodiment of the present disclosure, wherein the p-type charge generation layer further comprises at least one hole transporting material, wherein a molar doping ratio of the compound to the hole transporting material is 10000:1 to 1:10000.

According to an embodiment of the present disclosure, wherein the p-type charge generation layer further comprises at least one hole transporting material, wherein a molar doping ratio of the compound to the hole transporting material is 10:1 to 1:100.

According to an embodiment of the present disclosure, wherein the hole transporting material comprises a compound having a triarylamine unit, a spirobifluorene compound, a pentacene compound, an oligothiophene compound, an oligomeric phenyl compound, an oligomeric phenylene vinyl compound, an oligofluorene compound, a porphyrin complex or a metallic phthalocyanine complex.

According to an embodiment of the present disclosure, wherein the charge generation layer further comprises a buffer layer disposed between the p-type charge generation layer and the n-type charge generation layer, and the buffer layer also comprises the compound.

According to an embodiment of the present disclosure, the electroluminescent device is prepared by a vacuum evaporation method.

According to an embodiment of the present disclosure, further disclosed is a compound combination comprising the compound in any one of the preceding embodiments.

Combination with Other Materials

The materials described in the present disclosure for a particular layer in an organic light emitting device can be used in combination with various other materials present in the device. The combinations of these materials are described in more detail in U.S. Pat. App. No. 20160359122 at paragraphs 0132-0161, which is incorporated by reference herein in its entirety. The materials described or referred to the disclosure are non-limiting examples of materials that may be useful in combination with the compounds disclosed herein, and one of skill in the art can readily consult the literature to identify other materials that may be useful in combination.

The materials described herein as useful for a particular layer in an organic light emitting device may be used in combination with a variety of other materials present in the device. For example, the compounds disclosed herein may be used in combination with a wide variety of emissive dopants, hosts, transport layers, blocking layers, injection layers, electrodes and other layers that may be present. The combination of these materials is described in detail in paragraphs 0080-0101 of U.S. Pat. App. No. 20150349273, which is incorporated by reference herein in its entirety. The materials described or referred to the disclosure are non-limiting examples of materials that may be useful in combination with the compounds disclosed herein, and one of skill in the art can readily consult the literature to identify other materials that may be useful in combination.

An organic light-emitting device described in the present disclosure may include a hole injection layer, a hole transporting layer, an electron blocking layer, an emissive layer, a hole blocking layer, an electron transporting layer and an electron injection layer. The emissive layer comprises at least a light-emitting dopant and at least one host compound. The light-emitting dopant may be a fluorescent light-emitting dopant, a delayed fluorescent light-emitting dopant and/or a phosphorescent light-emitting dopant. FIG. 1 schematically shows an organic light-emitting apparatus 100 without limitation. Apparatus 100 may be fabricated by depositing the layers described in order. The properties and functions of the layers and example materials are described in more detail in U.S. Pat. No. 7,279,704 at cols. 6-10, the disclosure of which is incorporated herein by reference in its entirety.

Conventional hole transporting materials in the related art may be used in the hole transporting layer. For example, the hole transporting layer may typically include the following hole transporting materials without limitation:

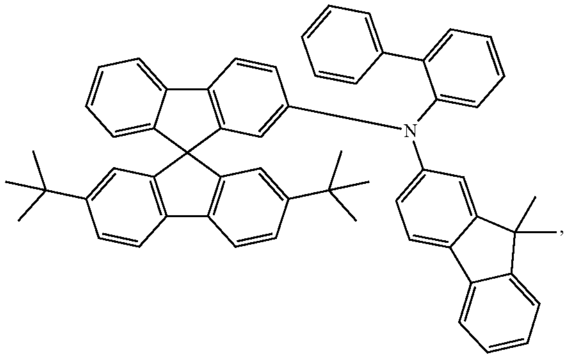
,

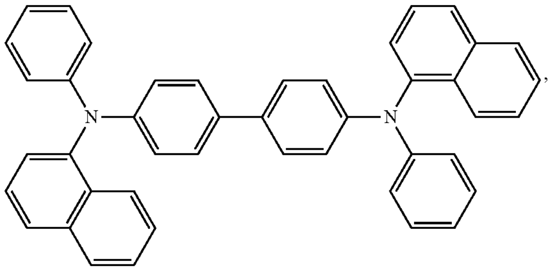
,

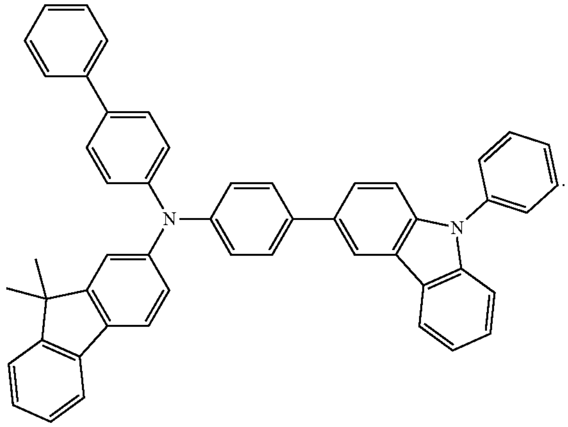
.

Conventional electron transporting materials in the related art may be used in the electron transporting layer. For example, the electron transporting layer may typically include the following electron transporting materials without limitation:

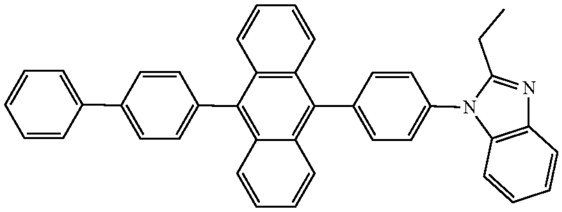
,
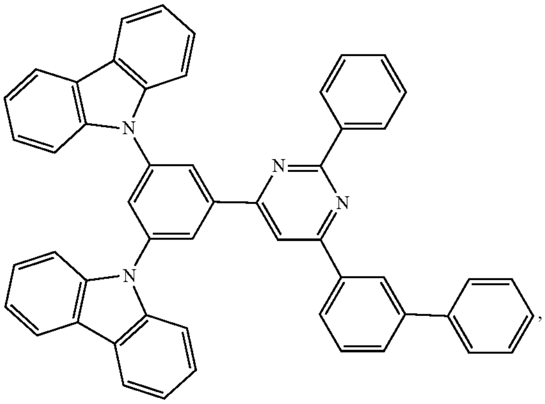
,
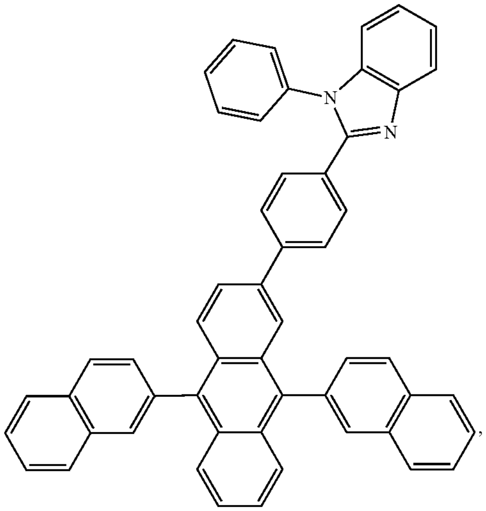
,
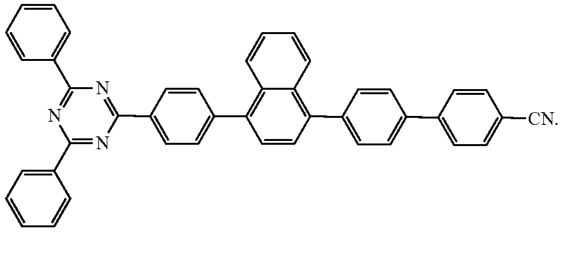
Conventional light-emitting materials and host materials in the related art may be used in the emissive layer. For example, the emissive layer may typically include the following fluorescent light-emitting materials, delayed fluorescence light-emitting materials, fluorescent host materials and delayed fluorescence host materials without limitation:
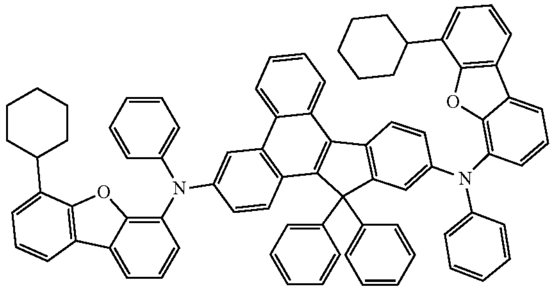
,
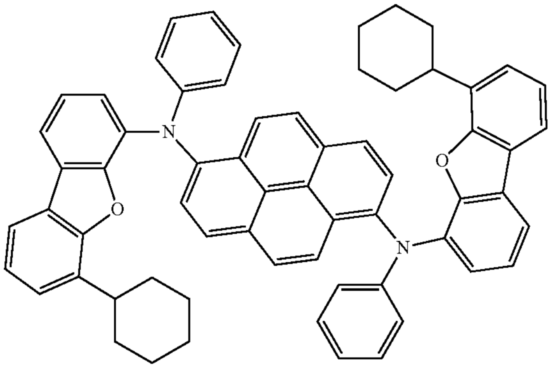
,
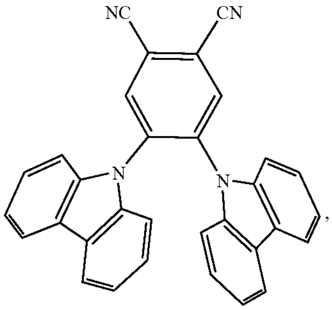
,
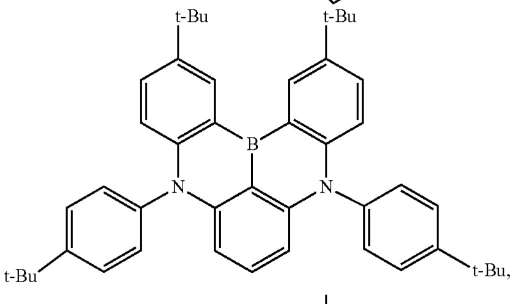
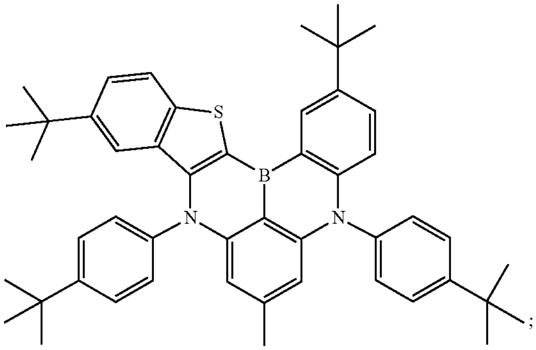
;

-continued
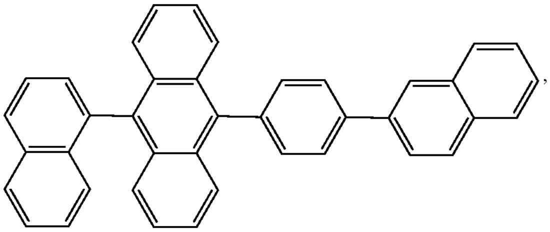
,
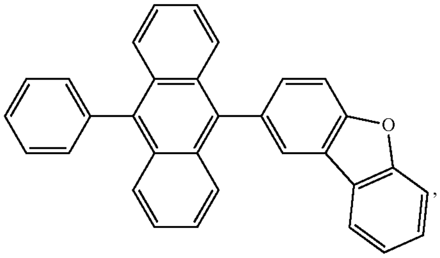
,
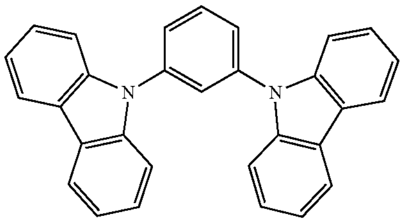
,
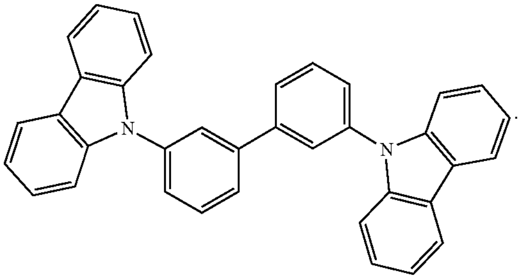
.
The emissive layer may also typically include the following phosphorescent light-emitting materials and phosphorescent host materials without limitation:
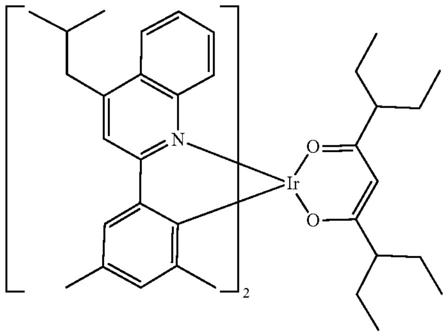
,
-continued
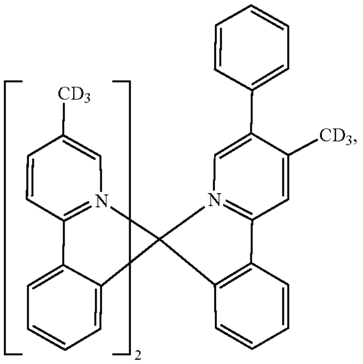
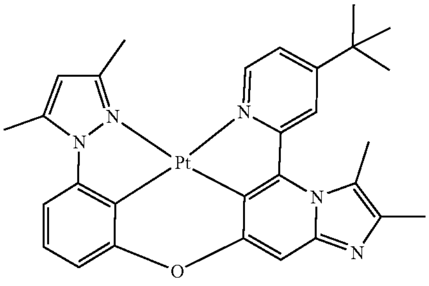
,
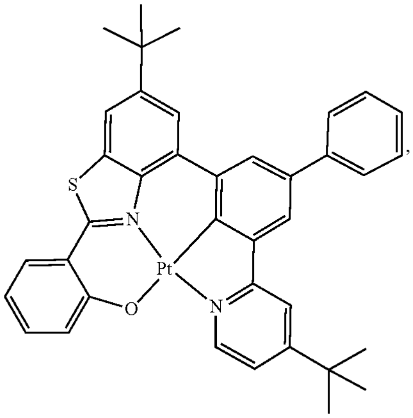
,
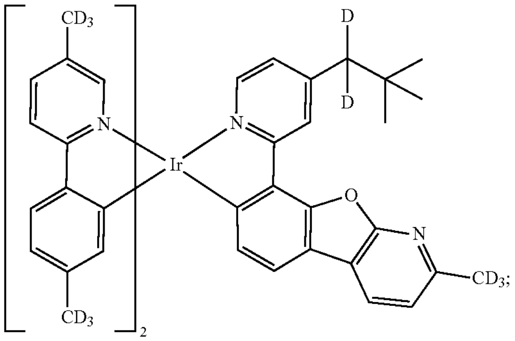
;

-continued

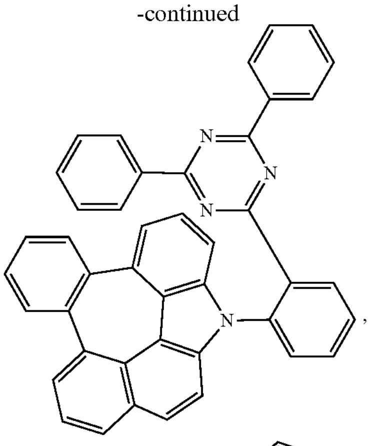

,

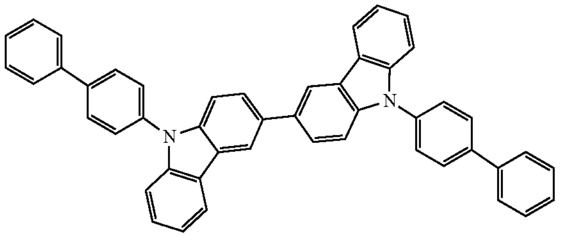

.

Conventional electron blocking materials in the related art may be used in the electron blocking layer. For example, the electron blocking layer may typically include the following electron blocking materials without limitation:

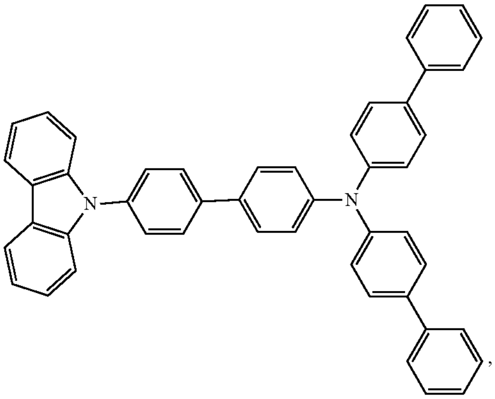

,

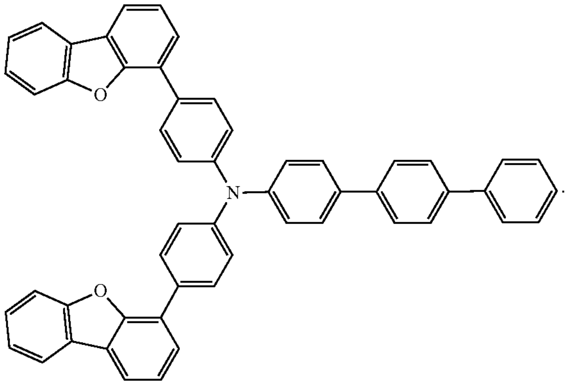

.

In the embodiments of material synthesis, all reactions were performed under nitrogen protection unless otherwise stated. All reaction solvents were anhydrous and used as received from commercial sources. Synthetic products were structurally confirmed and tested for properties using one or more conventional equipment in the art (including, but not limited to, nuclear magnetic resonance instrument produced by BRUKER, liquid chromatograph produced by SHIMADZU, liquid chromatograph-mass spectrometry produced by SHIMADZU, gas chromatograph-mass spectrometry produced by SHIMADZU, differential Scanning calorimeters produced by SHIMADZU, fluorescence spectrophotometer produced by SHANGHAI LENGGUANG TECH., electrochemical workstation produced by WUHAN CORRTEST, and sublimation apparatus produced by ANHUI BEQ, etc.) by methods well known to the persons skilled in the art. In the embodiments of the device, the characteristics of the device were also tested using conventional equipment in the art (including, but not limited to, evaporator produced by ANGSTROM ENGINEERING, optical testing system produced by SUZHOU FATAR, life testing system produced by SUZHOU FATAR, and ellipsometer produced by BEIJING ELLITOP, etc.) by methods well known to the persons skilled in the art. As the persons skilled in the art are aware of the above-mentioned equipment use, test methods and other related contents, the inherent data of the sample can be obtained with certainty and without influence, so the above related contents are not further described in this present disclosure.

MATERIAL SYNTHESIS EXAMPLE

The method for preparing a compound in the present disclosure is not limited herein. Typically, the following compounds are used as examples without limitation, and synthesis routes and preparation methods thereof are described below.

Synthesis Example 1: Synthesis of Compound F1-194

Step 1: Synthesis of Intermediate F1-194-A

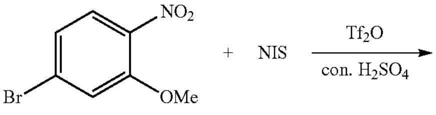

SM1

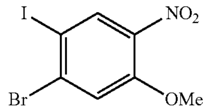

F1-194-A

In a 2 L two-necked round-bottom flask, 500 mL of concentrated sulfuric acid, trifluoromethanesulfonic anhydride ($Tf_2O$) (4.86 g, 17.2 mmol) and N-iodosuccinimide (NIS) (20.37 g, 90.5 mmol) were added in sequence under a nitrogen atmosphere and reacted for 30 min at room temperature. Then, SM1 (40 g, 172.4 mmol) was added and reacted for 30 min. NIS (20.37 g, 90.5 mmol) was added again and reacted for 1 h at room temperature. After GCMS showed that the reaction was completed, the reaction solution was slowly poured into ice water, a saturated $Na_2SO_3$ solution was added until a solid was precipitated, and the solid was filtered then dissolved with dichloromethane. The organic phase was washed with an aqueous solution of sodium sulfite and an aqueous solution of sodium bicarbonate, dried over anhydrous magnesium sulfate, concentrated, crystallized from dichloromethane and n-heptane, and filtered to obtain Intermediate F1-194-A (37.3 g, with a yield of 60%).

Step 2: Synthesis of Intermediate F1-194-B

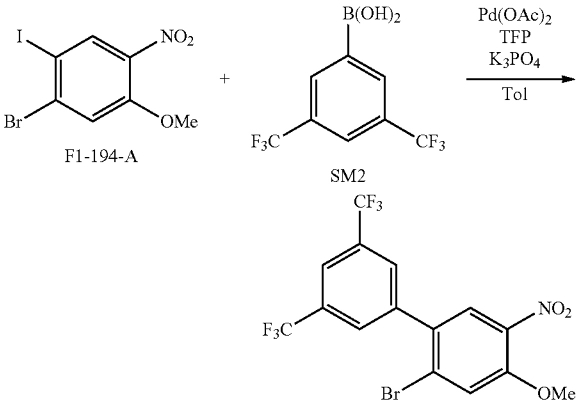

F1-194-A

SM2

F1-194-B

In a 2 L two-necked round-bottom flask, F1-194-A (24.5 g, 68.45 mmol), potassium phosphate (29.06 g, 136.9 mmol), SM2 (20.83 g, 80.77 mmol), $Pd(OAc)_2$ (0.63 g, 0.68 mmol), tris(2-furyl)phosphine (TFP) (0.8 g, 3.42 mmol) and 850 mL of toluene were added in sequence under a nitrogen atmosphere, heated to 115° C. and reacted overnight. After GCMS showed that the reaction was completed, the reaction solution was cooled to room temperature, filtered through Celite, concentrated, and purified through column chromatography to obtain a white solid F1-194-B (26 g, with a yield of 85.5%).

Step 3: Synthesis of Intermediate F1-194-C

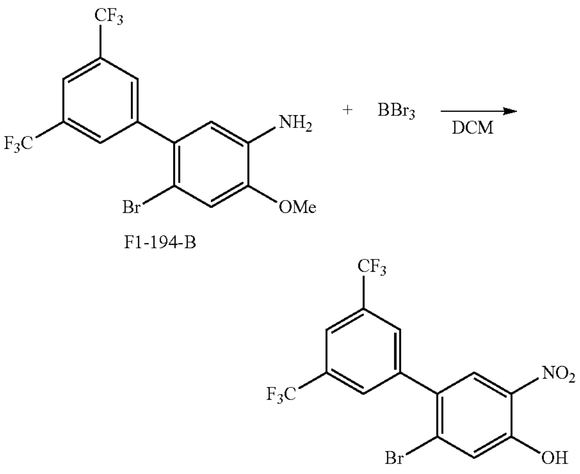

F1-194-B

F1-194-C

In a 2 L two-necked round-bottom flask, F1-194-B (26 g, 58.5 mmol) and 1 L of dichloromethane were added under a nitrogen atmosphere and cooled to 0° C. Then, $BBr_3$ (8 mL, 70.3 mmol) was added dropwise, heated to room temperature and reacted for 1 h. After TLC showed that the reaction was completed, the reaction solution was slowly poured into ice water, extracted with dichloromethane, dried over anhydrous magnesium sulfate, and concentrated to obtain crude F1-194-C, which was directly used in the next step without further purification.

Step 4: Synthesis of Intermediate F1-194-D

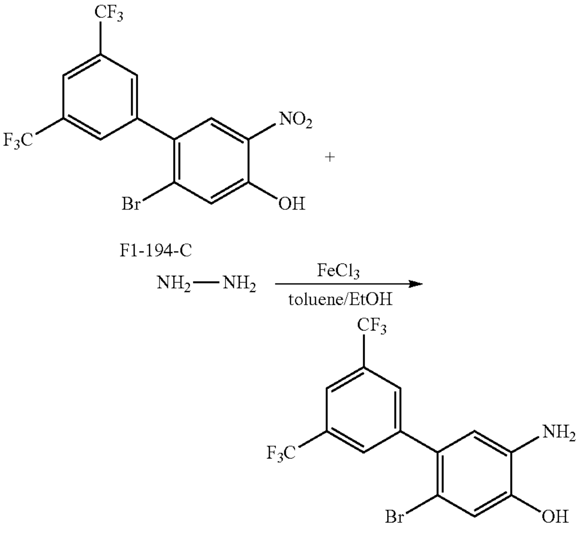

F1-194-C

F1-194-D

In a 1 L two-necked round-bottom flask, F1-194-C, $FeCl_3$ (1.03 g, 6.3 mmol), activated carbon (0.38 g, 31.52 mmol), 200 mL of toluene and 200 mL of absolute ethanol were added under a nitrogen atmosphere and heated to 80° C. Hydrazine hydrate (40 mL, 378.3 mmol) was slowly added dropwise over 3 h and reacted for 2 h at 80° C. After TLC showed that the reaction was completed, the reaction solution was cooled to room temperature, filtered through Celite and concentrated to obtain a crude product F1-194-D as an oil (27 g), which was directly used in the next step without further purification.

Step 5: Synthesis of Intermediate F1-194-E

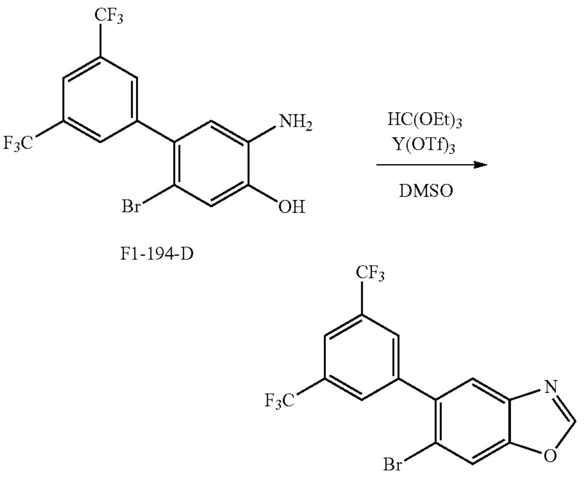

F1-194-D

F1-194-E

In a 1 L two-necked round-bottom flask, F1-194-D (27 g, 67.5 mmol), yttrium trifluoromethane sulfonate ($Y(OTf)_3$)

(1.81 g, 3.37 mmol), triethyl orthoformate ($HC(OEt)_3$) (30 g, 202.4 mmol) and 340 mL of DMSO were added in sequence under a nitrogen atmosphere, heated to 120° C. and reacted for 2 h. After TLC showed that the reaction was completed, the reaction solution was cooled to room temperature, slowly poured into ice water, extracted with dichloromethane, concentrated, and purified through column chromatography to obtain F1-194-E (20 g, with a yield of 71.9% over three steps).

Step 6: Synthesis of Intermediate F1-194-F

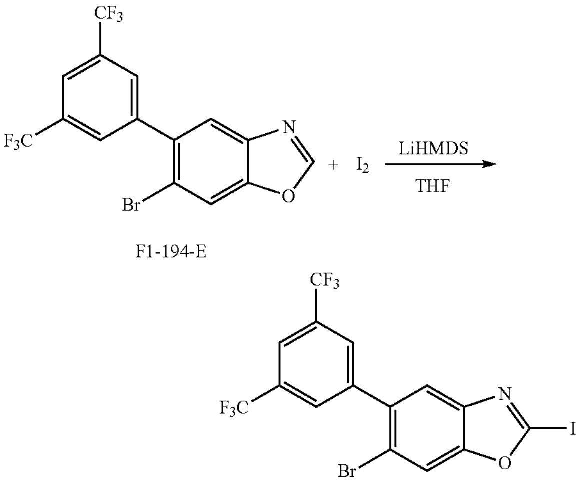

F1-194-E

F1-194-F

In a 500 mL three-necked round-bottom flask, F1-194-E (9 g, 21.9 mmol) and 220 mL of THF were added in sequence under a nitrogen atmosphere and cooled to −30° C., lithium bis(trimethylsilyl)amide (LiHMDS) (23 mL, 23 mmol) was slowly added dropwise and reacted at −30° C. for 30 min, and then $I_2$ (8.4 g, 32.9 mmol) was added, heated to room temperature and reacted for 30 min. After HPLC showed that the reaction was completed, a saturated aqueous solution of sodium sulfite was added to quench the reaction, extracted with dichloromethane, concentrated and purified through column chromatography to obtain a white solid F1-194-F (8 g, with a yield of 68%).

Step 7: Synthesis of Intermediate F1-194-G

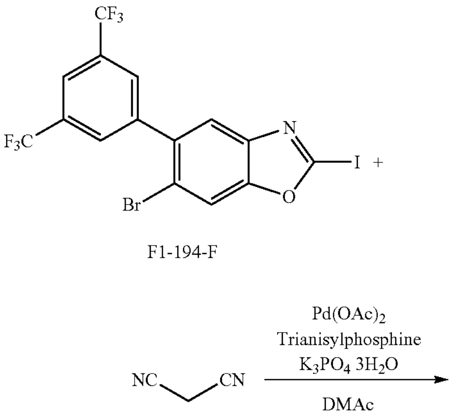

F1-194-F

-continued

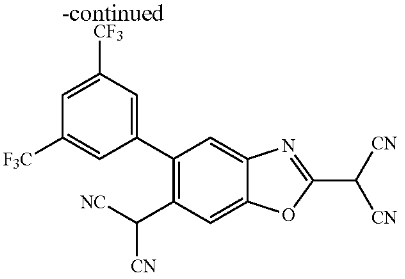

F1-194-G

In a 500 mL two-necked round-bottom flask, F1-194-F (5.7 g, 10.65 mmol), potassium phosphate trihydrate (17.0 g, 64 mmol), malononitrile (2.11 g, 32 mmol), $Pd(OAc)_2$ (72 mg, 0.32 mmol), trianisylphosphine (259 mg, 0.852 mmol) and 200 mL of N,N-dimethylacetamide (DMAc) were added in sequence under a nitrogen atmosphere, heated to 130° C. and reacted for 36 h. After HPLC showed that the reaction was completed, the reaction solution was slowly poured into dilute hydrochloric acid to precipitate a large amount of yellow solids as a crude product. The crude product was recrystallized from a proper amount of acetone to obtain a white solid F1-194-G (4.8 g, with a yield of 98%).

Step 8: Synthesis of Compound F1-194

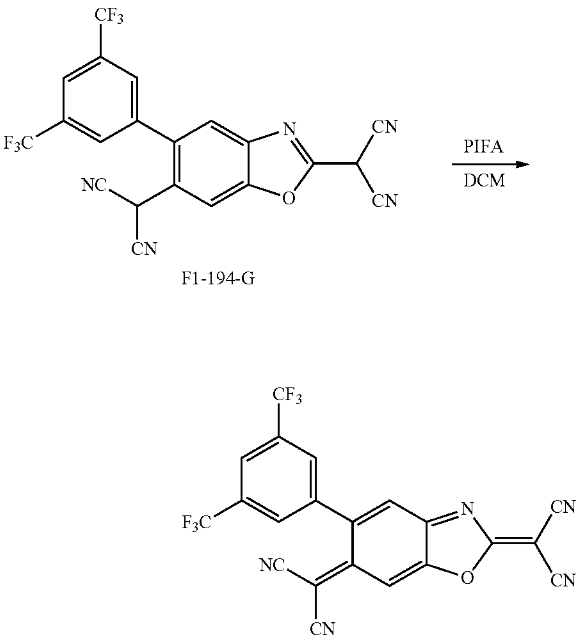

F1-194-G

F1-194

In a 2 L two-necked round-bottom flask, F1-194-G (4.8 g, 10.45 mmol) and 1 L of dichloromethane were added in sequence under a nitrogen atmosphere, and bis(trifluoroacetoxy)iodobenzene (PIFA) (9 g, 20.9 mmol) was added in batches, reacted for 5 days at room temperature and concentrated to a proper volume. Then, n-hexane was added, and the resultant was filtrated to obtain a purple black solid F1-194 (1.7 g, with a yield of 35%). The product was confirmed as the target product with a molecular weight of 457.

Synthesis Example 2: Synthesis of Compound F1-248

Step 1: Synthesis of Intermediate F1-248-L1

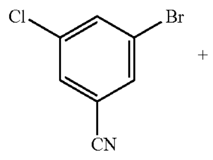

SM3

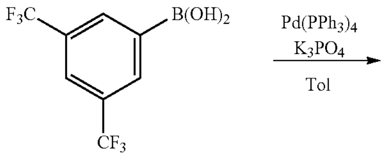

SM4

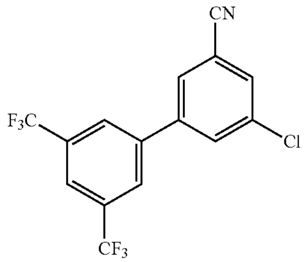

F1-248-L1

In a 2 L two-necked round-bottom flask, SM3 (24.5 g, 68.45 mmol), potassium phosphate (49.06 g, 231 mmol), SM4 (38.8 g, 150.5 mmol), $Pd(PPh_3)_4$ (2.66 g, 2.31 mmol) and 1 L of toluene were added in sequence under a nitrogen atmosphere, heated to 110° C. and reacted overnight. After GCMS showed that the reaction was completed, the reaction solution was cooled to room temperature, filtered through Celite, concentrated and purified through column chromatography to obtain a white solid F1-248-L1 (32 g, with a yield of 80%).

Step 2: Synthesis of Intermediate F1-248-L2

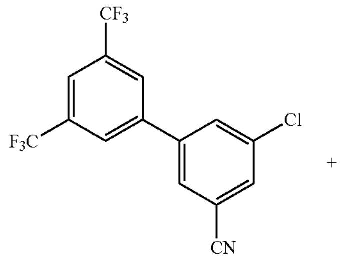

F1-248-L1

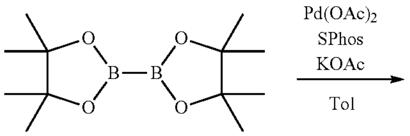

-continued

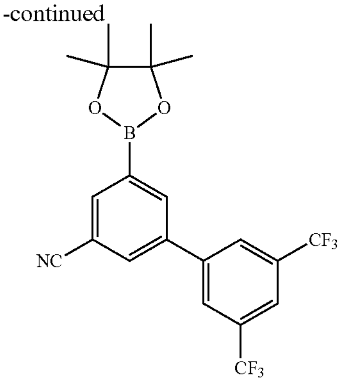

F1-248-L2

In a 2 L two-necked round-bottom flask, F1-248-L1 (31.7 g, 90.8 mmol), bis(pinacolato)diboron ($B_2Pin_2$) (25.4 g, 100 mmol), potassium acetate (17.8 g, 182 mmol), $Pd(OAc)_2$ (203 mg, 0.908 mmol), dicyclohexyl(2',6'-dimethoxy-[1,1'-biphenyl]-2-yl)phosphine (SPhos) (1.17 g, 2.724 mmol) and 900 mL of toluene were added in sequence under a nitrogen atmosphere, heated to 100° C. and reacted overnight. After GCMS showed that the reaction was completed, the reaction solution was cooled to room temperature, filtered through Celite, concentrated and purified through column chromatography to obtain a white solid F1-248-L2 (25 g, with a yield of 63%).

Step 3: Synthesis of Intermediate F1-248-B

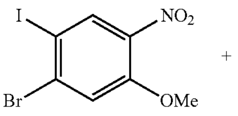

F1-194-A

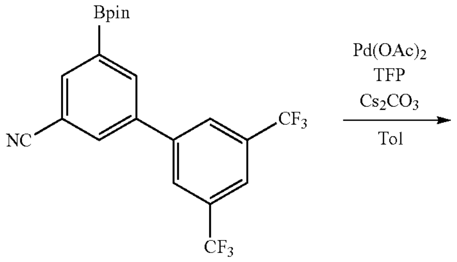

F1-248-L2

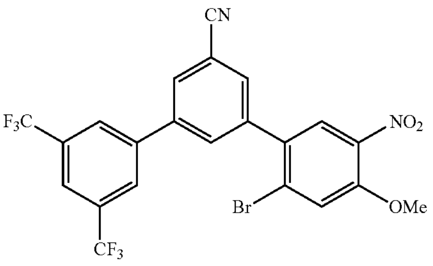

F1-248-B

In a 2 L two-necked round-bottom flask, F1-194-A (19.3 g, 54 mmol), F1-248-L2 (23.6 g, 53.5 mmol), palladium acetate (121.5 mg, 0.54 mmol), TFP (376 mg, 1.62 mmol), cesium carbonate (35.2 g, 108 mmol) and 1 L of toluene were added in sequence under a nitrogen atmosphere, heated to 110° C. and reacted overnight. After GCMS showed that the reaction was completed, the reaction solution was cooled to room temperature, filtered through Celite, concentrated and purified through column chromatography to obtain a white solid F1-248-B (16 g, with a yield of 54%).

Step 4: Synthesis of Intermediate F1-248-C

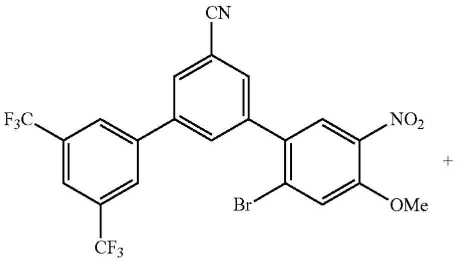

F1-248-B

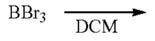

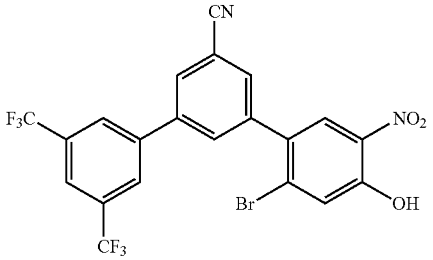

F1-248-C

In a 2 L two-necked round-bottom flask, F1-248-B (16 g, 29.4 mmol) and 600 mL of dichloromethane were added under a nitrogen atmosphere and cooled to 0° C. Then, $BBr_3$ (3.62 mL, 38.2 mmol) was added dropwise and reacted for 1 h at room temperature. After TLC showed that the reaction was completed, the reaction solution was slowly poured into ice water and extracted with dichloromethane, and organic phases were combined, dried over anhydrous magnesium sulfate, and concentrated to obtain F1-248-C, which was directly used in the next step without further purification.

Step 5: Synthesis of Intermediate F1-248-D

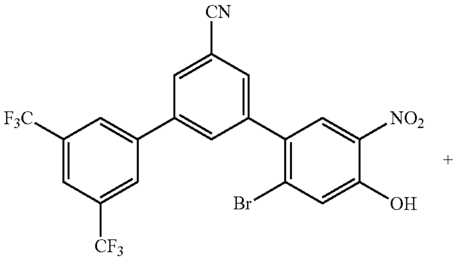

F1-248-C

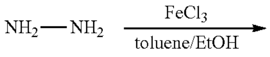

-continued

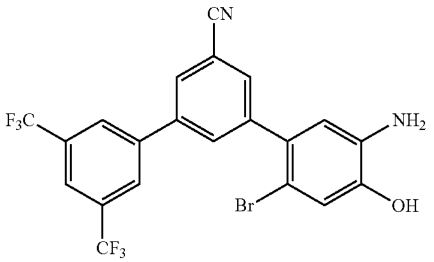

F1-248-D

In a 1 L two-necked round-bottom flask, F1-248-C, $FeCl_3$ (292 mg, 1.8 mmol), activated carbon (180 mg, 15 mmol), 150 mL of toluene and 150 mL of absolute ethanol were added under a nitrogen atmosphere, and hydrazine hydrate (15 g, 150 mmol) was added, heated to 75° C. and reacted for 2 h. After TLC showed that the reaction was completed, the reaction solution was cooled to room temperature and filtered through Celite. The filtrate was concentrated to obtain crude F1-248-D, which was directly used in the next step without further purification.

Step 6: Synthesis of Intermediate F1-248-E

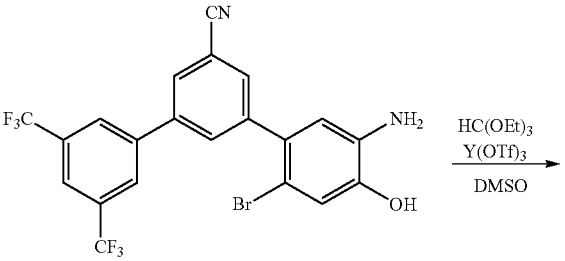

F1-248-D

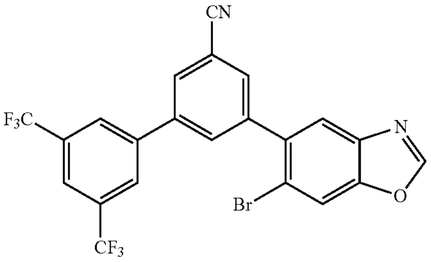

F1-248-E

In a 1 L two-necked round-bottom flask, F1-248-D, $Y(OTf)_3$ (482 mg, 0.88 mmol), 150 mL of DMSO and $HC(OEt)_3$ (17.70 g, 120 mmol) were added in sequence under a nitrogen atmosphere, heated to 120° C. and reacted for 2 h. After TLC showed that the reaction was completed, the reaction solution was cooled to room temperature and slowly poured into ice water to precipitate a large amount of solids. The solids were filtered and crystallized from petroleum ether and dichloromethane to obtain a yellow solid F1-248-E (11.20 g, with a total yield of 73% over three steps).

Step 7: Synthesis of Intermediate F1-248-F

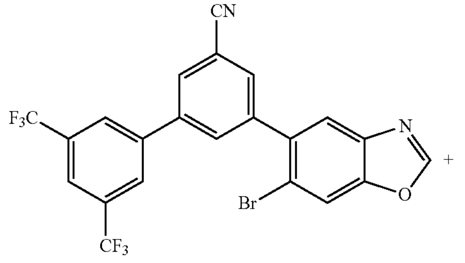

F1-248-E

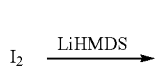

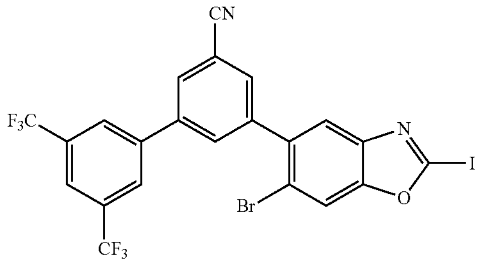

F1-248-F

In a 500 mL two-necked round-bottom flask, F1-248-E (9 g, 21.9 mmol) and 250 mL of THF were added in sequence under a nitrogen atmosphere and cooled to −30° C., LiHMDS (26.2 mL, 26.2 mmol) was added dropwise and reacted at −30° C. for 1 h, and then $I_2$ (9.07 g, 35.7 mmol) was added, heated to room temperature and reacted for 30 min. After HPLC showed that the reaction was completed, a saturated $Na_2SO_3$ solution was added to quench the reaction, extracted with dichloromethane, concentrated and purified through column chromatography to obtain a white solid F1-248-F (12 g, with a yield of 80%).

Step 8: Synthesis of Intermediate F1-248-G

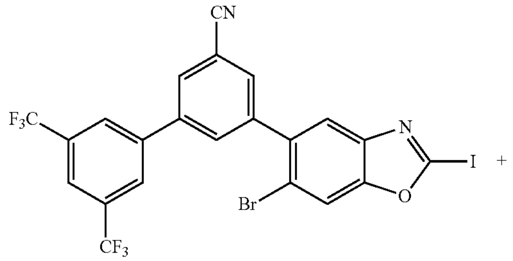

F1-248-F

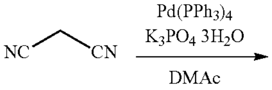

-continued

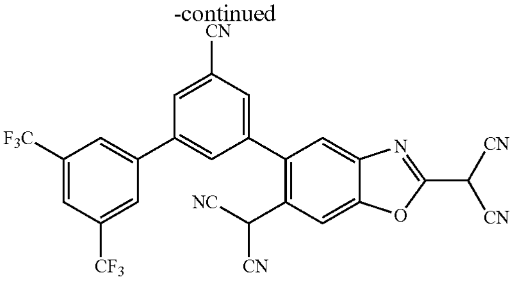

F1-248-G

In a 500 mL two-necked round-bottom flask, F1-248-F (4.0 g, 6.29 mmol), potassium phosphate trihydrate (16.70 g, 63 mmol), malononitrile (2.5 g, 37.7 mmol), $Pd(PPh_3)_4$ (363 mg, 0.32 mmol) and 200 mL of DMAc were added under a nitrogen atmosphere, heated to 120° C. and reacted overnight. After HPLC showed that the reaction was completed, the reaction solution was cooled to room temperature and slowly poured into dilute hydrochloric acid to precipitate a large amount of yellow solids. The crude product was filtered and purified through column chromatography to obtain a light yellow solid F1-248-G (3.5 g, with a yield of 99%).

Step 9: Synthesis of Compound F1-248

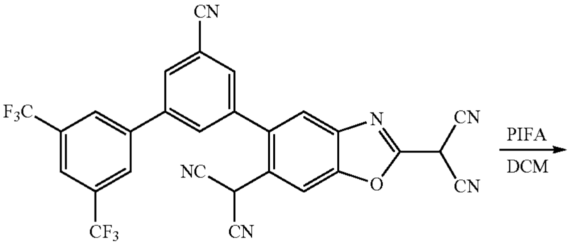

F1-248-G

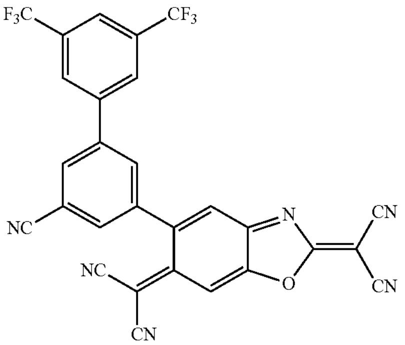

F1-248

In a 2 L two-necked flask, F1-248-G (3.5 g, 6.245 mmol) and 1 L of dichloromethane were added under a nitrogen atmosphere, and PIFA (5.92 g, 12.86 mmol) was added in batches, reacted for 5 days at room temperature and concentrated. Then, an appropriate amount of n-hexane was added to filter black solids as a crude product. The crude product was washed with an appropriate amount of dichloromethane and n-hexane and filtered to obtain Compound F1-248 (3.1 g, with a yield of 88%). The product was confirmed as the target product with a molecular weight of 558.

Those skilled in the art will appreciate that the above preparation methods are merely exemplary. Those skilled in the art can obtain other compound structures of the present disclosure through the modifications of the preparation methods.

The measured LUMO energy level obtained herein is an electrochemical property of a compound determined by a cyclic voltammetry (CV) method. Tests were conducted using a CorrTest CS120 electrochemical workstation produced by WUHAN CORRTEST INSTRUMENTS CORP., LTD. A three-electrode working system: a platinum disk electrode served as a working electrode, a $Ag/AgNO_3$ electrode served as a reference electrode, and a platinum wire electrode served as an auxiliary electrode. Anhydrous DCM was used as a solvent, and 0.1 mol/L tetrabutylammonium hexafluorophosphate was used as a supporting electrolyte. The target compound was prepared into a solution of $10^{-3}$ mol/L, and nitrogen was introduced into the solution for 10 min for oxygen removal before the test. The parameters of the instrument were set as follows: a scan rate of 100 mV/s, a potential interval of 0.5 mV and a test window of 1 V to −0.5 V.

The LUMO values of the selected compounds of the present disclosure were determined by the cyclic voltammetry method. The LUMO value of Compound F1-194 measured in anhydrous dichloromethane was −4.96 eV, and the LUMO value of Compound F1-248 measured in anhydrous dichloromethane was −4.95 eV. It is worth noting that when measured by the same CV method in anhydrous dichloromethane, the LUMO energy level of the hole injection layer material HATCN was −4.33 eV and the LUMO energy level of the p-dopant material F4-TCNQ was −4.94 eV.

HATCN and $F_4$-TCNQ have the following structures:

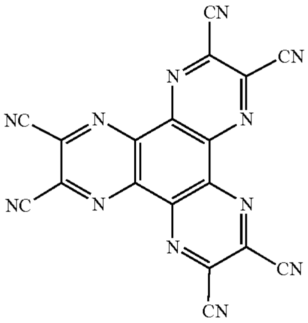

and

HATCN

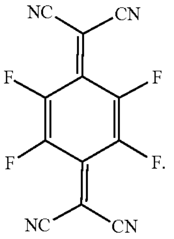

F4-TCNQ

As can be seen through comparison, the LUMO energy level of Compound F1-194 and the LUMO energy level of Compound F1-248 are 0.63 eV and 0.62 eV deeper than that of HATCN respectively and are comparable to that of F4-TCNQ, which can prove that Compound F1-194 and Compound F1-248 are similar to F4-TCNQ and are all strong electron-deficient materials and excellent electron acceptor materials and charge transfer materials and have a great potential for wide applications in the field of electroluminescence. Additionally, such materials also have low volatility. For example, the sublimation temperature of Compound F1-194 at a vacuum degree of $2.2\times10^{-4}$ Pa is as high as 200° C., which is 80° C. higher than the sublimation temperature of F4-TCNQ under the same condition at the same vacuum degree. This indicates that the compound of the present disclosure has lower volatility, which is obviously beneficial for better controlling the deposition of the compound of the present disclosure in an OLED preparation process and the reproducibility in a production process. As can be seen from these data, Compound F1-194 and Compound F1-248 of the present disclosure have relatively great potentials and excellent application prospects both as hole injection layer materials and p-dopant materials.

In an example, the LUMO values of the selected compounds of the present disclosure were calculated based on a DFT [GAUSS-09, B3LYP/6-311G(d)]. Relevant compounds and LUMO values thereof are shown as follows:

F1-6

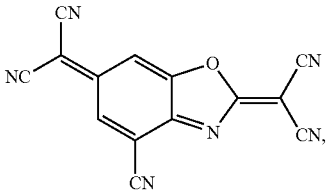

LUMO = -5.70 eV

F1-70

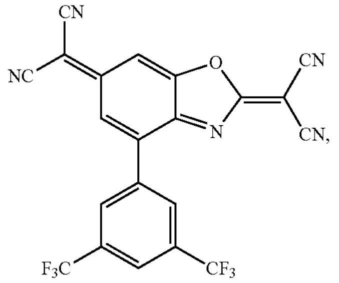

LUMO = -5.46 eV

F1-93

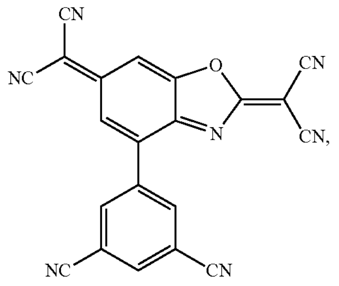

LUMO = -5.58 eV

-continued
F1-124
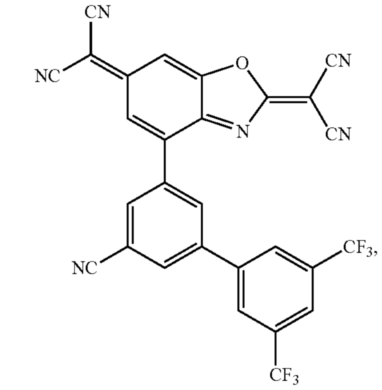
LUMO = -5.48 eV
F1-130
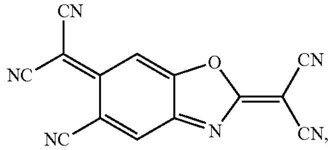
LUMO = -5.70 eV
F1-194
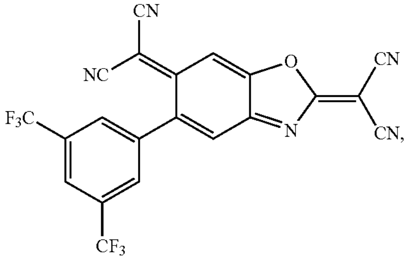
LUMO = -5.55 eV
F1-217
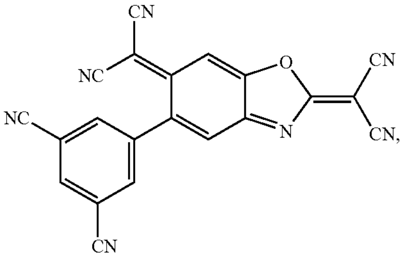
LUMO = -5.56 eV
F1-248
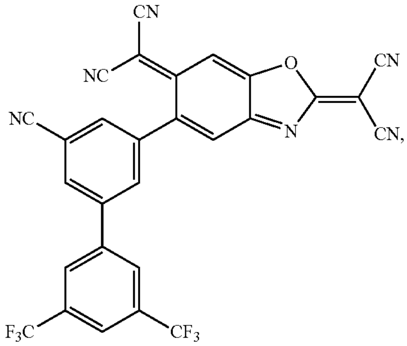
LUMO = -5.42 eV
-continued
F1-254
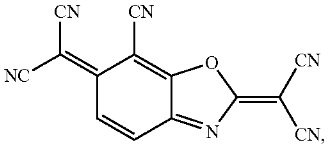
LUMO = -5.64 eV
F1-318
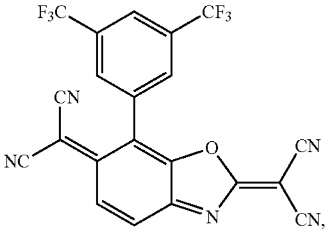
LUMO = -5.40 eV
F1-341
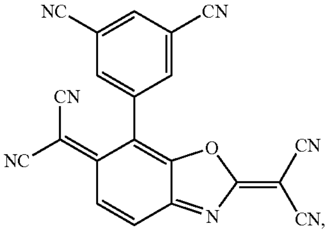
LUMO = -5.54 eV
F1-372
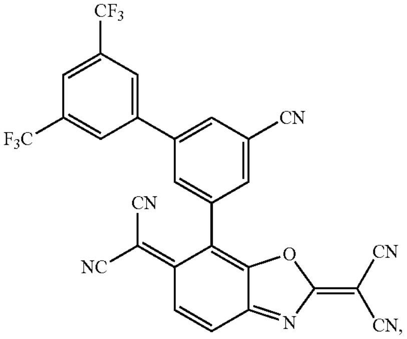
LUMO = -5.46 eV
F1-399
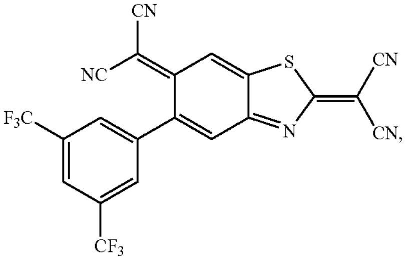
LUMO = -5.37 eV -continued
F1-404
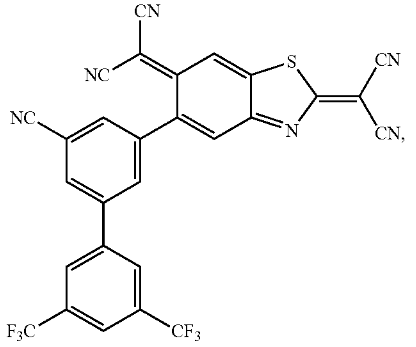
LUMO = -5.41 eV
F1-415
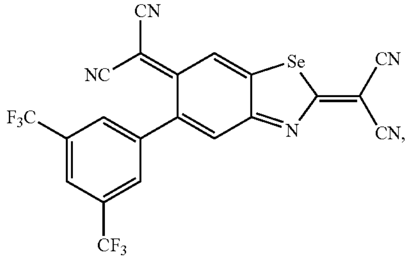
LUMO = -5.46 eV
F2-2
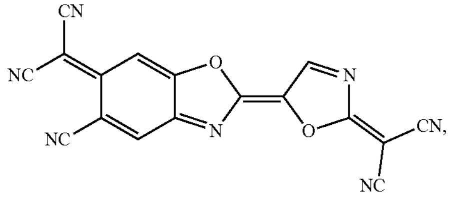
LUMO = -5.52 eV
F2-11
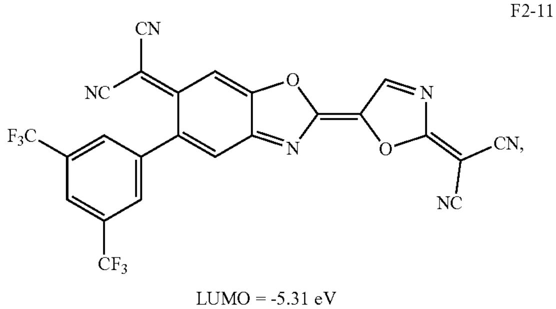
LUMO = -5.31 eV
F2-16
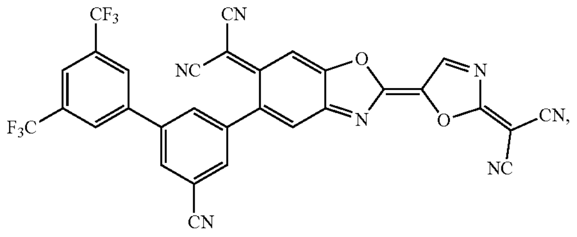
LUMO = -5.35 eV
-continued
F2-27
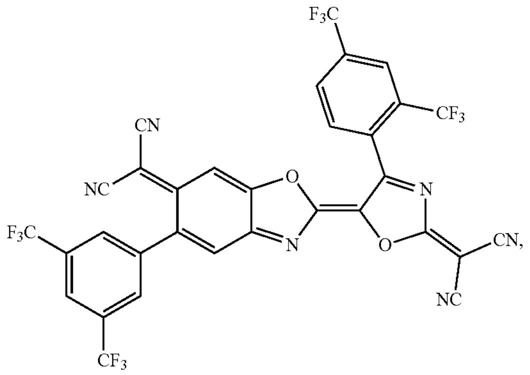
LUMO = -5.31 eV
F2-34
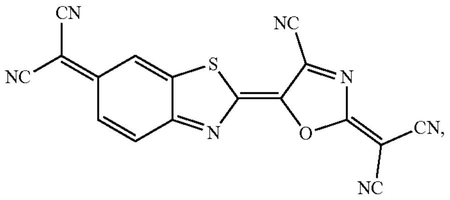
LUMO = -5.44 eV
F2-48
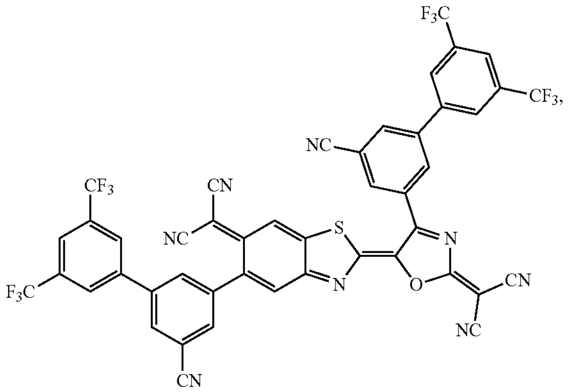
LUMO = -5.39 eV
F2-50
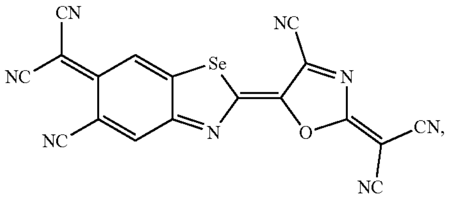
LUMO = -5.70 eV -continued
F2-59
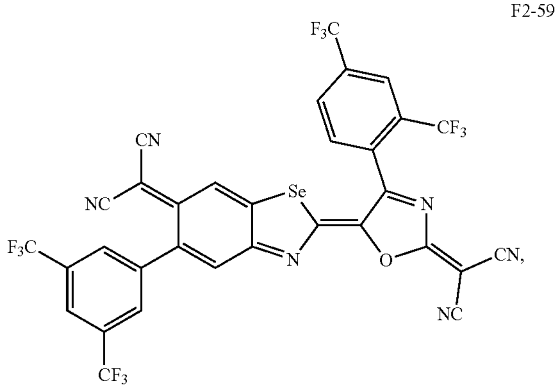
LUMO = -5.28 eV
F2-64
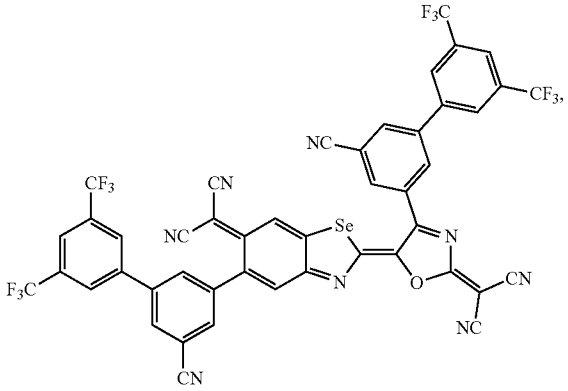
LUMO = -5.31 eV
F2-98
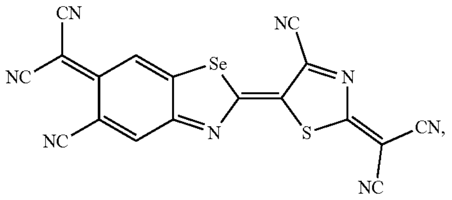
LUMO = -5.74 eV
F2-107
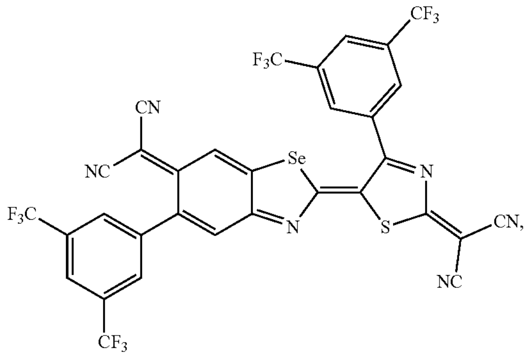
LUMO = -5.33 eV
-continued
F2-112
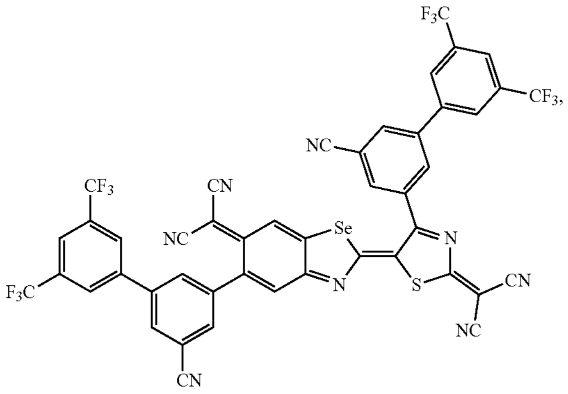
LUMO = -5.51 eV
F3-18
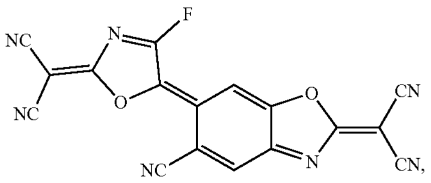
LUMO = -5.70 eV
F3-27
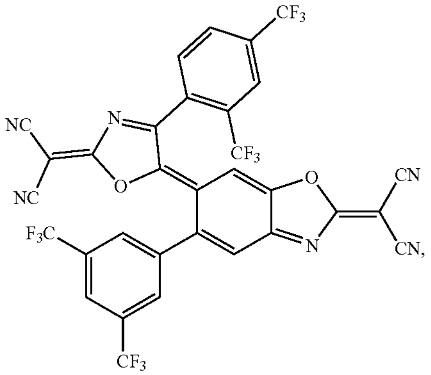
LUMO = -5.47 eV -continued
F3-32
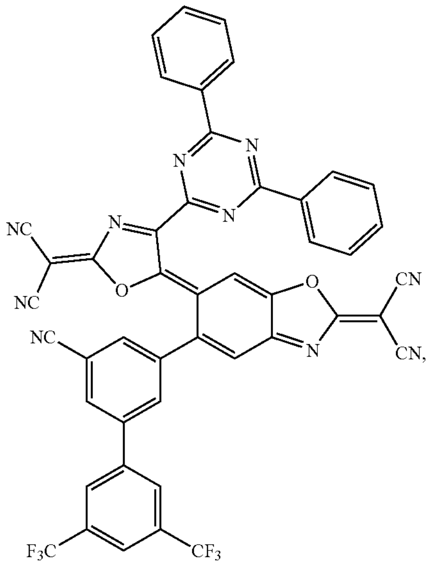
LUMO = -5.35 eV
F3-34
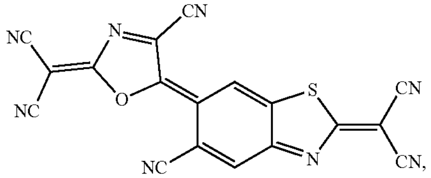
LUMO = -5.92 eV
F3-43
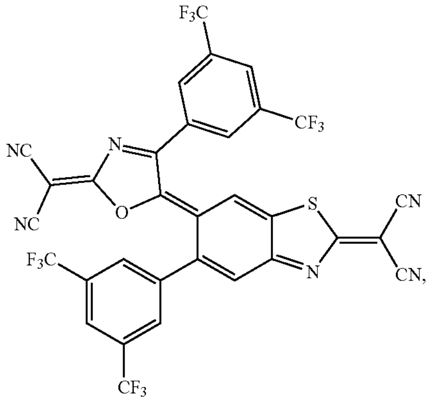
LUMO = -5.57 eV
-continued
F3-48
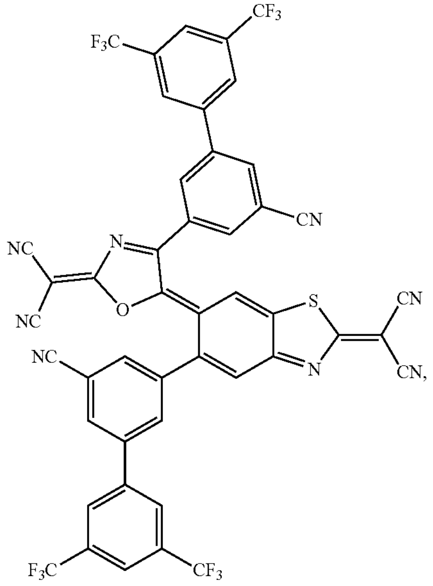
LUMO = -5.64 eV
F3-98
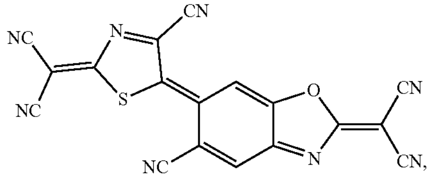
LUMO = -5.94 eV
F3-107
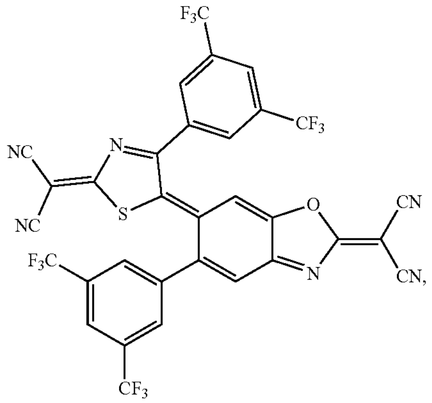
LUMO = -5.56 eV -continued
F3-112
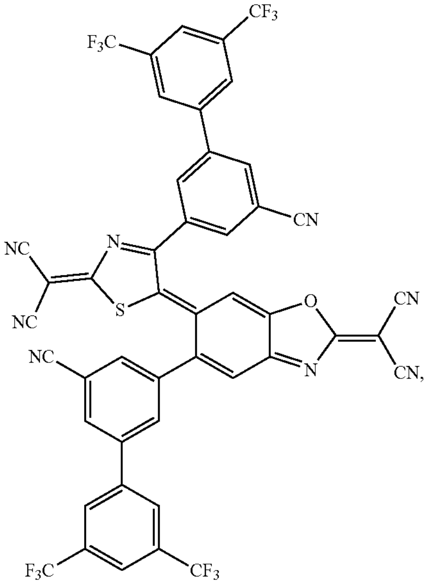
LUMO = -5.76 eV
F3-123
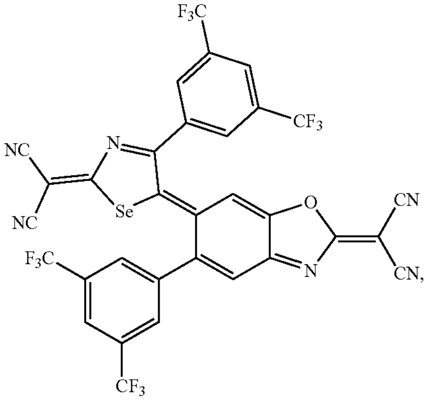
LUMO = -5.51 eV
-continued
F3-128
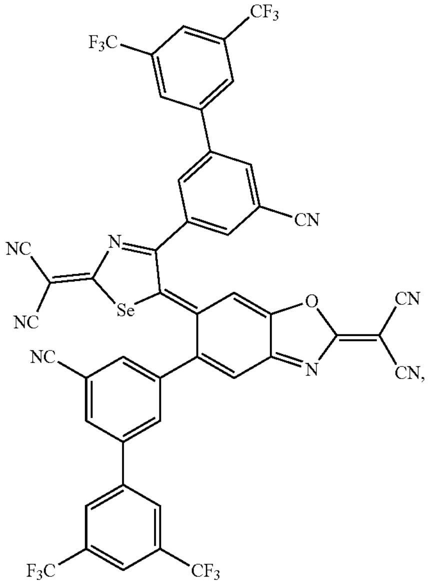
LUMO = -5.56 eV
F4-27
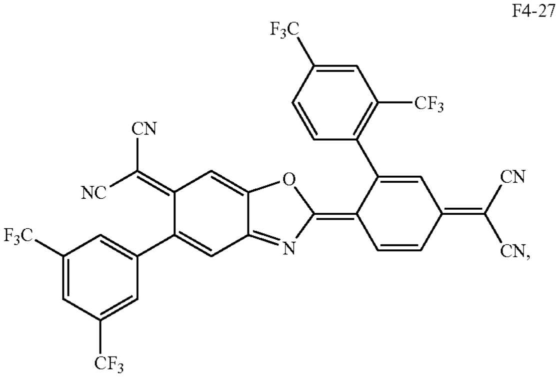
LUMO = -5.36 eV
F4-32
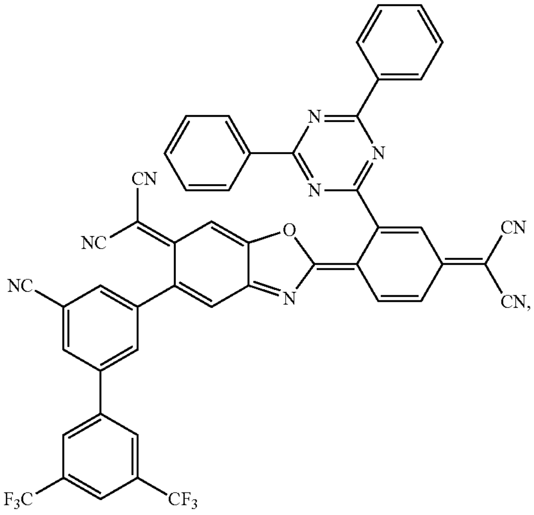
LUMO = -5.24 eV -continued
F4-43
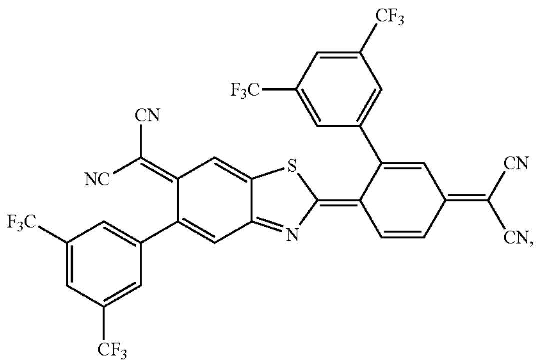
LUMO = -5.39 eV
F4-48
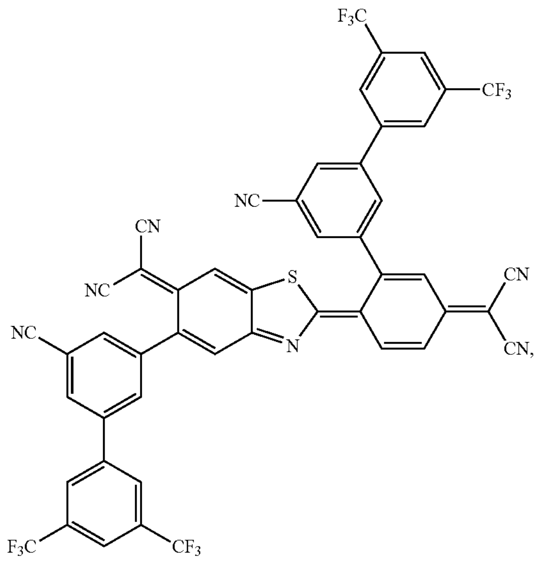
LUMO = -5.44 eV
F4-59
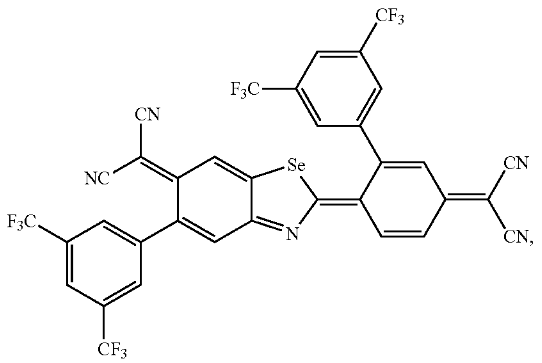
LUMO = -5.38 eV
-continued
F4-64
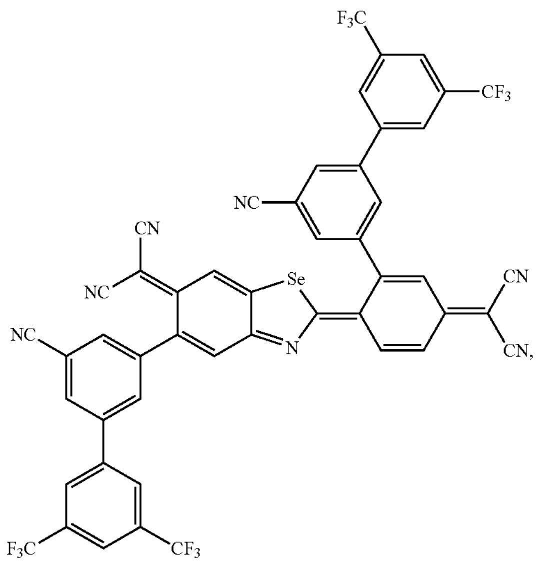
LUMO = -5.41 eV
F5-27
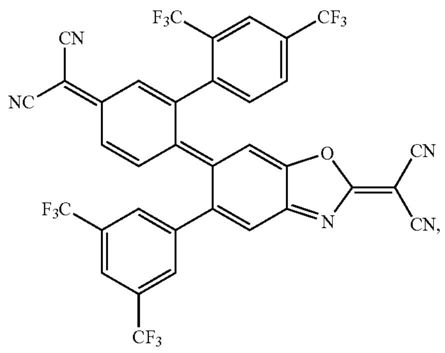
LUMO = -5.57 eV

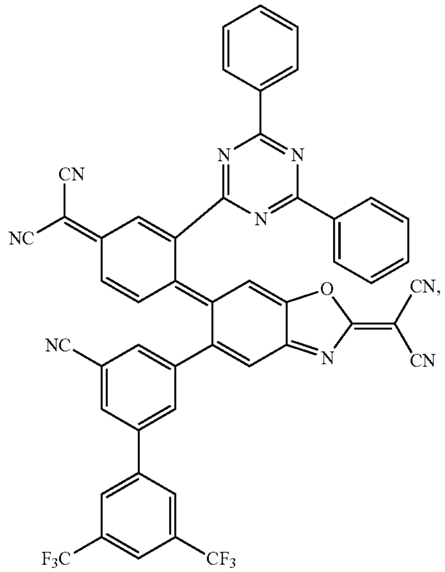
F5 - 32
LUMO = -5.44 eV
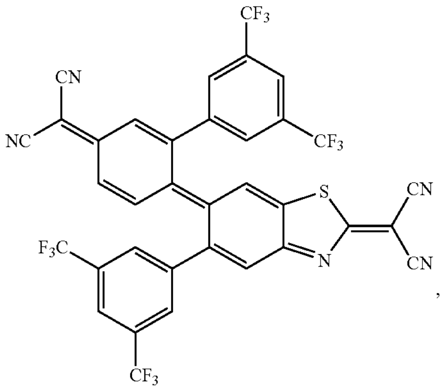
,
F5 - 43
LUMO = -5.56 eV
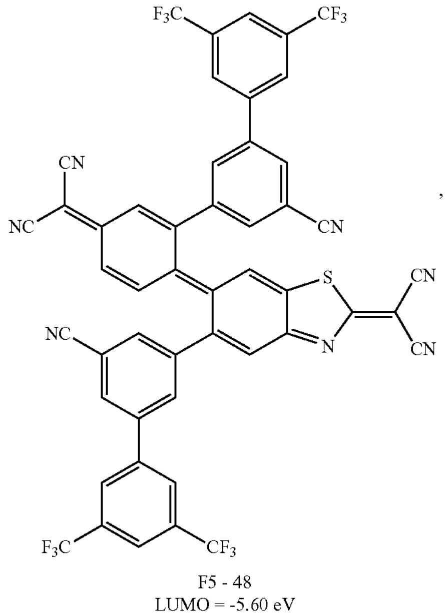
,
F5 - 48
LUMO = -5.60 eV
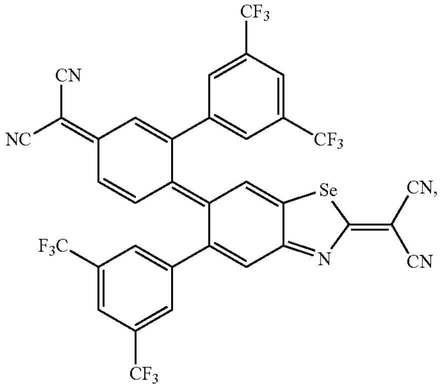
F5 - 59
LUMO = -5.53 eV -continued
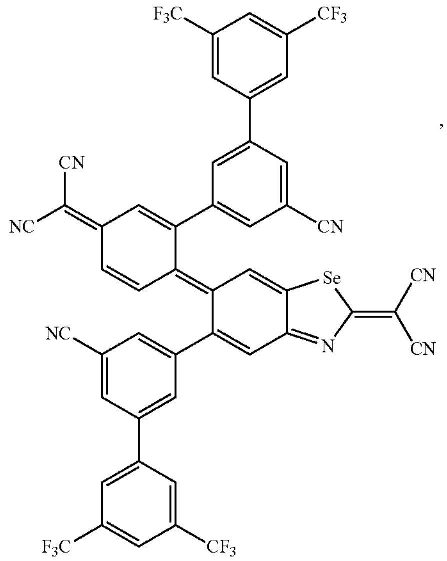
F5 - 64
LUMO = -5.40 eV
,
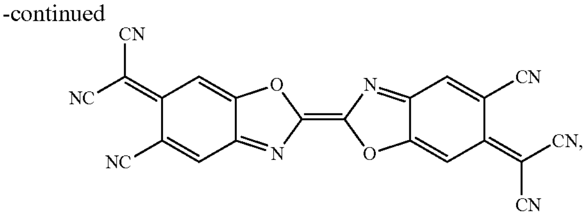
F6 - 50
LUMO = -5.77 eV
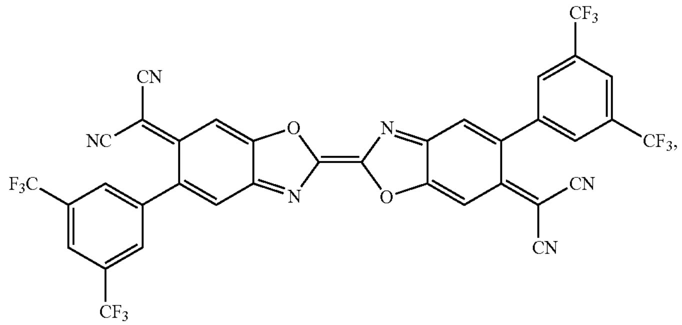
F6 - 11
LUMO = -5.46 eV
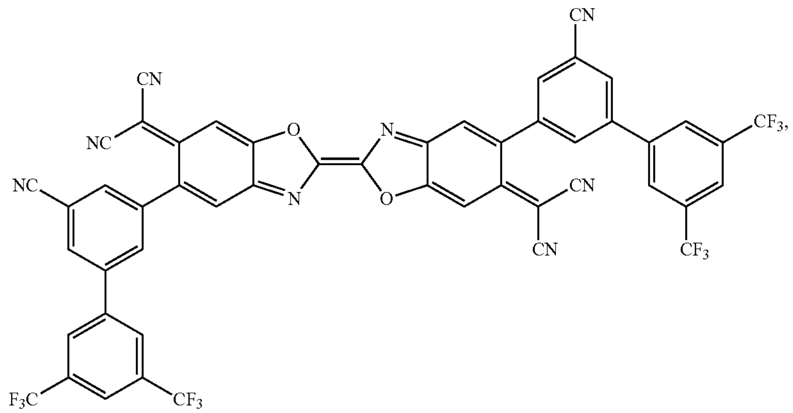
F6 - 16
LUMO = -5.55 eV
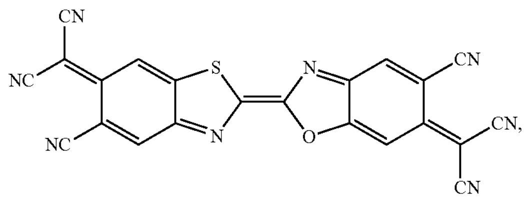
F6 - 18
LUMO = -5.77 eV
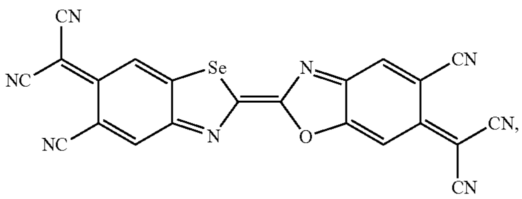
F6 - 34
LUMO = -5.74 eV -continued
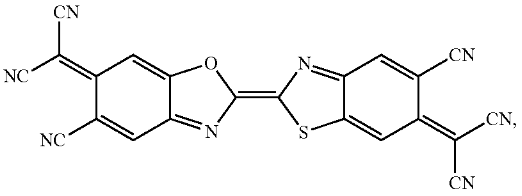
F6 - 50
LUMO = -5.77 eV
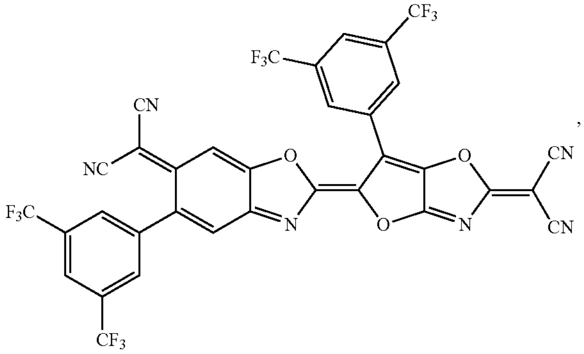
,
F7 - 11
LUMO = -5.35 eV
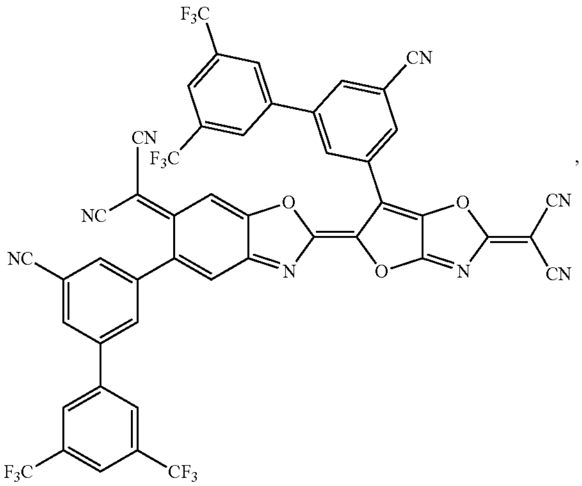
,
F7 - 16
LUMO = -5.42 eV
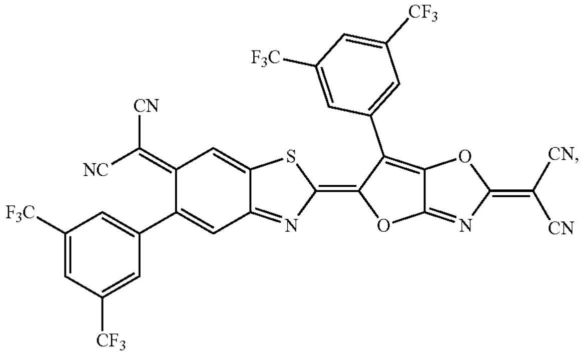
F7 - 27
LUMO = -5.28 eV
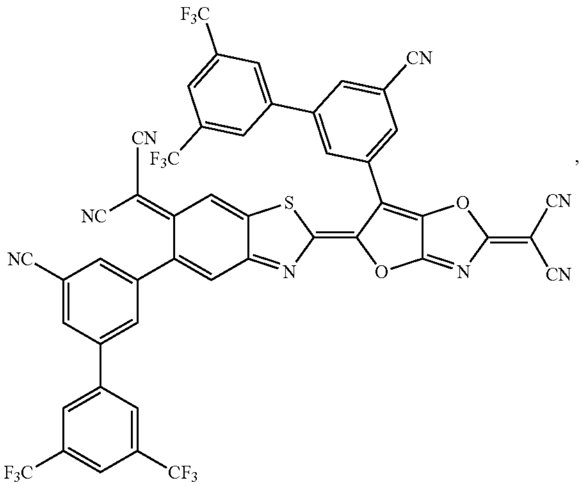
,
F7 - 32
LUMO = -5.30 eV
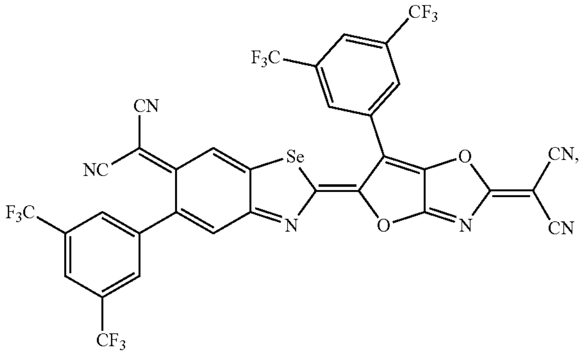
F7 - 43
LUMO = -5.25 eV -continued

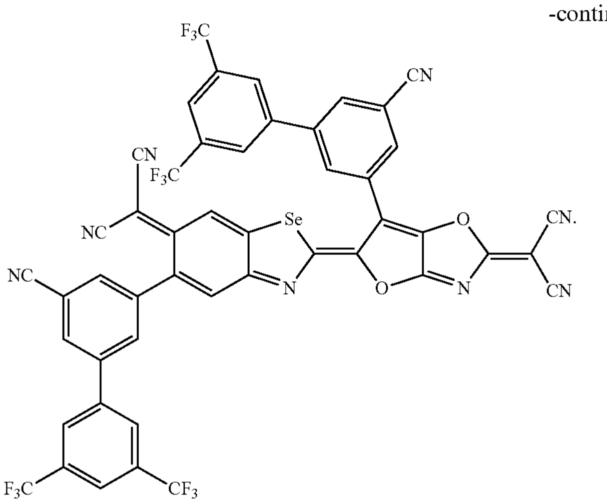

F7 - 48
LUMO = -5.26 eV

The measured LUMO (−4.96 eV) and the DFT-calculated LUMO (−5.55 eV) of Compound F1-194 of the present disclosure differ by 0.59 eV, the measured LUMO (−4.95 eV) and the DFT-calculated LUMO (−5.42 eV) of Compound F1-248 differ by 0.47 eV, the measured LUMO (−4.33 eV) and the DFT-calculated LUMO (−4.80 eV) of HATCN differ by 0.47 eV, and the measured LUMO (−4.94 eV) and the DFT-calculated LUMO (−5.50 eV) of F4-TCNQ differ by 0.56 eV. As can be seen from the preceding comparison, for various compounds with different skeletons, the data measured by CV and DFT calculation results all differ by about 0.53 eV, which shows that the DFT calculation results have a very high reference value. As can be seen from the DFT calculation results of the compounds of the present disclosure, the compounds disclosed in the present disclosure all have very deep LUMO energy levels, are very good electron acceptor materials and charge transfer materials, and have potentials for becoming excellent hole injection materials and excellent p-type conductive doping materials and very broad industrial application prospects.

It is to be understood that various embodiments described herein are merely illustrative and not intended to limit the scope of the present disclosure. Therefore, it is apparent to the persons skilled in the art that the present disclosure as claimed may include variations of specific embodiments and preferred embodiments described herein. Many of the materials and structures described herein may be replaced with other materials and structures without departing from the spirit of the present disclosure. It is to be understood that various theories as to why the present disclosure works are not intended to be limiting.

What is claimed is:

1. A compound having a structure of Formula 1:

Formula 1

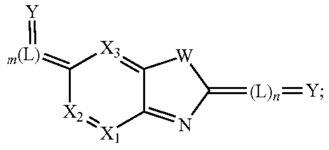

wherein Y is, at each occurrence identically or differently, selected from CR''R''', NR', S or Se;

W is, at each occurrence identically or differently, selected from O, S, Se or $NR_N$;

$X_1$ to $X_3$ are, at each occurrence identically or differently, selected from CR or N;

L is, at each occurrence identically or differently, selected from a cyclic conjugated structure comprising 4 to 30 ring atoms and comprising at least one intracyclic double bond and substituted by one or more substituents $R_L'$;

R, $R_N$, R', R'', R''' and $R_L'$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, a hydroxyl group, a sulfanyl group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted alkylgermanyl having 3 to 20 carbon atoms, substituted or unsubstituted arylgermanyl having 6 to 20 carbon atoms and combinations thereof;

at least one of R, $R_N$, R', R'' and R''' is a group having at least one electron-withdrawing group;

m and n are each selected from an integer from 0 to 1; and adjacent substituents R, $R_N$, R', R'', R''' and $R_L$' can be optionally joined to form a ring.

2. The compound according to claim 1, wherein W is, at each occurrence identically or differently, selected from O, S or Se.

3. The compound according to claim 1, wherein m+n≤1.

4. The compound according to claim 1, wherein at least one of $X_1$ to $X_3$ is selected from CR.

5. The compound according to claim 1, wherein Y is, at each occurrence identically or differently, selected from CR''R''' or NR', and each of R', R'' and R''' is the group having at least one electron-withdrawing group.

6. The compound according to claim 1, wherein a Hammett constant of the electron-withdrawing group is ≥0.05.

7. The compound according to claim 1, wherein the electron-withdrawing group is selected from the group consisting of: halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, an aza-aromatic ring group and any one of the following groups substituted by one or more of halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group and an aza-aromatic ring group: alkyl having 1 to 20 carbon atoms, cycloalkyl having 3 to 20 ring carbon atoms, heteroalkyl having 1 to 20 carbon atoms, arylalkyl having 7 to 30 carbon atoms, alkoxy having 1 to 20 carbon atoms, aryloxy having 6 to 30 carbon atoms, alkenyl having 2 to 20 carbon atoms, alkynyl having 2 to 20 carbon atoms, aryl having 6 to 30 carbon atoms, heteroaryl having 3 to 30 carbon atoms, alkylsilyl having 3 to 20 carbon atoms, arylsilyl having 6 to 20 carbon atoms, substituted or unsubstituted alkylgermanyl having 3 to 20 carbon atoms, substituted or unsubstituted arylgermanyl having 6 to 20 carbon atoms and combinations thereof.

8. The compound according to claim 1, wherein Y is, at each occurrence identically or differently, selected from the group consisting of the following structures:

S, Se,

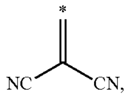
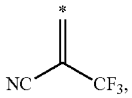
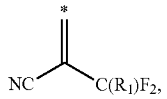
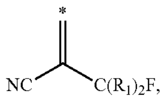
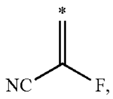
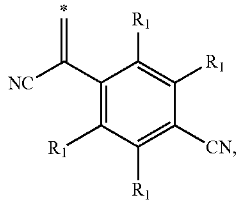
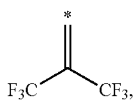
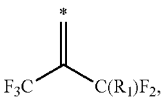
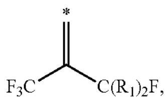
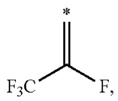

-continued

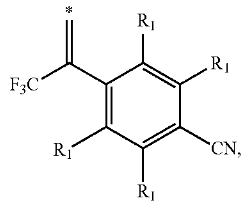
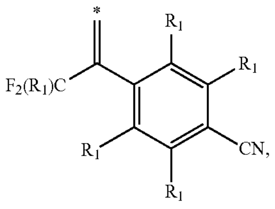
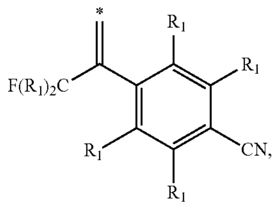
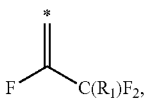
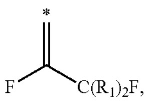
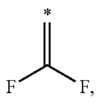
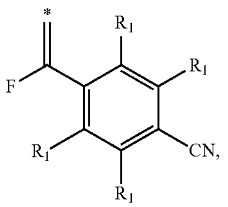
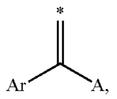
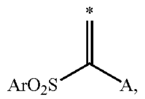
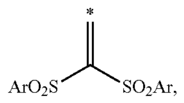
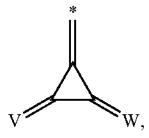
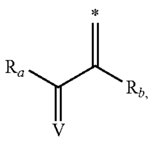
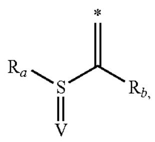
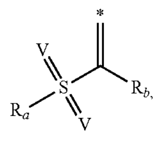
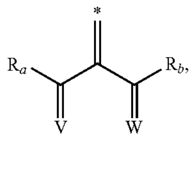
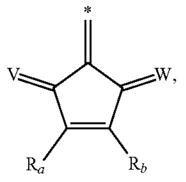
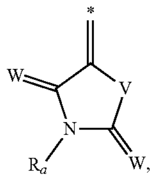
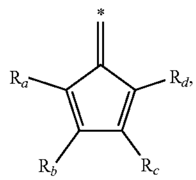
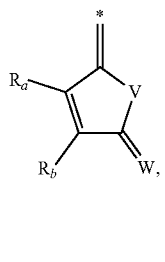
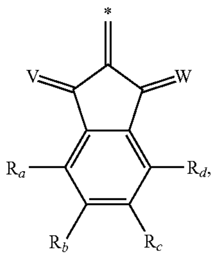

-continued

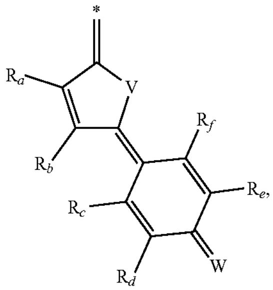

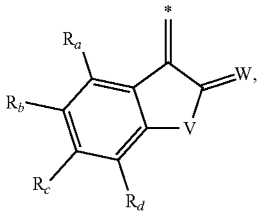

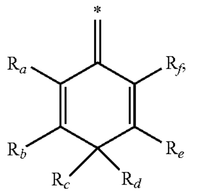

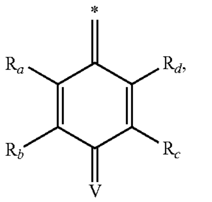

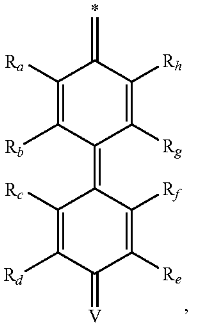

,

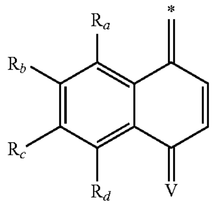

,

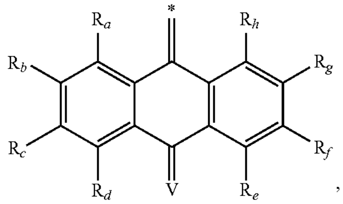

,

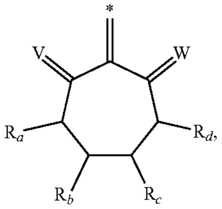

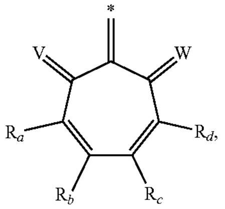

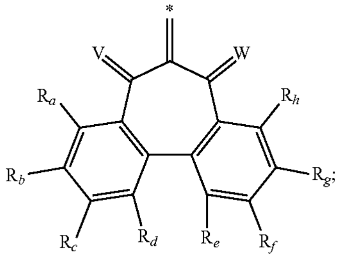

wherein $R_1$ is, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted alkylgermanyl having 3 to 20 carbon atoms, substituted or unsubstituted arylgermanyl having 6 to 20 carbon atoms and combinations thereof;

wherein V and W are, at each occurrence identically or differently, selected from $CR_vR_w$, $NR_v$, O, S or Se;

wherein Ar is, at each occurrence identically or differently, selected from substituted or unsubstituted aryl having 6 to 30 carbon atoms or substituted or unsubstituted heteroaryl having 3 to 30 carbon atoms;

wherein A, $R_a$, $R_b$, $R_c$, $R_d$, $R_e$, $R_f$, $R_g$, $R_h$, $R_v$ and $R_w$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted alkylgermanyl having 3 to 20 carbon atoms, substituted or unsubstituted arylgermanyl having 6 to 20 carbon atoms and combinations thereof;

wherein A is a group having at least one electron-withdrawing group, and for any one of the structures, when one or more of $R_a$, $R_b$, $R_c$, $R_d$, $R_e$, $R_f$, $R_g$, $R_h$, $R_v$ and $R_w$ are present, at least one of $R_a$, $R_b$, $R_c$, $R_d$, $R_e$, $R_f$, $R_g$, $R_h$, $R_v$ and $R_w$ is a group having at least one electron-withdrawing group; and wherein "*" represents a position where Y is connected to L or the six-membered and five-membered conjugated ring comprising $X_1$ to $X_3$ and W in Formula 1.

9. The compound according to claim 1, wherein R and $R_N$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, unsubstituted alkyl having 1 to 20 carbon atoms, unsubstituted cycloalkyl having 3 to 20 ring carbon atoms, unsubstituted alkoxy having 1 to 20 carbon atoms, unsubstituted alkenyl having 2 to 20 carbon atoms, unsubstituted aryl having 6 to 30 carbon atoms, unsubstituted heteroaryl having 3 to 30 carbon atoms, any one of the following groups substituted by one or more of halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group and a phosphoroso group: alkyl having 1 to 20 carbon atoms, cycloalkyl having 3 to 20 ring carbon atoms, alkoxy having 1 to 20 carbon atoms, alkenyl having 2 to 20 carbon atoms, aryl having 6 to 30 carbon atoms and heteroaryl having 3 to 30 carbon atoms, and combinations thereof.

10. The compound according to claim 1, wherein L is, at each occurrence identically or differently, selected from the group consisting of the following structures:

L-1

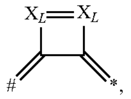

L-2

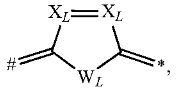

L-3

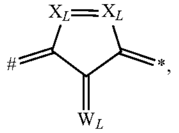

L-4

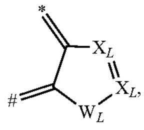

L-5

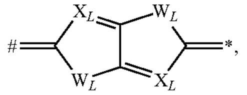

L-6

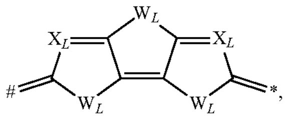

L-7

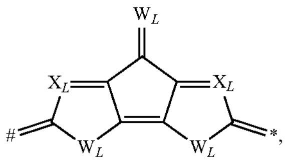

L-8

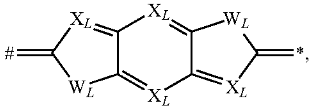

-continued

L-9

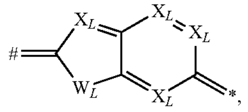

L-10

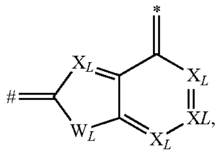

L-11

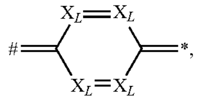

L-12

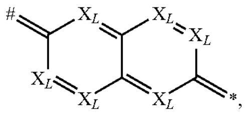

L-13

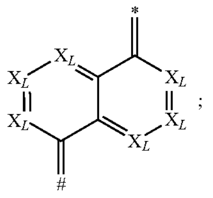

wherein $W_L$ is, at each occurrence identically or differently, selected from O, S, Se or $NR_N'$;

$X_L$ is, at each occurrence identically or differently, selected from $CR_L$ or N;

$R_L$ and $R_N'$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, a hydroxyl group, a sulfanyl group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted alkylgermanyl having 3 to 20 carbon atoms, substituted or unsubstituted arylgermanyl having 6 to 20 carbon atoms and combinations thereof;

"*" represents a position where Formula L-1 to Formula L-13 are connected to the group Y in Formula 1;

"#" represents a position where Formula L-1 to Formula L-13 are connected to the six-membered and five-membered conjugated ring comprising $X_1$ to $X_3$ and W in Formula 1; and adjacent substituents $R_L$ and $R_N$' can be optionally joined to form a ring.

11. The compound according to claim 1, wherein the compound has a structure represented by any one of Formula F1 to Formula F10:

F1

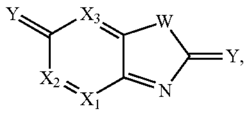

F2

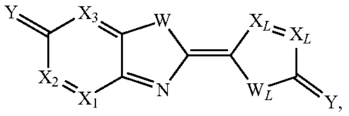

F3

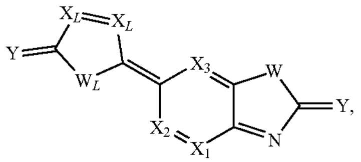

F4

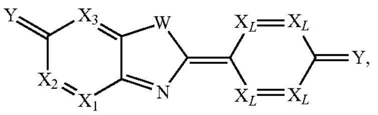

F5

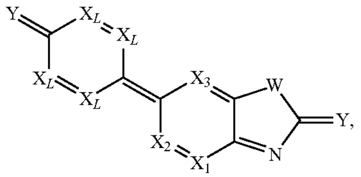

F6

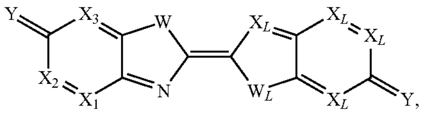

F7

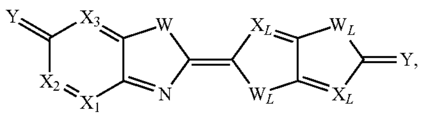

F8

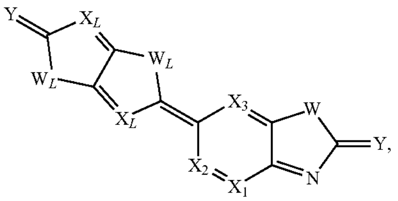

F9

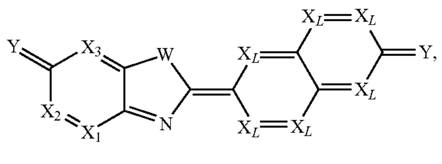

-continued

F10

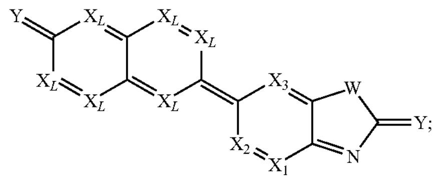

wherein

Y is, at each occurrence identically or differently, selected from S, Se, CR"R'" or NR';

W is, at each occurrence identically or differently, selected from O, S, Se or $NR_N$;

$X_1$ to $X_3$ are, at each occurrence identically or differently, selected from CR or N;

$W_L$ is, at each occurrence identically or differently, selected from O, S, Se or $NR_N$';

$X_L$ is, at each occurrence identically or differently, selected from $CR_L$ or N;

R, $R_N$, $R_L$, R', R", R'" and $R_N$' are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted alkylgermanyl having 3 to 20 carbon atoms, substituted or unsubstituted arylgermanyl having 6 to 20 carbon atoms and combinations thereof;

at least one of R, $R_N$, R', R" and R'" is a group having at least one electron-withdrawing group; and adjacent substituents R, $R_N$, $R_L$, R', R", R'" and $R_N$' can be optionally joined to form a ring.

12. The compound according to claim 1, wherein Y is selected from

A1

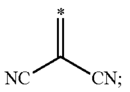

wherein "*" represents a position where Y is connected to L or the six-membered and five-membered conjugated ring comprising $X_1$ to $X_3$ and W in Formula 1.

13. The compound according to claim 1, wherein R and $R_N$ are, at each occurrence identically or differently, selected from the group consisting of: hydrogen, deuterium, methyl, isopropyl, $NO_2$, $SO_2CH_3$, $SCF_3$, $C_2F_5$, $OC_2F_5$, $OCH_3$, diphenylmethylsilyl, phenyl, methoxyphenyl, p-methylphenyl, 2,6-diisopropylphenyl, biphenyl, polyfluorophenyl, difluoropyridyl, nitrophenyl, dimethylthiazolyl, vinyl substituted by one or more of CN or $CF_3$, acetenyl substituted by one of CN or $CF_3$, dimethylphosphoroso, diphenylphosphoroso, F, $CF_3$, $OCF_3$, $SF_5$, $SO_2CF_3$, cyano, isocyano, SCN, OCN, trifluoromethylphenyl, trifluoromethoxyphenyl, bis(trifluoromethyl)phenyl, bis(trifluoromethoxy)phenyl, 4-cyanotetrafluorophenyl, phenyl or biphenyl substituted by one or more of F, CN or $CF_3$, tetrafluoropyridyl, pyrimidinyl, triazinyl, diphenylboranyl, oxaboraanthryl and combinations thereof.

14. The compound according to claim 1, wherein Y is, at each occurrence identically or differently, selected from the group consisting of the following structures:

S, Se,

A1

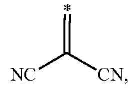

A2

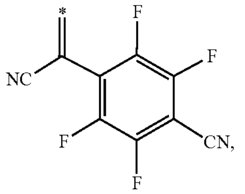

A3

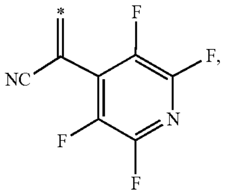

A4

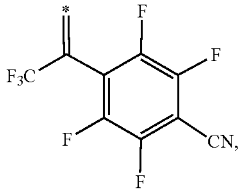

A5

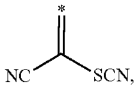

A6

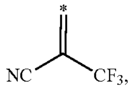

A7

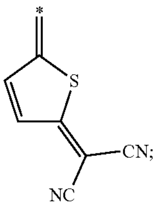

wherein "*" represents a position where Y is connected to L or the six-membered and five-membered conjugated ring comprising $X_1$ to $X_3$ and W in Formula 1.

15. The compound according to claim 14, wherein R, $R_L$, and $R_N$ are, at each occurrence identically or differently, selected from the group consisting of the following structures:

B1

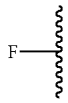

B2

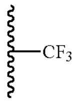

B3

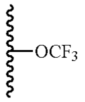

B4

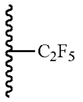

B5

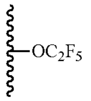

B6

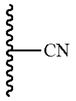

B7

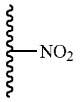

B8

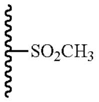

B9

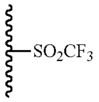

B10

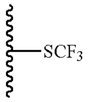

B11

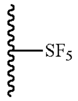

B12

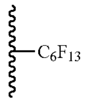

-continued
B13
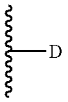
B14
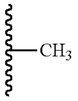
B15
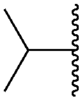
B16
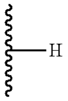
B17
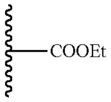
B18
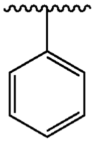
B19
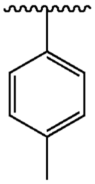
B20
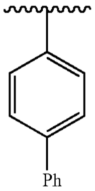
B21
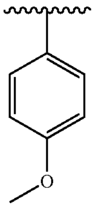
B22
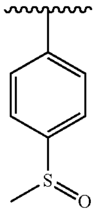
-continued
B23
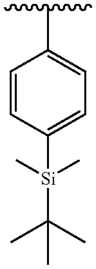
B24
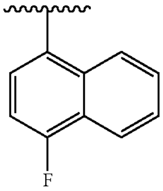
B25
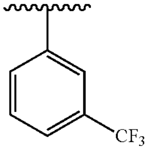
B26
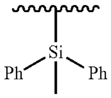
B27
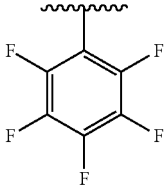
B28
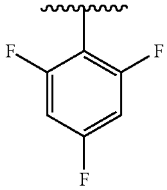
B29
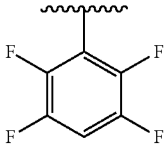
B30
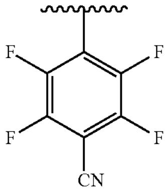

-continued
B31
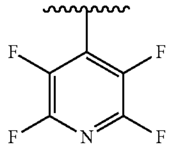
B32
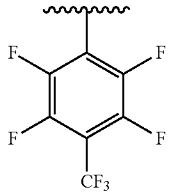
B33
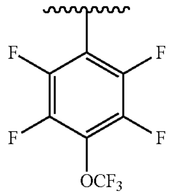
B34
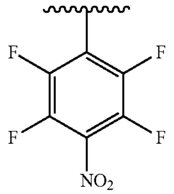
B35
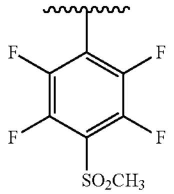
B36
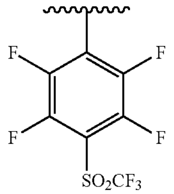
B37
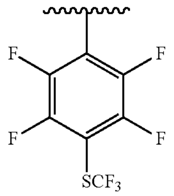
B38
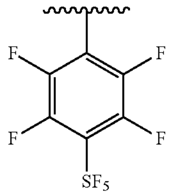
-continued
B39
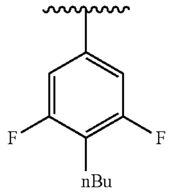
B40
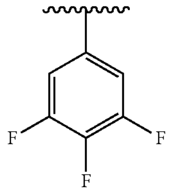
B41
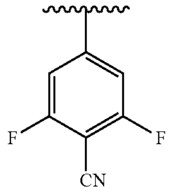
B42
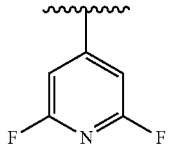
B43
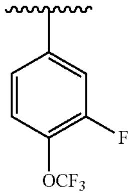
B44
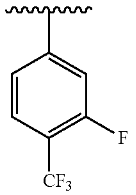
B45
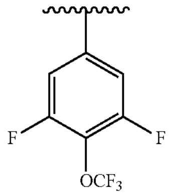
B46
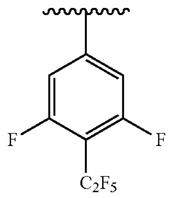

-continued
B47
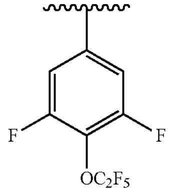
B48
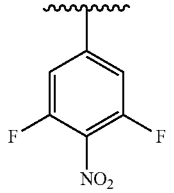
B49
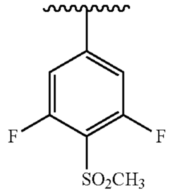
B50
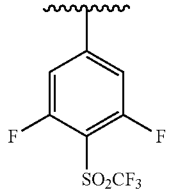
B51
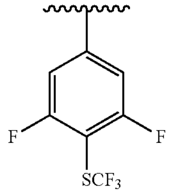
B52
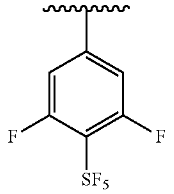
B53
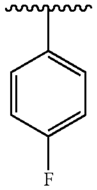
B54
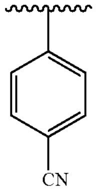
-continued
B55
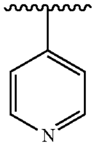
B56
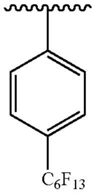
B57
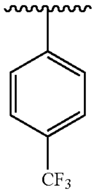
B58
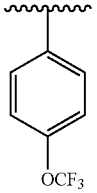
B59
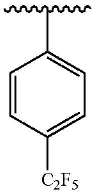
B60
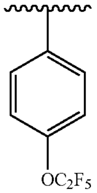
B61
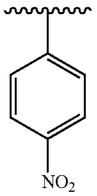
B62
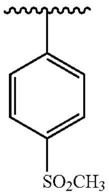

-continued
B63
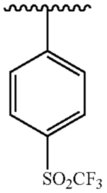
B64
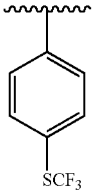
B65
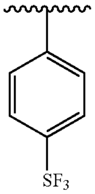
B66
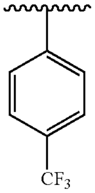
B67
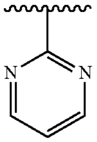
B68
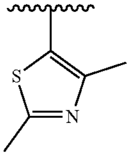
B69
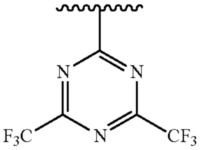
B70
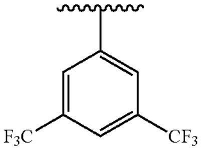
B71
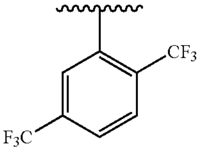
-continued
B72
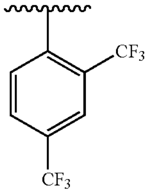
B73
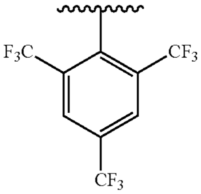
B74
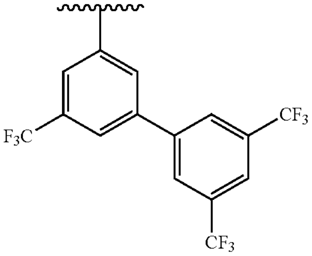
B75
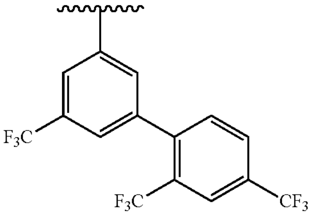
B76
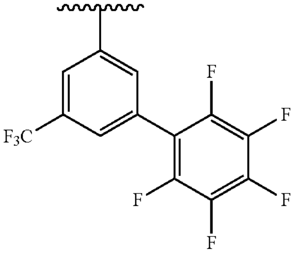
B77
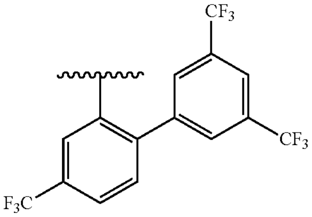
B78
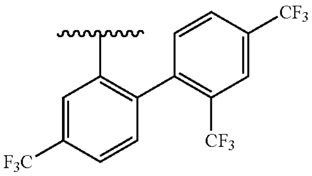

-continued
B79
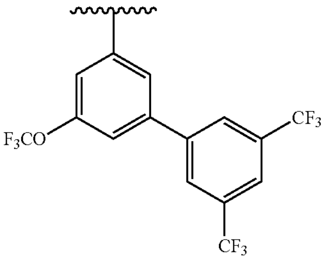
B80
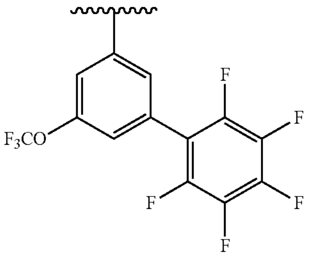
B81
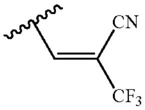
B82
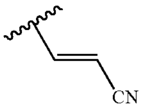
B83
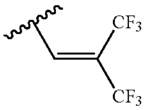
B84
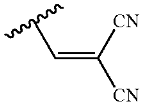
B85
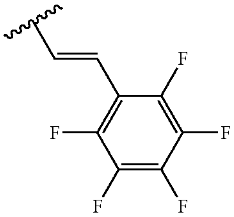
B86
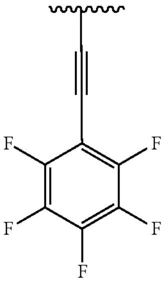
-continued
B87
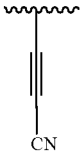
B88
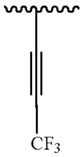
B89
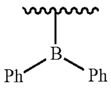
B90
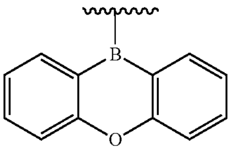
B91
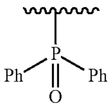
B92
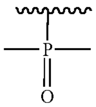
B93
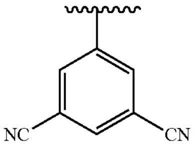
B94
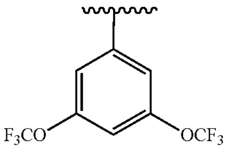
B95
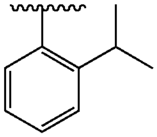
B96
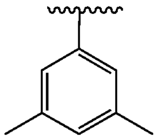

-continued
B97
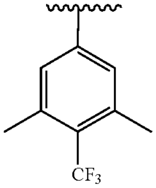
B98
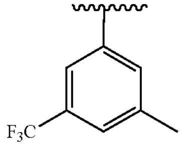
B99
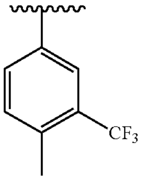
B100
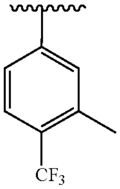
B101
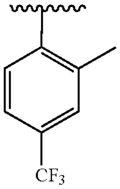
B102
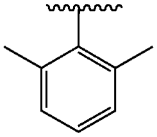
B103
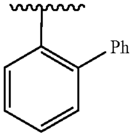
B104
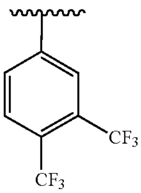
B105
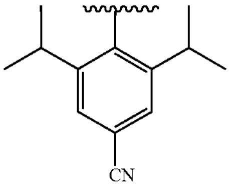
-continued
B106
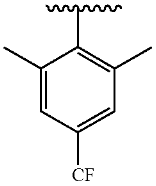
B107
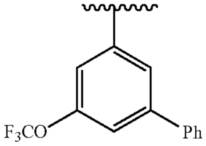
B108
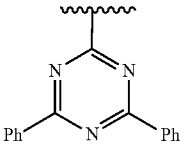
B109
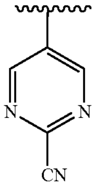
B110
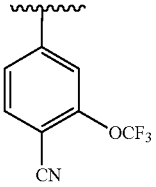
B111
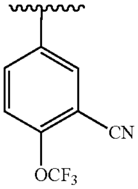
B112
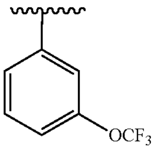
B113
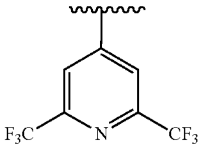
B114
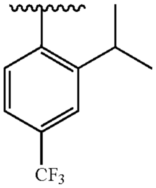

-continued

B115

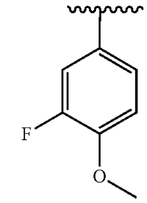

B116

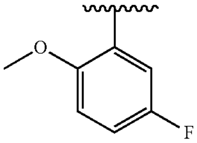

B117

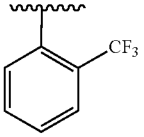

B118

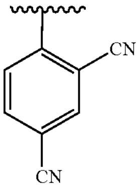

B119

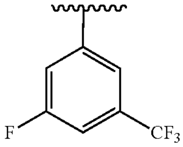

B120

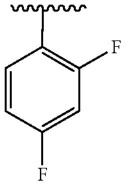

B121

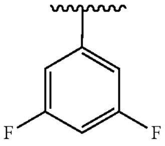

-continued

B122

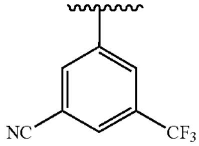

B123

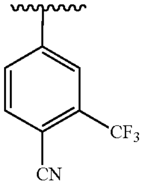

B124

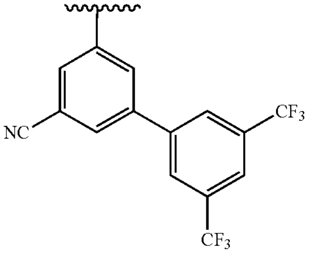

wherein “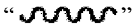” represents a position where the group R having the above structure is connected to the six-membered ring comprising $X_1$ to $X_3$ in Formula 1, or represents a position where the group $R_L$ having the above structure is connected to the group L, or represents a position where $R_N$ is connected to N when W is selected from $NR_N$.

16. The compound according to claim 15, wherein the compound is selected from the group consisting of Compound F1-1 to Compound F1-436, Compound F2-1 to Compound F2-160, Compound F3-1 to Compound F3-160, Compound F4-1 to Compound F4-96, Compound F5-1 to Compound F5-96, Compound F6-1 to Compound F6-96 and Compound F7-1 to Compound F7-96;

wherein Compound F1-1 to Compound F1-436 each have a structure represented by

F1

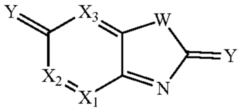

in Formula F1, two Y are the same, and Y, $X_1$, $X_2$, $X_3$ and W are selected from atoms or groups in the following table, respectively:

| Compound No. | Y | $X_1$ | $X_2$ | $X_3$ | W | Compound No. | Y | $X_1$ | $X_2$ | $X_3$ | W |
|---|---|---|---|---|---|---|---|---|---|---|---|
| F1-1 | A1 | C-B1 | C-B16 | C-B16 | O | F1-2 | A1 | C-B2 | C-B16 | C-B16 | O |
| F1-3 | A1 | C-B3 | C-B16 | C-B16 | O | F1-4 | A1 | C-B4 | C-B16 | C-B16 | O |
| F1-5 | A1 | C-B5 | C-B16 | C-B16 | O | F1-6 | A1 | C-B6 | C-B16 | C-B16 | O |
| F1-7 | A1 | C-B7 | C-B16 | C-B16 | O | F1-8 | A1 | C-B8 | C-B16 | C-B16 | O |
| F1-9 | A1 | C-B9 | C-B16 | C-B16 | O | F1-10 | A1 | C-B10 | C-B16 | C-B16 | O |
| F1-11 | A1 | C-B11 | C-B16 | C-B16 | O | F1-12 | A1 | C-B12 | C-B16 | C-B16 | O |
| F1-13 | A1 | C-B13 | C-B16 | C-B16 | O | F1-14 | A1 | C-B14 | C-B16 | C-B16 | O |
| F1-15 | A1 | C-B15 | C-B16 | C-B16 | O | F1-16 | A1 | C-B16 | C-B16 | C-B16 | O |
| F1-17 | A1 | C-B17 | C-B16 | C-B16 | O | F1-18 | A1 | C-B18 | C-B16 | C-B16 | O |
| F1-19 | A1 | C-B19 | C-B16 | C-B16 | O | F1-20 | A1 | C-B20 | C-B16 | C-B16 | O |
| F1-21 | A1 | C-B21 | C-B16 | C-B16 | O | F1-22 | A1 | C-B22 | C-B16 | C-B16 | O |
| F1-23 | A1 | C-B23 | C-B16 | C-B16 | O | F1-24 | A1 | C-B24 | C-B16 | C-B16 | O |

-continued

| Compound No. | Y | $X_1$ | $X_2$ | $X_3$ | W | Compound No. | Y | $X_1$ | $X_2$ | $X_3$ | W |
|---|---|---|---|---|---|---|---|---|---|---|---|
| F1-25 | A1 | C-B25 | C-B16 | C-B16 | O | F1-26 | A1 | C-B26 | C-B16 | C-B16 | O |
| F1-27 | A1 | C-B27 | C-B16 | C-B16 | O | F1-28 | A1 | C-B28 | C-B16 | C-B16 | O |
| F1-29 | A1 | C-B29 | C-B16 | C-B16 | O | F1-30 | A1 | C-B30 | C-B16 | C-B16 | O |
| F1-31 | A1 | C-B31 | C-B16 | C-B16 | O | F1-32 | A1 | C-B32 | C-B16 | C-B16 | O |
| F1-33 | A1 | C-B33 | C-B16 | C-B16 | O | F1-34 | A1 | C-B34 | C-B16 | C-B16 | O |
| F1-35 | A1 | C-B35 | C-B16 | C-B16 | O | F1-36 | A1 | C-B36 | C-B16 | C-B16 | O |
| F1-37 | A1 | C-B37 | C-B16 | C-B16 | O | F1-38 | A1 | C-B38 | C-B16 | C-B16 | O |
| F1-39 | A1 | C-B39 | C-B16 | C-B16 | O | F1-40 | A1 | C-B40 | C-B16 | C-B16 | O |
| F1-41 | A1 | C-B41 | C-B16 | C-B16 | O | F1-42 | A1 | C-B42 | C-B16 | C-B16 | O |
| F1-43 | A1 | C-B43 | C-B16 | C-B16 | O | F1-44 | A1 | C-B44 | C-B16 | C-B16 | O |
| F1-45 | A1 | C-B45 | C-B16 | C-B16 | O | F1-46 | A1 | C-B46 | C-B16 | C-B16 | O |
| F1-47 | A1 | C-B47 | C-B16 | C-B16 | O | F1-48 | A1 | C-B48 | C-B16 | C-B16 | O |
| F1-49 | A1 | C-B49 | C-B16 | C-B16 | O | F1-50 | A1 | C-B50 | C-B16 | C-B16 | O |
| F1-51 | A1 | C-B51 | C-B16 | C-B16 | O | F1-52 | A1 | C-B52 | C-B16 | C-B16 | O |
| F1-53 | A1 | C-B53 | C-B16 | C-B16 | O | F1-54 | A1 | C-B54 | C-B16 | C-B16 | O |
| F1-55 | A1 | C-B55 | C-B16 | C-B16 | O | F1-56 | A1 | C-B56 | C-B16 | C-B16 | O |
| F1-57 | A1 | C-B57 | C-B16 | C-B16 | O | F1-58 | A1 | C-B58 | C-B16 | C-B16 | O |
| F1-59 | A1 | C-B59 | C-B16 | C-B16 | O | F1-60 | A1 | C-B60 | C-B16 | C-B16 | O |
| F1-61 | A1 | C-B61 | C-B16 | C-B16 | O | F1-62 | A1 | C-B62 | C-B16 | C-B16 | O |
| F1-63 | A1 | C-B63 | C-B16 | C-B16 | O | F1-64 | A1 | C-B64 | C-B16 | C-B16 | O |
| F1-65 | A1 | C-B65 | C-B16 | C-B16 | O | F1-66 | A1 | C-B66 | C-B16 | C-B16 | O |
| F1-67 | A1 | C-B67 | C-B16 | C-B16 | O | F1-68 | A1 | C-B68 | C-B16 | C-B16 | O |
| F1-69 | A1 | C-B69 | C-B16 | C-B16 | O | F1-70 | A1 | C-B70 | C-B16 | C-B16 | O |
| F1-71 | A1 | C-B71 | C-B16 | C-B16 | O | F1-72 | A1 | C-B72 | C-B16 | C-B16 | O |
| F1-73 | A1 | C-B73 | C-B16 | C-B16 | O | F1-74 | A1 | C-B74 | C-B16 | C-B16 | O |
| F1-75 | A1 | C-B75 | C-B16 | C-B16 | O | F1-76 | A1 | C-B76 | C-B16 | C-B16 | O |
| F1-77 | A1 | C-B77 | C-B16 | C-B16 | O | F1-78 | A1 | C-B78 | C-B16 | C-B16 | O |
| F1-79 | A1 | C-B79 | C-B16 | C-B16 | O | F1-80 | A1 | C-B80 | C-B16 | C-B16 | O |
| F1-81 | A1 | C-B81 | C-B16 | C-B16 | O | F1-82 | A1 | C-B82 | C-B16 | C-B16 | O |
| F1-83 | A1 | C-B83 | C-B16 | C-B16 | O | F1-84 | A1 | C-B84 | C-B16 | C-B16 | O |
| F1-85 | A1 | C-B85 | C-B16 | C-B16 | O | F1-86 | A1 | C-B86 | C-B16 | C-B16 | O |
| F1-87 | A1 | C-B87 | C-B16 | C-B16 | O | F1-88 | A1 | C-B88 | C-B16 | C-B16 | O |
| F1-89 | A1 | C-B89 | C-B16 | C-B16 | O | F1-90 | A1 | C-B90 | C-B16 | C-B16 | O |
| F1-91 | A1 | C-B91 | C-B16 | C-B16 | O | F1-92 | A1 | C-B92 | C-B16 | C-B16 | O |
| F1-93 | A1 | C-B93 | C-B16 | C-B16 | O | F1-94 | A1 | C-B94 | C-B16 | C-B16 | O |
| F1-95 | A1 | C-B95 | C-B16 | C-B16 | O | F1-96 | A1 | C-B96 | C-B16 | C-B16 | O |
| F1-97 | A1 | C-B97 | C-B16 | C-B16 | O | F1-98 | A1 | C-B98 | C-B16 | C-B16 | O |
| F1-99 | A1 | C-B99 | C-B16 | C-B16 | O | F1-100 | A1 | C-B100 | C-B16 | C-B16 | O |
| F1-101 | A1 | C-B101 | C-B16 | C-B16 | O | F1-102 | A1 | C-B102 | C-B16 | C-B16 | O |
| F1-103 | A1 | C-B103 | C-B16 | C-B16 | O | F1-104 | A1 | C-B104 | C-B16 | C-B16 | O |
| F1-105 | A1 | C-B105 | C-B16 | C-B16 | O | F1-106 | A1 | C-B106 | C-B16 | C-B16 | O |
| F1-107 | A1 | C-B107 | C-B16 | C-B16 | O | F1-108 | A1 | C-B108 | C-B16 | C-B16 | O |
| F1-109 | A1 | C-B109 | C-B16 | C-B16 | O | F1-110 | A1 | C-B110 | C-B16 | C-B16 | O |
| F1-111 | A1 | C-B111 | C-B16 | C-B16 | O | F1-112 | A1 | C-B112 | C-B16 | C-B16 | O |
| F1-113 | A1 | C-B113 | C-B16 | C-B16 | O | F1-114 | A1 | C-B114 | C-B16 | C-B16 | O |
| F1-115 | A1 | C-B115 | C-B16 | C-B16 | O | F1-116 | A1 | C-B116 | C-B16 | C-B16 | O |
| F1-117 | A1 | C-B117 | C-B16 | C-B16 | O | F1-118 | A1 | C-B118 | C-B16 | C-B16 | O |
| F1-119 | A1 | C-B119 | C-B16 | C-B16 | O | F1-120 | A1 | C-B120 | C-B16 | C-B16 | O |
| F1-121 | A1 | C-B121 | C-B16 | C-B16 | O | F1-122 | A1 | C-B122 | C-B16 | C-B16 | O |
| F1-123 | A1 | C-B123 | C-B16 | C-B16 | O | F1-124 | A1 | C-B124 | C-B16 | C-B16 | O |
| F1-125 | A1 | C-B16 | C-B1 | C-B16 | O | F1-126 | A1 | C-B16 | C-B2 | C-B16 | O |
| F1-127 | A1 | C-B16 | C-B3 | C-B16 | O | F1-128 | A1 | C-B16 | C-B4 | C-B16 | O |
| F1-129 | A1 | C-B16 | C-B5 | C-B16 | O | F1-130 | A1 | C-B16 | C-B6 | C-B16 | O |
| F1-131 | A1 | C-B16 | C-B7 | C-B16 | O | F1-132 | A1 | C-B16 | C-B8 | C-B16 | O |
| F1-133 | A1 | C-B16 | C-B9 | C-B16 | O | F1-134 | A1 | C-B16 | C-B10 | C-B16 | O |
| F1-135 | A1 | C-B16 | C-B11 | C-B16 | O | F1-136 | A1 | C-B16 | C-B12 | C-B16 | O |
| F1-137 | A1 | C-B16 | C-B13 | C-B16 | O | F1-138 | A1 | C-B16 | C-B14 | C-B16 | O |
| F1-139 | A1 | C-B16 | C-B15 | C-B16 | O | F1-140 | A1 | C-B16 | C-B16 | C-B16 | O |
| F1-141 | A1 | C-B16 | C-B17 | C-B16 | O | F1-142 | A1 | C-B16 | C-B18 | C-B16 | O |
| F1-143 | A1 | C-B16 | C-B19 | C-B16 | O | F1-144 | A1 | C-B16 | C-B20 | C-B16 | O |
| F1-145 | A1 | C-B16 | C-B21 | C-B16 | O | F1-146 | A1 | C-B16 | C-B22 | C-B16 | O |
| F1-147 | A1 | C-B16 | C-B23 | C-B16 | O | F1-148 | A1 | C-B16 | C-B24 | C-B16 | O |
| F1-149 | A1 | C-B16 | C-B25 | C-B16 | O | F1-150 | A1 | C-B16 | C-B26 | C-B16 | O |
| F1-151 | A1 | C-B16 | C-B27 | C-B16 | O | F1-152 | A1 | C-B16 | C-B28 | C-B16 | O |
| F1-153 | A1 | C-B16 | C-B29 | C-B16 | O | F1-154 | A1 | C-B16 | C-B30 | C-B16 | O |
| F1-155 | A1 | C-B16 | C-B31 | C-B16 | O | F1-156 | A1 | C-B16 | C-B32 | C-B16 | O |
| F1-157 | A1 | C-B16 | C-B33 | C-B16 | O | F1-158 | A1 | C-B16 | C-B34 | C-B16 | O |
| F1-159 | A1 | C-B16 | C-B35 | C-B16 | O | F1-160 | A1 | C-B16 | C-B36 | C-B16 | O |
| F1-161 | A1 | C-B16 | C-B37 | C-B16 | O | F1-162 | A1 | C-B16 | C-B38 | C-B16 | O |
| F1-163 | A1 | C-B16 | C-B39 | C-B16 | O | F1-164 | A1 | C-B16 | C-B40 | C-B16 | O |
| F1-165 | A1 | C-B16 | C-B41 | C-B16 | O | F1-166 | A1 | C-B16 | C-B42 | C-B16 | O |
| F1-167 | A1 | C-B16 | C-B43 | C-B16 | O | F1-168 | A1 | C-B16 | C-B44 | C-B16 | O |
| F1-169 | A1 | C-B16 | C-B45 | C-B16 | O | F1-170 | A1 | C-B16 | C-B46 | C-B16 | O |
| F1-171 | A1 | C-B16 | C-B47 | C-B16 | O | F1-172 | A1 | C-B16 | C-B48 | C-B16 | O |
| F1-173 | A1 | C-B16 | C-B49 | C-B16 | O | F1-174 | A1 | C-B16 | C-B50 | C-B16 | O |
| F1-175 | A1 | C-B16 | C-B51 | C-B16 | O | F1-176 | A1 | C-B16 | C-B52 | C-B16 | O |

-continued

| Compound No. | Y | $X_1$ | $X_2$ | $X_3$ | W | Compound No. | Y | $X_1$ | $X_2$ | $X_3$ | W |
|---|---|---|---|---|---|---|---|---|---|---|---|
| F1-177 | A1 | C-B16 | C-B53 | C-B16 | O | F1-178 | A1 | C-B16 | C-B54 | C-B16 | O |
| F1-179 | A1 | C-B16 | C-B55 | C-B16 | O | F1-180 | A1 | C-B16 | C-B56 | C-B16 | O |
| F1-181 | A1 | C-B16 | C-B57 | C-B16 | O | F1-182 | A1 | C-B16 | C-B58 | C-B16 | O |
| F1-183 | A1 | C-B16 | C-B59 | C-B16 | O | F1-184 | A1 | C-B16 | C-B60 | C-B16 | O |
| F1-185 | A1 | C-B16 | C-B61 | C-B16 | O | F1-186 | A1 | C-B16 | C-B62 | C-B16 | O |
| F1-187 | A1 | C-B16 | C-B63 | C-B16 | O | F1-188 | A1 | C-B16 | C-B64 | C-B16 | O |
| F1-189 | A1 | C-B16 | C-B65 | C-B16 | O | F1-190 | A1 | C-B16 | C-B66 | C-B16 | O |
| F1-191 | A1 | C-B16 | C-B67 | C-B16 | O | F1-192 | A1 | C-B16 | C-B68 | C-B16 | O |
| F1-193 | A1 | C-B16 | C-B69 | C-B16 | O | F1-194 | A1 | C-B16 | C-B70 | C-B16 | O |
| F1-195 | A1 | C-B16 | C-B71 | C-B16 | O | F1-196 | A1 | C-B16 | C-B72 | C-B16 | O |
| F1-197 | A1 | C-B16 | C-B73 | C-B16 | O | F1-198 | A1 | C-B16 | C-B74 | C-B16 | O |
| F1-199 | A1 | C-B16 | C-B75 | C-B16 | O | F1-200 | A1 | C-B16 | C-B76 | C-B16 | O |
| F1-201 | A1 | C-B16 | C-B77 | C-B16 | O | F1-202 | A1 | C-B16 | C-B78 | C-B16 | O |
| F1-203 | A1 | C-B16 | C-B79 | C-B16 | O | F1-204 | A1 | C-B16 | C-B80 | C-B16 | O |
| F1-205 | A1 | C-B16 | C-B81 | C-B16 | O | F1-206 | A1 | C-B16 | C-B82 | C-B16 | O |
| F1-207 | A1 | C-B16 | C-B83 | C-B16 | O | F1-208 | A1 | C-B16 | C-B84 | C-B16 | O |
| F1-209 | A1 | C-B16 | C-B85 | C-B16 | O | F1-210 | A1 | C-B16 | C-B86 | C-B16 | O |
| F1-211 | A1 | C-B16 | C-B87 | C-B16 | O | F1-212 | A1 | C-B16 | C-B88 | C-B16 | O |
| F1-213 | A1 | C-B16 | C-B89 | C-B16 | O | F1-214 | A1 | C-B16 | C-B90 | C-B16 | O |
| F1-215 | A1 | C-B16 | C-B91 | C-B16 | O | F1-216 | A1 | C-B16 | C-B92 | C-B16 | O |
| F1-217 | A1 | C-B16 | C-B93 | C-B16 | O | F1-218 | A1 | C-B16 | C-B94 | C-B16 | O |
| F1-219 | A1 | C-B16 | C-B95 | C-B16 | O | F1-220 | A1 | C-B16 | C-B96 | C-B16 | O |
| F1-221 | A1 | C-B16 | C-B97 | C-B16 | O | F1-222 | A1 | C-B16 | C-B98 | C-B16 | O |
| F1-223 | A1 | C-B16 | C-B99 | C-B16 | O | F1-224 | A1 | C-B16 | C-B100 | C-B16 | O |
| F1-225 | A1 | C-B16 | C-B101 | C-B16 | O | F1-226 | A1 | C-B16 | C-B102 | C-B16 | O |
| F1-227 | A1 | C-B16 | C-B103 | C-B16 | O | F1-228 | A1 | C-B16 | C-B104 | C-B16 | O |
| F1-229 | A1 | C-B16 | C-B105 | C-B16 | O | F1-230 | A1 | C-B16 | C-B106 | C-B16 | O |
| F1-231 | A1 | C-B16 | C-B107 | C-B16 | O | F1-232 | A1 | C-B16 | C-B108 | C-B16 | O |
| F1-233 | A1 | C-B16 | C-B109 | C-B16 | O | F1-234 | A1 | C-B16 | C-B110 | C-B16 | O |
| F1-235 | A1 | C-B16 | C-B111 | C-B16 | O | F1-236 | A1 | C-B16 | C-B112 | C-B16 | O |
| F1-237 | A1 | C-B16 | C-B113 | C-B16 | O | F1-238 | A1 | C-B16 | C-B114 | C-B16 | O |
| F1-239 | A1 | C-B16 | C-B115 | C-B16 | O | F1-240 | A1 | C-B16 | C-B116 | C-B16 | O |
| F1-241 | A1 | C-B16 | C-B117 | C-B16 | O | F1-242 | A1 | C-B16 | C-B118 | C-B16 | O |
| F1-243 | A1 | C-B16 | C-B119 | C-B16 | O | F1-244 | A1 | C-B16 | C-B120 | C-B16 | O |
| F1-245 | A1 | C-B16 | C-B121 | C-B16 | O | F1-246 | A1 | C-B16 | C-B122 | C-B16 | O |
| F1-247 | A1 | C-B16 | C-B123 | C-B16 | O | F1-248 | A1 | C-B16 | C-B124 | C-B16 | O |
| F1-249 | A1 | C-B16 | C-B16 | C-B1 | O | F1-250 | A1 | C-B16 | C-B16 | C-B2 | O |
| F1-251 | A1 | C-B16 | C-B16 | C-B3 | O | F1-252 | A1 | C-B16 | C-B16 | C-B4 | O |
| F1-253 | A1 | C-B16 | C-B16 | C-B5 | O | F1-254 | A1 | C-B16 | C-B16 | C-B6 | O |
| F1-255 | A1 | C-B16 | C-B16 | C-B7 | O | F1-256 | A1 | C-B16 | C-B16 | C-B8 | O |
| F1-257 | A1 | C-B16 | C-B16 | C-B9 | O | F1-258 | A1 | C-B16 | C-B16 | C-B10 | O |
| F1-259 | A1 | C-B16 | C-B16 | C-B11 | O | F1-260 | A1 | C-B16 | C-B16 | C-B12 | O |
| F1-261 | A1 | C-B16 | C-B16 | C-B13 | O | F1-262 | A1 | C-B16 | C-B16 | C-B14 | O |
| F1-263 | A1 | C-B16 | C-B16 | C-B15 | O | F1-264 | A1 | C-B16 | C-B16 | C-B16 | O |
| F1-265 | A1 | C-B16 | C-B16 | C-B17 | O | F1-266 | A1 | C-B16 | C-B16 | C-B18 | O |
| F1-267 | A1 | C-B16 | C-B16 | C-B19 | O | F1-268 | A1 | C-B16 | C-B16 | C-B20 | O |
| F1-269 | A1 | C-B16 | C-B16 | C-B21 | O | F1-270 | A1 | C-B16 | C-B16 | C-B22 | O |
| F1-271 | A1 | C-B16 | C-B16 | C-B23 | O | F1-272 | A1 | C-B16 | C-B16 | C-B24 | O |
| F1-273 | A1 | C-B16 | C-B16 | C-B25 | O | F1-274 | A1 | C-B16 | C-B16 | C-B26 | O |
| F1-275 | A1 | C-B16 | C-B16 | C-B27 | O | F1-276 | A1 | C-B16 | C-B16 | C-B28 | O |
| F1-277 | A1 | C-B16 | C-B16 | C-B29 | O | F1-278 | A1 | C-B16 | C-B16 | C-B30 | O |
| F1-279 | A1 | C-B16 | C-B16 | C-B31 | O | F1-280 | A1 | C-B16 | C-B16 | C-B32 | O |
| F1-281 | A1 | C-B16 | C-B16 | C-B33 | O | F1-282 | A1 | C-B16 | C-B16 | C-B34 | O |
| F1-283 | A1 | C-B16 | C-B16 | C-B35 | O | F1-284 | A1 | C-B16 | C-B16 | C-B36 | O |
| F1-285 | A1 | C-B16 | C-B16 | C-B37 | O | F1-286 | A1 | C-B16 | C-B16 | C-B38 | O |
| F1-287 | A1 | C-B16 | C-B16 | C-B39 | O | F1-288 | A1 | C-B16 | C-B16 | C-B40 | O |
| F1-289 | A1 | C-B16 | C-B16 | C-B41 | O | F1-290 | A1 | C-B16 | C-B16 | C-B42 | O |
| F1-291 | A1 | C-B16 | C-B16 | C-B43 | O | F1-292 | A1 | C-B16 | C-B16 | C-B44 | O |
| F1-293 | A1 | C-B16 | C-B16 | C-B45 | O | F1-294 | A1 | C-B16 | C-B16 | C-B46 | O |
| F1-295 | A1 | C-B16 | C-B16 | C-B47 | O | F1-296 | A1 | C-B16 | C-B16 | C-B48 | O |
| F1-297 | A1 | C-B16 | C-B16 | C-B49 | O | F1-298 | A1 | C-B16 | C-B16 | C-B50 | O |
| F1-299 | A1 | C-B16 | C-B16 | C-B51 | O | F1-300 | A1 | C-B16 | C-B16 | C-B52 | O |
| F1-301 | A1 | C-B16 | C-B16 | C-B53 | O | F1-302 | A1 | C-B16 | C-B16 | C-B54 | O |
| F1-303 | A1 | C-B16 | C-B16 | C-B55 | O | F1-304 | A1 | C-B16 | C-B16 | C-B56 | O |
| F1-305 | A1 | C-B16 | C-B16 | C-B57 | O | F1-306 | A1 | C-B16 | C-B16 | C-B58 | O |
| F1-307 | A1 | C-B16 | C-B16 | C-B59 | O | F1-308 | A1 | C-B16 | C-B16 | C-B60 | O |
| F1-309 | A1 | C-B16 | C-B16 | C-B61 | O | F1-310 | A1 | C-B16 | C-B16 | C-B62 | O |
| F1-311 | A1 | C-B16 | C-B16 | C-B63 | O | F1-312 | A1 | C-B16 | C-B16 | C-B64 | O |
| F1-313 | A1 | C-B16 | C-B16 | C-B65 | O | F1-314 | A1 | C-B16 | C-B16 | C-B66 | O |
| F1-315 | A1 | C-B16 | C-B16 | C-B67 | O | F1-316 | A1 | C-B16 | C-B16 | C-B68 | O |
| F1-317 | A1 | C-B16 | C-B16 | C-B69 | O | F1-318 | A1 | C-B16 | C-B16 | C-B70 | O |
| F1-319 | A1 | C-B16 | C-B16 | C-B71 | O | F1-320 | A1 | C-B16 | C-B16 | C-B72 | O |
| F1-321 | A1 | C-B16 | C-B16 | C-B73 | O | F1-322 | A1 | C-B16 | C-B16 | C-B74 | O |
| F1-323 | A1 | C-B16 | C-B16 | C-B75 | O | F1-324 | A1 | C-B16 | C-B16 | C-B76 | O |
| F1-325 | A1 | C-B16 | C-B16 | C-B77 | O | F1-326 | A1 | C-B16 | C-B16 | C-B78 | O |
| F1-327 | A1 | C-B16 | C-B16 | C-B79 | O | F1-328 | A1 | C-B16 | C-B16 | C-B80 | O |

-continued

| Compound No. | Y | $X_1$ | $X_2$ | $X_3$ | W | Compound No. | Y | $X_1$ | $X_2$ | $X_3$ | W |
|---|---|---|---|---|---|---|---|---|---|---|---|
| F1-329 | A1 | C-B16 | C-B16 | C-B81 | O | F1-330 | A1 | C-B16 | C-B16 | C-B82 | O |
| F1-331 | A1 | C-B16 | C-B16 | C-B83 | O | F1-332 | A1 | C-B16 | C-B16 | C-B84 | O |
| F1-333 | A1 | C-B16 | C-B16 | C-B85 | O | F1-334 | A1 | C-B16 | C-B16 | C-B86 | O |
| F1-335 | A1 | C-B16 | C-B16 | C-B87 | O | F1-336 | A1 | C-B16 | C-B16 | C-B88 | O |
| F1-337 | A1 | C-B16 | C-B16 | C-B89 | O | F1-338 | A1 | C-B16 | C-B16 | C-B90 | O |
| F1-339 | A1 | C-B16 | C-B16 | C-B91 | O | F1-340 | A1 | C-B16 | C-B16 | C-B92 | O |
| F1-341 | A1 | C-B16 | C-B16 | C-B93 | O | F1-342 | A1 | C-B16 | C-B16 | C-B94 | O |
| F1-343 | A1 | C-B16 | C-B16 | C-B95 | O | F1-344 | A1 | C-B16 | C-B16 | C-B96 | O |
| F1-345 | A1 | C-B16 | C-B16 | C-B97 | O | F1-346 | A1 | C-B16 | C-B16 | C-B98 | O |
| F1-347 | A1 | C-B16 | C-B16 | C-B99 | O | F1-348 | A1 | C-B16 | C-B16 | C-B100 | O |
| F1-349 | A1 | C-B16 | C-B16 | C-B101 | O | F1-350 | A1 | C-B16 | C-B16 | C-B102 | O |
| F1-351 | A1 | C-B16 | C-B16 | C-B103 | O | F1-352 | A1 | C-B16 | C-B16 | C-B104 | O |
| F1-353 | A1 | C-B16 | C-B16 | C-B105 | O | F1-354 | A1 | C-B16 | C-B16 | C-B106 | O |
| F1-355 | A1 | C-B16 | C-B16 | C-B107 | O | F1-356 | A1 | C-B16 | C-B16 | C-B108 | O |
| F1-357 | A1 | C-B16 | C-B16 | C-B109 | O | F1-358 | A1 | C-B16 | C-B16 | C-B110 | O |
| F1-359 | A1 | C-B16 | C-B16 | C-B111 | O | F1-360 | A1 | C-B16 | C-B16 | C-B112 | O |
| F1-361 | A1 | C-B16 | C-B16 | C-B113 | O | F1-362 | A1 | C-B16 | C-B16 | C-B114 | O |
| F1-363 | A1 | C-B16 | C-B16 | C-B115 | O | F1-364 | A1 | C-B16 | C-B16 | C-B116 | O |
| F1-365 | A1 | C-B16 | C-B16 | C-B117 | O | F1-366 | A1 | C-B16 | C-B16 | C-B118 | O |
| F1-367 | A1 | C-B16 | C-B16 | C-B119 | O | F1-368 | A1 | C-B16 | C-B16 | C-B120 | O |
| F1-369 | A1 | C-B16 | C-B16 | C-B121 | O | F1-370 | A1 | C-B16 | C-B16 | C-B122 | O |
| F1-371 | A1 | C-B16 | C-B16 | C-B123 | O | F1-372 | A1 | C-B16 | C-B16 | C-B124 | O |
| F1-373 | A2 | C-B16 | C-B1 | C-B16 | O | F1-374 | A2 | C-B16 | C-B6 | C-B16 | O |
| F1-375 | A2 | C-B16 | C-B13 | C-B16 | O | F1-376 | A2 | C-B16 | C-B18 | C-B16 | O |
| F1-377 | A2 | C-B16 | C-B25 | C-B16 | O | F1-378 | A2 | C-B16 | C-B27 | C-B16 | O |
| F1-379 | A2 | C-B16 | C-B30 | C-B16 | O | F1-380 | A2 | C-B16 | C-B32 | C-B16 | O |
| F1-381 | A2 | C-B16 | C-B42 | C-B16 | O | F1-382 | A2 | C-B16 | C-B54 | C-B16 | O |
| F1-383 | A2 | C-B16 | C-B70 | C-B16 | O | F1-384 | A2 | C-B16 | C-B72 | C-B16 | O |
| F1-385 | A2 | C-B16 | C-B73 | C-B16 | O | F1-386 | A2 | C-B16 | C-B74 | C-B16 | O |
| F1-387 | A2 | C-B16 | C-B108 | C-B16 | O | F1-388 | A2 | C-B16 | C-B124 | C-B16 | O |
| F1-389 | A1 | C-B16 | C-B1 | C-B16 | S | F1-390 | A1 | C-B16 | C-B6 | C-B16 | S |
| F1-391 | A1 | C-B16 | C-B13 | C-B16 | S | F1-392 | A1 | C-B16 | C-B18 | C-B16 | S |
| F1-393 | A1 | C-B16 | C-B25 | C-B16 | S | F1-394 | A1 | C-B16 | C-B27 | C-B16 | S |
| F1-395 | A1 | C-B16 | C-B30 | C-B16 | S | F1-396 | A1 | C-B16 | C-B32 | C-B16 | S |
| F1-397 | A1 | C-B16 | C-B42 | C-B16 | S | F1-398 | A1 | C-B16 | C-B54 | C-B16 | S |
| F1-399 | A1 | C-B16 | C-B70 | C-B16 | S | F1-400 | A1 | C-B16 | C-B72 | C-B16 | S |
| F1-401 | A1 | C-B16 | C-B73 | C-B16 | S | F1-402 | A1 | C-B16 | C-B74 | C-B16 | S |
| F1-403 | A1 | C-B16 | C-B108 | C-B16 | S | F1-404 | A1 | C-B16 | C-B124 | C-B16 | S |
| F1-405 | A1 | C-B16 | C-B1 | C-B16 | Se | F1-406 | A1 | C-B16 | C-B6 | C-B16 | Se |
| F1-407 | A1 | C-B16 | C-B13 | C-B16 | Se | F1-408 | A1 | C-B16 | C-B18 | C-B16 | Se |
| F1-409 | A1 | C-B16 | C-B25 | C-B16 | Se | F1-410 | A1 | C-B16 | C-B27 | C-B16 | Se |
| F1-411 | A1 | C-B16 | C-B30 | C-B16 | Se | F1-412 | A1 | C-B16 | C-B32 | C-B16 | Se |
| F1-413 | A1 | C-B16 | C-B42 | C-B16 | Se | F1-414 | A1 | C-B16 | C-B54 | C-B16 | Se |
| F1-415 | A1 | C-B16 | C-B70 | C-B16 | Se | F1-416 | A1 | C-B16 | C-B72 | C-B16 | Se |
| F1-417 | A1 | C-B16 | C-B73 | C-B16 | Se | F1-418 | A1 | C-B16 | C-B74 | C-B16 | Se |
| F1-419 | A1 | C-B16 | C-B108 | C-B16 | Se | F1-420 | A1 | C-B16 | C-B124 | C-B16 | Se |
| F1-421 | A1 | C-B16 | C-B1 | C-B16 | NPh | F1-422 | A1 | C-B16 | C-B6 | C-B16 | NPh |
| F1-423 | A1 | C-B16 | C-B13 | C-B16 | NPh | F1-424 | A1 | C-B16 | C-B18 | C-B16 | NPh |
| F1-425 | A1 | C-B16 | C-B25 | C-B16 | NPh | F1-426 | A1 | C-B16 | C-B27 | C-B16 | NPh |
| F1-427 | A1 | C-B16 | C-B30 | C-B16 | NPh | F1-428 | A1 | C-B16 | C-B32 | C-B16 | NPh |
| F1-429 | A1 | C-B16 | C-B42 | C-B16 | NPh | F1-430 | A1 | C-B16 | C-B54 | C-B16 | NPh |
| F1-431 | A1 | C-B16 | C-B70 | C-B16 | NPh | F1-432 | A1 | C-B16 | C-B72 | C-B16 | NPh |
| F1-433 | A1 | C-B16 | C-B73 | C-B16 | NPh | F1-434 | A1 | C-B16 | C-B74 | C-B16 | NPh |
| F1-435 | A1 | C-B16 | C-B108 | C-B16 | NPh | F1-436 | A1 | C-B16 | C-B124 | C-B16 | NPh; |

wherein Compound F2-1 to Compound F2-160 each have a structure represented by Formula F2':

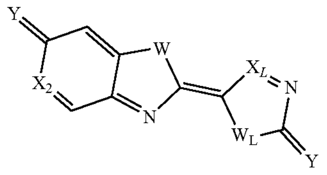

F2' in Formula F2', two Y are the same, and Y, $X_2$, $X_L$, W and $W_L$ are selected from atoms or groups in the following table, respectively:

| Compound No. | Y | $X_2$ | W | $X_L$ | $W_L$ | Compound No. | Y | $X_2$ | W | $X_L$ | $W_L$ |
|---|---|---|---|---|---|---|---|---|---|---|---|
| F2-1 | A1 | C-B1 | O | C-B16 | O | F2-2 | A1 | C-B6 | O | C-B16 | O |
| F2-3 | A1 | C-B13 | O | C-B16 | O | F2-4 | A1 | C-B18 | O | C-B16 | O |
| F2-5 | A1 | C-B25 | O | C-B16 | O | F2-6 | A1 | C-B27 | O | C-B16 | O |
| F2-7 | A1 | C-B30 | O | C-B16 | O | F2-8 | A1 | C-B32 | O | C-B16 | O |
| F2-9 | A1 | C-B42 | O | C-B16 | O | F2-10 | A1 | C-B54 | O | C-B16 | O |
| F2-11 | A1 | C-B70 | O | C-B16 | O | F2-12 | A1 | C-B72 | O | C-B16 | O |
| F2-13 | A1 | C-B73 | O | C-B16 | O | F2-14 | A1 | C-B74 | O | C-B16 | O |
| F2-15 | A1 | C-B108 | O | C-B16 | O | F2-16 | A1 | C-B124 | O | C-B16 | O |
| F2-17 | A1 | C-B1 | O | C-B6 | O | F2-18 | A1 | C-B6 | O | C-B1 | O |
| F2-19 | A1 | C-B13 | O | C-B18 | O | F2-20 | A1 | C-B18 | O | C-B13 | O |
| F2-21 | A1 | C-B25 | O | C-B27 | O | F2-22 | A1 | C-B27 | O | C-B25 | O |
| F2-23 | A1 | C-B30 | O | C-B32 | O | F2-24 | A1 | C-B32 | O | C-B30 | O |
| F2-25 | A1 | C-B42 | O | C-B54 | O | F2-26 | A1 | C-B54 | O | C-B42 | O |
| F2-27 | A1 | C-B70 | O | C-B72 | O | F2-28 | A1 | C-B72 | O | C-B70 | O |
| F2-29 | A1 | C-B73 | O | C-B74 | O | F2-30 | A1 | C-B74 | O | C-B73 | O |
| F2-31 | A1 | C-B108 | O | C-B124 | O | F2-32 | A1 | C-B124 | O | C-B108 | O |
| F2-33 | A1 | C-B1 | S | C-B1 | O | F2-34 | A1 | C-B16 | S | C-B6 | O |
| F2-35 | A1 | C-B13 | S | C-B13 | O | F2-36 | A1 | C-B18 | S | C-B18 | O |
| F2-37 | A1 | C-B25 | S | C-B25 | O | F2-38 | A1 | C-B27 | S | C-B27 | O |
| F2-39 | A1 | C-B30 | S | C-B30 | O | F2-40 | A1 | C-B32 | S | C-B32 | O |
| F2-41 | A1 | C-B42 | S | C-B42 | O | F2-42 | A1 | C-B54 | S | C-B54 | O |
| F2-43 | A1 | C-B70 | S | C-B70 | O | F2-44 | A1 | C-B72 | S | C-B72 | O |
| F2-45 | A1 | C-B73 | S | C-B73 | O | F2-46 | A1 | C-B74 | S | C-B74 | O |
| F2-47 | A1 | C-B108 | S | C-B108 | O | F2-48 | A1 | C-B124 | S | C-B124 | O |
| F2-49 | A1 | C-B1 | Se | C-B1 | O | F2-50 | A1 | C-B6 | Se | C-B6 | O |
| F2-51 | A1 | C-B13 | Se | C-B13 | O | F2-52 | A1 | C-B18 | Se | C-B18 | O |
| F2-53 | A1 | C-B25 | Se | C-B25 | O | F2-54 | A1 | C-B27 | Se | C-B27 | O |
| F2-55 | A1 | C-B30 | Se | C-B30 | O | F2-56 | A1 | C-B32 | Se | C-B32 | O |
| F2-57 | A1 | C-B42 | Se | C-B42 | O | F2-58 | A1 | C-B54 | Se | C-B54 | O |
| F2-59 | A1 | C-B70 | Se | C-B70 | O | F2-60 | A1 | C-B72 | Se | C-B72 | O |
| F2-61 | A1 | C-B73 | Se | C-B73 | O | F2-62 | A1 | C-B74 | Se | C-B74 | O |
| F2-63 | A1 | C-B108 | Se | C-B108 | O | F2-64 | A1 | C-B124 | Se | C-B124 | O |
| F2-65 | A1 | C-B1 | NPh | C-B1 | O | F2-66 | A1 | C-B6 | NPh | C-B6 | O |
| F2-67 | A1 | C-B13 | NPh | C-B13 | O | F2-68 | A1 | C-B18 | NPh | C-B18 | O |
| F2-69 | A1 | C-B25 | NPh | C-B25 | O | F2-70 | A1 | C-B27 | NPh | C-B27 | O |
| F2-71 | A1 | C-B30 | NPh | C-B30 | O | F2-72 | A1 | C-B32 | NPh | C-B32 | O |
| F2-73 | A1 | C-B42 | NPh | C-B42 | O | F2-74 | A1 | C-B54 | NPh | C-B54 | O |
| F2-75 | A1 | C-B70 | NPh | C-B70 | O | F2-76 | A1 | C-B72 | NPh | C-B72 | O |
| F2-77 | A1 | C-B73 | NPh | C-B73 | O | F2-78 | A1 | C-B74 | NPh | C-B74 | O |
| F2-79 | A1 | C-B108 | NPh | C-B108 | O | F2-80 | A1 | C-B124 | NPh | C-B124 | O |
| F2-81 | A1 | C-B16 | O | C-B1 | O | F2-82 | A1 | C-B16 | O | C-B6 | O |
| F2-83 | A1 | C-B16 | O | C-B13 | O | F2-84 | A1 | C-B16 | O | C-B18 | O |
| F2-85 | A1 | C-B16 | O | C-B25 | O | F2-86 | A1 | C-B16 | O | C-B27 | O |
| F2-87 | A1 | C-B16 | O | C-B30 | O | F2-88 | A1 | C-B16 | O | C-B32 | O |
| F2-89 | A1 | C-B16 | O | C-B42 | O | F2-90 | A1 | C-B16 | O | C-B54 | O |
| F2-91 | A1 | C-B16 | O | C-B70 | O | F2-92 | A1 | C-B16 | O | C-B72 | O |
| F2-93 | A1 | C-B16 | O | C-B73 | O | F2-94 | A1 | C-B16 | O | C-B74 | O |
| F2-95 | A1 | C-B16 | O | C-B108 | O | F2-96 | A1 | C-B16 | O | C-B124 | O |
| F2-97 | A1 | C-B1 | O | C-B1 | S | F2-98 | A1 | C-B6 | O | C-B6 | S |
| F2-99 | A1 | C-B13 | O | C-B13 | S | F2-100 | A1 | C-B18 | O | C-B18 | S |
| F2-101 | A1 | C-B25 | O | C-B25 | S | F2-102 | A1 | C-B27 | O | C-B27 | S |
| F2-103 | A1 | C-B30 | O | C-B30 | S | F2-104 | A1 | C-B32 | O | C-B32 | S |
| F2-105 | A1 | C-B42 | O | C-B42 | S | F2-106 | A1 | C-B54 | O | C-B54 | S |
| F2-107 | A1 | C-B70 | O | C-B70 | S | F2-108 | A1 | C-B72 | O | C-B72 | S |
| F2-109 | A1 | C-B73 | O | C-B73 | S | F2-110 | A1 | C-B74 | O | C-B74 | S |
| F2-111 | A1 | C-B108 | O | C-B108 | S | F2-112 | A1 | C-B124 | O | C-B124 | S |
| F2-113 | A1 | C-B1 | O | C-B1 | Se | F2-114 | A1 | C-B6 | O | C-B6 | Se |
| F2-115 | A1 | C-B13 | O | C-B13 | Se | F2-116 | A1 | C-B18 | O | C-B18 | Se |
| F2-117 | A1 | C-B25 | O | C-B25 | Se | F2-118 | A1 | C-B27 | O | C-B27 | Se |
| F2-119 | A1 | C-B30 | O | C-B30 | Se | F2-120 | A1 | C-B32 | O | C-B32 | Se |
| F2-121 | A1 | C-B42 | O | C-B42 | Se | F2-122 | A1 | C-B54 | O | C-B54 | Se |
| F2-123 | A1 | C-B70 | O | C-B70 | Se | F2-124 | A1 | C-B72 | O | C-B72 | Se |
| F2-125 | A1 | C-B73 | O | C-B73 | Se | F2-126 | A1 | C-B74 | O | C-B74 | Se |
| F2-127 | A1 | C-B108 | O | C-B108 | Se | F2-128 | A1 | C-B124 | O | C-B124 | Se |
| F2-129 | A1 | C-B1 | O | C-B1 | NPh | F2-130 | A1 | C-B6 | O | C-B6 | NPh |
| F2-131 | A1 | C-B13 | O | C-B13 | NPh | F2-132 | A1 | C-B18 | O | C-B18 | NPh |
| F2-133 | A1 | C-B25 | O | C-B25 | NPh | F2-134 | A1 | C-B27 | O | C-B27 | NPh |
| F2-135 | A1 | C-B30 | O | C-B30 | NPh | F2-136 | A1 | C-B32 | O | C-B32 | NPh |
| F2-137 | A1 | C-B42 | O | C-B42 | NPh | F2-138 | A1 | C-B54 | O | C-B54 | NPh |
| F2-139 | A1 | C-B70 | O | C-B70 | NPh | F2-140 | A1 | C-B72 | O | C-B72 | NPh |
| F2-141 | A1 | C-B73 | O | C-B73 | NPh | F2-142 | A1 | C-B74 | O | C-B74 | NPh |
| F2-143 | A1 | C-B108 | O | C-B108 | NPh | F2-144 | A1 | C-B124 | O | C-B124 | NPh |
| F2-145 | A2 | C-B1 | O | C-B6 | O | F2-146 | A2 | C-B6 | O | C-B1 | O |
| F2-147 | A2 | C-B13 | O | C-B18 | O | F2-148 | A2 | C-B18 | O | C-B13 | O |
| F2-149 | A2 | C-B25 | O | C-B27 | O | F2-150 | A2 | C-B27 | O | C-B25 | O |
| F2-151 | A2 | C-B30 | O | C-B32 | O | F2-152 | A2 | C-B32 | O | C-B30 | O |
| F2-153 | A2 | C-B42 | O | C-B54 | O | F2-154 | A2 | C-B54 | O | C-B42 | O |
| F2-155 | A2 | C-B70 | O | C-B72 | O | F2-156 | A2 | C-B72 | O | C-B70 | O |

-continued

| Compound No. | Y | $X_2$ | W | $X_L$ | $W_L$ | Compound No. | Y | $X_2$ | W | $X_L$ | $W_L$ |
|---|---|---|---|---|---|---|---|---|---|---|---|
| F2-157 | A2 | C-B73 | O | C-B74 | O | F2-158 | A2 | C-B74 | O | C-B73 | O |
| F2-159 | A2 | C-B108 | O | C-B124 | O | F2-160 | A2 | C-B124 | O | C-B108 | O; |

wherein Compound F3-1 to Compound F3-160 each have a structure represented by

F3'

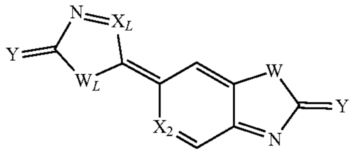

in Formula F3', two Y are the same, and Y, $X_2$, $X_L$, W and $W_L$ are selected from atoms or groups in the following table, respectively:

| Compound No. | Y | $X_2$ | W | $X_L$ | $W_L$ | Compound No. | Y | $X_2$ | W | $X_L$ | $W_L$ |
|---|---|---|---|---|---|---|---|---|---|---|---|
| F3-1 | A1 | C-B1 | O | C-B16 | O | F3-2 | A1 | C-B6 | O | C-B16 | O |
| F3-3 | A1 | C-B13 | O | C-B16 | O | F3-4 | A1 | C-B18 | O | C-B16 | O |
| F3-5 | A1 | C-B25 | O | C-B16 | O | F3-6 | A1 | C-B27 | O | C-B16 | O |
| F3-7 | A1 | C-B30 | O | C-B16 | O | F3-8 | A1 | C-B32 | O | C-B16 | O |
| F3-9 | A1 | C-B42 | O | C-B16 | O | F3-10 | A1 | C-B54 | O | C-B16 | O |
| F3-11 | A1 | C-B70 | O | C-B16 | O | F3-12 | A1 | C-B72 | O | C-B16 | O |
| F3-13 | A1 | C-B73 | O | C-B16 | O | F3-14 | A1 | C-B74 | O | C-B16 | O |
| F3-15 | A1 | C-B108 | O | C-B16 | O | F3-16 | A1 | C-B124 | O | C-B16 | O |
| F3-17 | A1 | C-B1 | O | C-B6 | O | F3-18 | A1 | C-B6 | O | C-B1 | O |
| F3-19 | A1 | C-B13 | O | C-B18 | O | F3-20 | A1 | C-B18 | O | C-B13 | O |
| F3-21 | A1 | C-B25 | O | C-B27 | O | F3-22 | A1 | C-B27 | O | C-B25 | O |
| F3-23 | A1 | C-B30 | O | C-B32 | O | F3-24 | A1 | C-B32 | O | C-B30 | O |
| F3-25 | A1 | C-B42 | O | C-B54 | O | F3-26 | A1 | C-B54 | O | C-B42 | O |
| F3-27 | A1 | C-B70 | O | C-B72 | O | F3-28 | A1 | C-B72 | O | C-B70 | O |
| F3-29 | A1 | C-B73 | O | C-B74 | O | F3-30 | A1 | C-B74 | O | C-B73 | O |
| F3-31 | A1 | C-B108 | O | C-B124 | O | F3-32 | A1 | C-B124 | O | C-B108 | O |
| F3-33 | A1 | C-B1 | S | C-B1 | O | F3-34 | A1 | C-B6 | S | C-B6 | O |
| F3-35 | A1 | C-B13 | S | C-B13 | O | F3-36 | A1 | C-B18 | S | C-B18 | O |
| F3-37 | A1 | C-B25 | S | C-B25 | O | F3-38 | A1 | C-B27 | S | C-B27 | O |
| F3-39 | A1 | C-B30 | S | C-B30 | O | F3-40 | A1 | C-B32 | S | C-B32 | O |
| F3-41 | A1 | C-B42 | S | C-B42 | O | F3-42 | A1 | C-B54 | S | C-B54 | O |
| F3-43 | A1 | C-B70 | S | C-B70 | O | F3-44 | A1 | C-B72 | S | C-B72 | O |
| F3-45 | A1 | C-B73 | S | C-B73 | O | F3-46 | A1 | C-B74 | S | C-B74 | O |
| F3-47 | A1 | C-B108 | S | C-B108 | O | F3-48 | A1 | C-B124 | S | C-B124 | O |
| F3-49 | A1 | C-B1 | Se | C-B1 | O | F3-50 | A1 | C-B6 | Se | C-B6 | O |
| F3-51 | A1 | C-B13 | Se | C-B13 | O | F3-52 | A1 | C-B18 | Se | C-B18 | O |
| F3-53 | A1 | C-B25 | Se | C-B25 | O | F3-54 | A1 | C-B27 | Se | C-B27 | O |
| F3-55 | A1 | C-B30 | Se | C-B30 | O | F3-56 | A1 | C-B32 | Se | C-B32 | O |
| F3-57 | A1 | C-B42 | Se | C-B42 | O | F3-58 | A1 | C-B54 | Se | C-B54 | O |
| F3-59 | A1 | C-B70 | Se | C-B70 | O | F3-60 | A1 | C-B72 | Se | C-B72 | O |
| F3-61 | A1 | C-B73 | Se | C-B73 | O | F3-62 | A1 | C-B74 | Se | C-B74 | O |
| F3-63 | A1 | C-B108 | Se | C-B108 | O | F3-64 | A1 | C-B124 | Se | C-B124 | O |
| F3-65 | A1 | C-B1 | NPh | C-B1 | O | F3-66 | A1 | C-B6 | NPh | C-B6 | O |
| F3-67 | A1 | C-B13 | NPh | C-B13 | O | F3-68 | A1 | C-B18 | NPh | C-B18 | O |
| F3-69 | A1 | C-B25 | NPh | C-B25 | O | F3-70 | A1 | C-B27 | NPh | C-B27 | O |
| F3-71 | A1 | C-B30 | NPh | C-B30 | O | F3-72 | A1 | C-B32 | NPh | C-B32 | O |
| F3-73 | A1 | C-B42 | NPh | C-B42 | O | F3-74 | A1 | C-B54 | NPh | C-B54 | O |
| F3-75 | A1 | C-B70 | NPh | C-B70 | O | F3-76 | A1 | C-B72 | NPh | C-B72 | O |
| F3-77 | A1 | C-B73 | NPh | C-B73 | O | F3-78 | A1 | C-B74 | NPh | C-B74 | O |
| F3-79 | A1 | C-B108 | NPh | C-B108 | O | F3-80 | A1 | C-B124 | NPh | C-B124 | O |
| F3-81 | A1 | C-B16 | O | C-B1 | O | F3-82 | A1 | C-B16 | O | C-B6 | O |
| F3-83 | A1 | C-B16 | O | C-B13 | O | F3-84 | A1 | C-B16 | O | C-B18 | O |
| F3-85 | A1 | C-B16 | O | C-B25 | O | F3-86 | A1 | C-B16 | O | C-B27 | O |
| F3-87 | A1 | C-B16 | O | C-B30 | O | F3-88 | A1 | C-B16 | O | C-B32 | O |
| F3-89 | A1 | C-B16 | O | C-B42 | O | F3-90 | A1 | C-B16 | O | C-B54 | O |
| F3-91 | A1 | C-B16 | O | C-B70 | O | F3-92 | A1 | C-B16 | O | C-B72 | O |
| F3-93 | A1 | C-B16 | O | C-B73 | O | F3-94 | A1 | C-B16 | O | C-B74 | O |
| F3-95 | A1 | C-B16 | O | C-B108 | O | F3-96 | A1 | C-B16 | O | C-B124 | O |

-continued

| Compound No. | Y | $X_2$ | W | $X_L$ | $W_L$ | Compound No. | Y | $X_2$ | W | $X_L$ | $W_L$ |
|---|---|---|---|---|---|---|---|---|---|---|---|
| F3-97 | A1 | C-B1 | O | C-B1 | S | F3-98 | A1 | C-B6 | O | C-B6 | S |
| F3-99 | A1 | C-B13 | O | C-B13 | S | F3-100 | A1 | C-B18 | O | C-B18 | S |
| F3-101 | A1 | C-B25 | O | C-B25 | S | F3-102 | A1 | C-B27 | O | C-B27 | S |
| F3-103 | A1 | C-B30 | O | C-B30 | S | F3-104 | A1 | C-B32 | O | C-B32 | S |
| F3-105 | A1 | C-B42 | O | C-B42 | S | F3-106 | A1 | C-B54 | O | C-B54 | S |
| F3-107 | A1 | C-B70 | O | C-B70 | S | F3-108 | A1 | C-B72 | O | C-B72 | S |
| F3-109 | A1 | C-B73 | O | C-B73 | S | F3-110 | A1 | C-B74 | O | C-B74 | S |
| F3-111 | A1 | C-B108 | O | C-B108 | S | F3-112 | A1 | C-B124 | O | C-B124 | S |
| F3-113 | A1 | C-B1 | O | C-B1 | Se | F3-114 | A1 | C-B6 | O | C-B6 | Se |
| F3-115 | A1 | C-B13 | O | C-B13 | Se | F3-116 | A1 | C-B18 | O | C-B18 | Se |
| F3-117 | A1 | C-B25 | O | C-B25 | Se | F3-118 | A1 | C-B27 | O | C-B27 | Se |
| F3-119 | A1 | C-B30 | O | C-B30 | Se | F3-120 | A1 | C-B32 | O | C-B32 | Se |
| F3-121 | A1 | C-B42 | O | C-B42 | Se | F3-122 | A1 | C-B54 | O | C-B54 | Se |
| F3-123 | A1 | C-B70 | O | C-B70 | Se | F3-124 | A1 | C-B72 | O | C-B72 | Se |
| F3-125 | A1 | C-B73 | O | C-B73 | Se | F3-126 | A1 | C-B74 | O | C-B74 | Se |
| F3-127 | A1 | C-B108 | O | C-B108 | Se | F3-128 | A1 | C-B124 | O | C-B124 | Se |
| F3-129 | A1 | C-B1 | O | C-B1 | NPh | F3-130 | A1 | C-B6 | O | C-B6 | NPh |
| F3-131 | A1 | C-B13 | O | C-B13 | NPh | F3-132 | A1 | C-B18 | O | C-B18 | NPh |
| F3-133 | A1 | C-B25 | O | C-B25 | NPh | F3-134 | A1 | C-B27 | O | C-B27 | NPh |
| F3-135 | A1 | C-B30 | O | C-B30 | NPh | F3-136 | A1 | C-B32 | O | C-B32 | NPh |
| F3-137 | A1 | C-B42 | O | C-B42 | NPh | F3-138 | A1 | C-B54 | O | C-B54 | NPh |
| F3-139 | A1 | C-B70 | O | C-B70 | NPh | F3-140 | A1 | C-B72 | O | C-B72 | NPh |
| F3-141 | A1 | C-B73 | O | C-B73 | NPh | F3-142 | A1 | C-B74 | O | C-B74 | NPh |
| F3-143 | A1 | C-B108 | O | C-B108 | NPh | F3-144 | A1 | C-B124 | O | C-B124 | NPh |
| F3-145 | A2 | C-B1 | O | C-B6 | O | F3-146 | A2 | C-B6 | O | C-B1 | O |
| F3-147 | A2 | C-B13 | O | C-B18 | O | F3-148 | A2 | C-B18 | O | C-B13 | O |
| F3-149 | A2 | C-B25 | O | C-B27 | O | F3-150 | A2 | C-B27 | O | C-B25 | O |
| F3-151 | A2 | C-B30 | O | C-B32 | O | F3-152 | A2 | C-B32 | O | C-B30 | O |
| F3-153 | A2 | C-B42 | O | C-B54 | O | F3-154 | A2 | C-B54 | O | C-B42 | O |
| F3-155 | A2 | C-B70 | O | C-B72 | O | F3-156 | A2 | C-B72 | O | C-B70 | O |
| F3-157 | A2 | C-B73 | O | C-B74 | O | F3-158 | A2 | C-B74 | O | C-B73 | O |
| F3-159 | A2 | C-B108 | O | C-B124 | O | F3-160 | A2 | C-B124 | O | C-B108 | O; |

wherein Compound F4-1 to Compound F4-96 each have a structure represented by Formula F4':

F4'

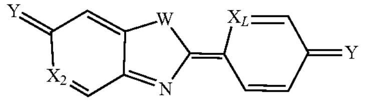

in Formula F4', two Y are the same and Y, $X_2$, $X_L$ and W are selected from atoms or groups in the following table, respectively:

| Compound No. | Y | $X_2$ | W | $X_L$ | Compound No. | Y | $X_2$ | W | $X_L$ |
|---|---|---|---|---|---|---|---|---|---|
| F4-1 | A1 | C-B1 | O | C-B16 | F4-2 | A1 | C-B6 | O | C-B16 |
| F4-3 | A1 | C-B13 | O | C-B16 | F4-4 | A1 | C-B18 | O | C-B16 |
| F4-5 | A1 | C-B25 | O | C-B16 | F4-6 | A1 | C-B27 | O | C-B16 |
| F4-7 | A1 | C-B30 | O | C-B16 | F4-8 | A1 | C-B32 | O | C-B16 |
| F4-9 | A1 | C-B42 | O | C-B16 | F4-10 | A1 | C-B54 | O | C-B16 |
| F4-11 | A1 | C-B70 | O | C-B16 | F4-12 | A1 | C-B72 | O | C-B16 |
| F4-13 | A1 | C-B73 | O | C-B16 | F4-14 | A1 | C-B74 | O | C-B16 |
| F4-15 | A1 | C-B108 | O | C-B16 | F4-16 | A1 | C-B124 | O | C-B16 |
| F4-17 | A1 | C-B1 | O | C-B6 | F4-18 | A1 | C-B6 | O | C-B1 |
| F4-19 | A1 | C-B13 | O | C-B18 | F4-20 | A1 | C-B18 | O | C-B13 |
| F4-21 | A1 | C-B25 | O | C-B27 | F4-22 | A1 | C-B27 | O | C-B25 |
| F4-23 | A1 | C-B30 | O | C-B32 | F4-24 | A1 | C-B32 | O | C-B30 |
| F4-25 | A1 | C-B42 | O | C-B54 | F4-26 | A1 | C-B54 | O | C-B42 |
| F4-27 | A1 | C-B70 | O | C-B72 | F4-28 | A1 | C-B72 | O | C-B70 |
| F4-29 | A1 | C-B73 | O | C-B74 | F4-30 | A1 | C-B74 | O | C-B73 |
| F4-31 | A1 | C-B108 | O | C-B124 | F4-32 | A1 | C-B124 | O | C-B108 |
| F4-33 | A1 | C-B1 | S | C-B1 | F4-34 | A1 | C-B6 | S | C-B6 |
| F4-35 | A1 | C-B13 | S | C-B13 | F4-36 | A1 | C-B18 | S | C-B18 |
| F4-37 | A1 | C-B25 | S | C-B25 | F4-38 | A1 | C-B27 | S | C-B27 |
| F4-39 | A1 | C-B30 | S | C-B30 | F4-40 | A1 | C-B32 | S | C-B32 |
| F4-41 | A1 | C-B42 | S | C-B42 | F4-42 | A1 | C-B54 | S | C-B54 |

-continued

| Compound No. | Y | $X_2$ | W | $X_L$ | Compound No. | Y | $X_2$ | W | $X_L$ |
|---|---|---|---|---|---|---|---|---|---|
| F4-43 | A1 | C-B70 | S | C-B70 | F4-44 | A1 | C-B72 | S | C-B72 |
| F4-45 | A1 | C-B73 | S | C-B73 | F4-46 | A1 | C-B74 | S | C-B74 |
| F4-47 | A1 | C-B108 | S | C-B108 | F4-48 | A1 | C-B124 | S | C-B124 |
| F4-49 | A1 | C-B1 | Se | C-B1 | F4-50 | A1 | C-B6 | Se | C-B6 |
| F4-51 | A1 | C-B13 | Se | C-B13 | F4-52 | A1 | C-B18 | Se | C-B18 |
| F4-53 | A1 | C-B25 | Se | C-B25 | F4-54 | A1 | C-B27 | Se | C-B27 |
| F4-55 | A1 | C-B30 | Se | C-B30 | F4-56 | A1 | C-B32 | Se | C-B32 |
| F4-57 | A1 | C-B42 | Se | C-B42 | F4-58 | A1 | C-B54 | Se | C-B54 |
| F4-59 | A1 | C-B70 | Se | C-B70 | F4-60 | A1 | C-B72 | Se | C-B72 |
| F4-61 | A1 | C-B73 | Se | C-B73 | F4-62 | A1 | C-B74 | Se | C-B74 |
| F4-63 | A1 | C-B108 | Se | C-B108 | F4-64 | A1 | C-B124 | Se | C-B124 |
| F4-65 | A1 | C-B1 | NPh | C-B1 | F4-66 | A1 | C-B6 | NPh | C-B6 |
| F4-67 | A1 | C-B13 | NPh | C-B13 | F4-68 | A1 | C-B18 | NPh | C-B18 |
| F4-69 | A1 | C-B25 | NPh | C-B25 | F4-70 | A1 | C-B27 | NPh | C-B27 |
| F4-71 | A1 | C-B30 | NPh | C-B30 | F4-72 | A1 | C-B32 | NPh | C-B32 |
| F4-73 | A1 | C-B42 | NPh | C-B42 | F4-74 | A1 | C-B54 | NPh | C-B54 |
| F4-75 | A1 | C-B70 | NPh | C-B70 | F4-76 | A1 | C-B72 | NPh | C-B72 |
| F4-77 | A1 | C-B73 | NPh | C-B73 | F4-78 | A1 | C-B74 | NPh | C-B74 |
| F4-79 | A1 | C-B108 | NPh | C-B108 | F4-80 | A1 | C-B124 | NPh | C-B124 |
| F4-81 | A2 | C-B1 | O | C-B6 | F4-82 | A2 | C-B6 | O | C-B1 |
| F4-83 | A2 | C-B13 | O | C-B18 | F4-84 | A2 | C-B18 | O | C-B13 |
| F4-85 | A2 | C-B25 | O | C-B27 | F4-86 | A2 | C-B27 | O | C-B25 |
| F4-87 | A2 | C-B30 | O | C-B32 | F4-88 | A2 | C-B32 | O | C-B30 |
| F4-89 | A2 | C-B42 | O | C-B54 | F4-90 | A2 | C-B54 | O | C-B42 |
| F4-91 | A2 | C-B70 | O | C-B72 | F4-92 | A2 | C-B72 | O | C-B70 |
| F4-93 | A2 | C-B73 | O | C-B74 | F4-94 | A2 | C-B74 | O | C-B73 |
| F4-95 | A2 | C-B108 | O | C-B124 | F4-96 | A2 | C-B124 | O | C-B108; |

wherein Compound F5-1 to Compound F5-96 each have a structure represented by Formula F5':

F5'

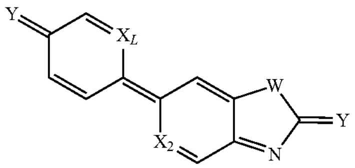

in Formula F5', two Y are the same, and Y, $X_2$, $X_L$ and W are selected from atoms or groups in the following table, respectively:

| Compound No. | Y | $X_2$ | W | $X_L$ | Compound No. | Y | $X_2$ | W | $X_L$ |
|---|---|---|---|---|---|---|---|---|---|
| F5-1 | A1 | C-B1 | O | C-B16 | F5-2 | A1 | C-B6 | O | C-B16 |
| F5-3 | A1 | C-B13 | O | C-B16 | F5-4 | A1 | C-B18 | O | C-B16 |
| F5-5 | A1 | C-B25 | O | C-B16 | F5-6 | A1 | C-B27 | O | C-B16 |
| F5-7 | A1 | C-B30 | O | C-B16 | F5-8 | A1 | C-B32 | O | C-B16 |
| F5-9 | A1 | C-B42 | O | C-B16 | F5-10 | A1 | C-B54 | O | C-B16 |
| F5-11 | A1 | C-B70 | O | C-B16 | F5-12 | A1 | C-B72 | O | C-B16 |
| F5-13 | A1 | C-B73 | O | C-B16 | F5-14 | A1 | C-B74 | O | C-B16 |
| F5-15 | A1 | C-B108 | O | C-B16 | F5-16 | A1 | C-B124 | O | C-B16 |
| F5-17 | A1 | C-B1 | O | C-B6 | F5-18 | A1 | C-B6 | O | C-B1 |
| F5-19 | A1 | C-B13 | O | C-B18 | F5-20 | A1 | C-B18 | O | C-B13 |
| F5-21 | A1 | C-B25 | O | C-B27 | F5-22 | A1 | C-B27 | O | C-B25 |
| F5-23 | A1 | C-B30 | O | C-B32 | F5-24 | A1 | C-B32 | O | C-B30 |
| F5-25 | A1 | C-B42 | O | C-B54 | F5-26 | A1 | C-B54 | O | C-B42 |
| F5-27 | A1 | C-B70 | O | C-B72 | F5-28 | A1 | C-B72 | O | C-B70 |
| F5-29 | A1 | C-B73 | O | C-B74 | F5-30 | A1 | C-B74 | O | C-B73 |
| F5-31 | A1 | C-B108 | O | C-B124 | F5-32 | A1 | C-B124 | O | C-B108 |
| F5-33 | A1 | C-B1 | S | C-B1 | F5-34 | A1 | C-B6 | S | C-B6 |
| F5-35 | A1 | C-B13 | S | C-B13 | F5-36 | A1 | C-B18 | S | C-B18 |
| F5-37 | A1 | C-B25 | S | C-B25 | F5-38 | A1 | C-B27 | S | C-B27 |
| F5-39 | A1 | C-B30 | S | C-B30 | F5-40 | A1 | C-B32 | S | C-B32 |
| F5-41 | A1 | C-B42 | S | C-B42 | F5-42 | A1 | C-B54 | S | C-B54 |
| F5-43 | A1 | C-B70 | S | C-B70 | F5-44 | A1 | C-B72 | S | C-B72 |
| F5-45 | A1 | C-B73 | S | C-B73 | F5-46 | A1 | C-B74 | S | C-B74 |

-continued

| Compound No. | Y | $X_2$ | W | $X_L$ | Compound No. | Y | $X_2$ | W | $X_L$ |
|---|---|---|---|---|---|---|---|---|---|
| F5-47 | A1 | C-B108 | S | C-B108 | F5-48 | A1 | C-B124 | S | C-B124 |
| F5-49 | A1 | C-B1 | Se | C-B1 | F5-50 | A1 | C-B6 | Se | C-B6 |
| F5-51 | A1 | C-B13 | Se | C-B13 | F5-52 | A1 | C-B18 | Se | C-B18 |
| F5-53 | A1 | C-B25 | Se | C-B25 | F5-54 | A1 | C-B27 | Se | C-B27 |
| F5-55 | A1 | C-B30 | Se | C-B30 | F5-56 | A1 | C-B32 | Se | C-B32 |
| F5-57 | A1 | C-B42 | Se | C-B42 | F5-58 | A1 | C-B54 | Se | C-B54 |
| F5-59 | A1 | C-B70 | Se | C-B70 | F5-60 | A1 | C-B72 | Se | C-B72 |
| F5-61 | A1 | C-B73 | Se | C-B73 | F5-62 | A1 | C-B74 | Se | C-B74 |
| F5-63 | A1 | C-B108 | Se | C-B108 | F5-64 | A1 | C-B124 | Se | C-B124 |
| F5-65 | A1 | C-B1 | NPh | C-B1 | F5-66 | A1 | C-B6 | NPh | C-B6 |
| F5-67 | A1 | C-B13 | NPh | C-B13 | F5-68 | A1 | C-B18 | NPh | C-B18 |
| F5-69 | A1 | C-B25 | NPh | C-B25 | F5-70 | A1 | C-B27 | NPh | C-B27 |
| F5-71 | A1 | C-B30 | NPh | C-B30 | F5-72 | A1 | C-B32 | NPh | C-B32 |
| F5-73 | A1 | C-B42 | NPh | C-B42 | F5-74 | A1 | C-B54 | NPh | C-B54 |
| F5-75 | A1 | C-B70 | NPh | C-B70 | F5-76 | A1 | C-B72 | NPh | C-B72 |
| F5-77 | A1 | C-B73 | NPh | C-B73 | F5-78 | A1 | C-B74 | NPh | C-B74 |
| F5-79 | A1 | C-B108 | NPh | C-B108 | F5-80 | A1 | C-B124 | NPh | C-B124 |
| F5-81 | A2 | C-B1 | O | C-B6 | F5-82 | A2 | C-B6 | O | C-B1 |
| F5-83 | A2 | C-B13 | O | C-B18 | F5-84 | A2 | C-B18 | O | C-B13 |
| F5-85 | A2 | C-B25 | O | C-B27 | F5-86 | A2 | C-B27 | O | C-B25 |
| F5-87 | A2 | C-B30 | O | C-B32 | F5-88 | A2 | C-B32 | O | C-B30 |
| F5-89 | A2 | C-B42 | O | C-B54 | F5-90 | A2 | C-B54 | O | C-B42 |
| F5-91 | A2 | C-B70 | O | C-B72 | F5-92 | A2 | C-B72 | O | C-B70 |
| F5-93 | A2 | C-B73 | O | C-B74 | F5-94 | A2 | C-B74 | O | C-B73 |
| F5-95 | A2 | C-B108 | O | C-B124 | F5-96 | A2 | C-B124 | O | C-B108; |

wherein Compound F6-1 to Compound F6-96 each have a structure represented by Formula F6':

F6'

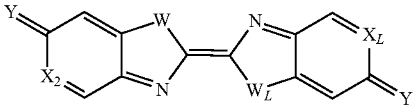

in Formula F6', two Y are the same, $X_2$ and $X_L$ are the same, and Y, $X_2$, $X_L$, W and $W_L$ are selected from atoms or groups in the following table, respectively:

| Compound No. | Y | W | $X_2 = X_L$ | $W_L$ | Compound No. | Y | W | $X_2 = X_L$ | $W_L$ |
|---|---|---|---|---|---|---|---|---|---|
| F6-1 | A1 | O | C-B1 | O | F6-2 | A1 | O | C-B6 | O |
| F6-3 | A1 | O | C-B13 | O | F6-4 | A1 | O | C-B18 | O |
| F6-5 | A1 | O | C-B25 | O | F6-6 | A1 | O | C-B27 | O |
| F6-7 | A1 | O | C-B30 | O | F6-8 | A1 | O | C-B32 | O |
| F6-9 | A1 | O | C-B42 | O | F6-10 | A1 | O | C-B54 | O |
| F6-11 | A1 | O | C-B70 | O | F6-12 | A1 | O | C-B72 | O |
| F6-13 | A1 | O | C-B73 | O | F6-14 | A1 | O | C-B74 | O |
| F6-15 | A1 | O | C-B108 | O | F6-16 | A1 | O | C-B124 | O |
| F6-17 | A1 | S | C-B1 | O | F6-18 | A1 | S | C-B6 | O |
| F6-19 | A1 | S | C-B13 | O | F6-20 | A1 | S | C-B18 | O |
| F6-21 | A1 | S | C-B25 | O | F6-22 | A1 | S | C-B27 | O |
| F6-23 | A1 | S | C-B30 | O | F6-24 | A1 | S | C-B32 | O |
| F6-25 | A1 | S | C-B42 | O | F6-26 | A1 | S | C-B54 | O |
| F6-27 | A1 | S | C-B70 | O | F6-28 | A1 | S | C-B72 | O |
| F6-29 | A1 | S | C-B73 | O | F6-30 | A1 | S | C-B74 | O |
| F6-31 | A1 | S | C-B108 | O | F6-32 | A1 | S | C-B124 | O |
| F6-33 | A1 | Se | C-B1 | O | F6-34 | A1 | Se | C-B6 | O |
| F6-35 | A1 | Se | C-B13 | O | F6-36 | A1 | Se | C-B18 | O |
| F6-37 | A1 | Se | C-B25 | O | F6-38 | A1 | Se | C-B27 | O |
| F6-39 | A1 | Se | C-B30 | O | F6-40 | A1 | Se | C-B32 | O |
| F6-41 | A1 | Se | C-B42 | O | F6-42 | A1 | Se | C-B54 | O |
| F6-43 | A1 | Se | C-B70 | O | F6-44 | A1 | Se | C-B72 | O |
| F6-45 | A1 | Se | C-B73 | O | F6-46 | A1 | Se | C-B74 | O |
| F6-47 | A1 | Se | C-B108 | O | F6-48 | A1 | Se | C-B124 | O |
| F6-49 | A1 | O | C-B1 | S | F6-50 | A1 | O | C-B6 | S |
| F6-51 | A1 | O | C-B13 | S | F6-52 | A1 | O | C-B18 | S |
| F6-53 | A1 | O | C-B25 | S | F6-54 | A1 | O | C-B27 | S |

-continued

| Compound No. | Y | W | $X_2 = X_L$ | $W_L$ | Compound No. | Y | W | $X_2 = X_L$ | $W_L$ |
|---|---|---|---|---|---|---|---|---|---|
| F6-55 | A1 | O | C-B30 | S | F6-56 | A1 | O | C-B32 | S |
| F6-57 | A1 | O | C-B42 | S | F6-58 | A1 | O | C-B54 | S |
| F6-59 | A1 | O | C-B70 | S | F6-60 | A1 | O | C-B72 | S |
| F6-61 | A1 | O | C-B73 | S | F6-62 | A1 | O | C-B74 | S |
| F6-63 | A1 | O | C-B108 | S | F6-64 | A1 | O | C-B124 | S |
| F6-65 | A1 | O | C-B1 | Se | F6-66 | A1 | O | C-B6 | Se |
| F6-67 | A1 | O | C-B13 | Se | F6-68 | A1 | O | C-B18 | Se |
| F6-69 | A1 | O | C-B25 | Se | F6-70 | A1 | O | C-B27 | Se |
| F6-71 | A1 | O | C-B30 | Se | F6-72 | A1 | O | C-B32 | Se |
| F6-73 | A1 | O | C-B42 | Se | F6-74 | A1 | O | C-B54 | Se |
| F6-75 | A1 | O | C-B70 | Se | F6-76 | A1 | O | C-B72 | Se |
| F6-77 | A1 | O | C-B73 | Se | F6-78 | A1 | O | C-B74 | Se |
| F6-79 | A1 | O | C-B108 | Se | F6-80 | A1 | O | C-B124 | Se |
| F6-81 | A2 | O | C-B1 | O | F6-82 | A2 | O | C-B6 | O |
| F6-83 | A2 | O | C-B13 | O | F6-84 | A2 | O | C-B18 | O |
| F6-85 | A2 | O | C-B25 | O | F6-86 | A2 | O | C-B27 | O |
| F6-87 | A2 | O | C-B30 | O | F6-88 | A2 | O | C-B32 | O |
| F6-89 | A2 | O | C-B42 | O | F6-90 | A2 | O | C-B54 | O |
| F6-91 | A2 | O | C-B70 | O | F6-92 | A2 | O | C-B72 | O |
| F6-93 | A2 | O | C-B73 | O | F6-94 | A2 | O | C-B74 | O |
| F6-95 | A2 | O | C-B108 | O | F6-96 | A2 | O | C-B124 | O; |

wherein Compound F7-1 to Compound F7-96 each have a structure represented by Formula F7':

F7'

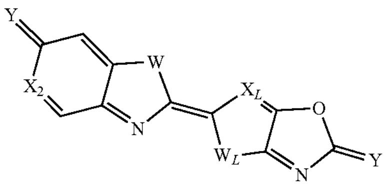

in Formula F7', two Y are the same, $X_2$ and $X_L$ are the same, and Y, $X_2$, $X_L$, W and $W_L$ are selected from atoms or groups in the following table, respectively:

| Compound No. | Y | W | $X_2 = X_L$ | $W_L$ | Compound No. | Y | W | $X_2 = X_L$ | $W_L$ |
|---|---|---|---|---|---|---|---|---|---|
| F7-1 | A1 | O | C-B1 | O | F7-2 | A1 | O | C-B6 | O |
| F7-3 | A1 | O | C-B13 | O | F7-4 | A1 | O | C-B18 | O |
| F7-5 | A1 | O | C-B25 | O | F7-6 | A1 | O | C-B27 | O |
| F7-7 | A1 | O | C-B30 | O | F7-8 | A1 | O | C-B32 | O |
| F7-9 | A1 | O | C-B42 | O | F7-10 | A1 | O | C-B54 | O |
| F7-11 | A1 | O | C-B70 | O | F7-12 | A1 | O | C-B72 | O |
| F7-13 | A1 | O | C-B73 | O | F7-14 | A1 | O | C-B74 | O |
| F7-15 | A1 | O | C-B108 | O | F7-16 | A1 | O | C-B124 | O |
| F7-17 | A1 | S | C-B1 | O | F7-18 | A1 | S | C-B6 | O |
| F7-19 | A1 | S | C-B13 | O | F7-20 | A1 | S | C-B18 | O |
| F7-21 | A1 | S | C-B25 | O | F7-22 | A1 | S | C-B27 | O |
| F7-23 | A1 | S | C-B30 | O | F7-24 | A1 | S | C-B32 | O |
| F7-25 | A1 | S | C-B42 | O | F7-26 | A1 | S | C-B54 | O |
| F7-27 | A1 | S | C-B70 | O | F7-28 | A1 | S | C-B72 | O |
| F7-29 | A1 | S | C-B73 | O | F7-30 | A1 | S | C-B74 | O |
| F7-31 | A1 | S | C-B108 | O | F7-32 | A1 | S | C-B124 | O |
| F7-33 | A1 | Se | C-B1 | O | F7-34 | A1 | Se | C-B6 | O |
| F7-35 | A1 | Se | C-B13 | O | F7-36 | A1 | Se | C-B18 | O |
| F7-37 | A1 | Se | C-B25 | O | F7-38 | A1 | Se | C-B27 | O |
| F7-39 | A1 | Se | C-B30 | O | F7-40 | A1 | Se | C-B32 | O |
| F7-41 | A1 | Se | C-B42 | O | F7-42 | A1 | Se | C-B54 | O |
| F7-43 | A1 | Se | C-B70 | O | F7-44 | A1 | Se | C-B72 | O |
| F7-45 | A1 | Se | C-B73 | O | F7-46 | A1 | Se | C-B74 | O |
| F7-47 | A1 | Se | C-B108 | O | F7-48 | A1 | Se | C-B124 | O |
| F7-49 | A1 | O | C-B1 | S | F7-50 | A1 | O | C-B6 | S |
| F7-51 | A1 | O | C-B13 | S | F7-52 | A1 | O | C-B18 | S |
| F7-53 | A1 | O | C-B25 | S | F7-54 | A1 | O | C-B27 | S |
| F7-55 | A1 | O | C-B30 | S | F7-56 | A1 | O | C-B32 | S |
| F7-57 | A1 | O | C-B42 | S | F7-58 | A1 | O | C-B54 | S |
| F7-59 | A1 | O | C-B70 | S | F7-60 | A1 | O | C-B72 | S |
| F7-61 | A1 | O | C-B73 | S | F7-62 | A1 | O | C-B74 | S |
| F7-63 | A1 | O | C-B108 | S | F7-64 | A1 | O | C-B124 | S |
| F7-65 | A1 | O | C-B1 | Se | F7-66 | A1 | O | C-B6 | Se |
| F7-67 | A1 | O | C-B13 | Se | F7-68 | A1 | O | C-B18 | Se |
| F7-69 | A1 | O | C-B25 | Se | F7-70 | A1 | O | C-B27 | Se |
| F7-71 | A1 | O | C-B30 | Se | F7-72 | A1 | O | C-B32 | Se |
| F7-73 | A1 | O | C-B42 | Se | F7-74 | A1 | O | C-B54 | Se |
| F7-75 | A1 | O | C-B70 | Se | F7-76 | A1 | O | C-B72 | Se |
| F7-77 | A1 | O | C-B73 | Se | F7-78 | A1 | O | C-B74 | Se |
| F7-79 | A1 | O | C-B108 | Se | F7-80 | A1 | O | C-B124 | Se |
| F7-81 | A2 | O | C-B1 | O | F7-82 | A2 | O | C-B6 | O |
| F7-83 | A2 | O | C-B13 | O | F7-84 | A2 | O | C-B18 | O |
| F7-85 | A2 | O | C-B25 | O | F7-86 | A2 | O | C-B27 | O |
| F7-87 | A2 | O | C-B30 | O | F7-88 | A2 | O | C-B32 | O |
| F7-89 | A2 | O | C-B42 | O | F7-90 | A2 | O | C-B54 | O |
| F7-91 | A2 | O | C-B70 | O | F7-92 | A2 | O | C-B72 | O |
| F7-93 | A2 | O | C-B73 | O | F7-94 | A2 | O | C-B74 | O |
| F7-95 | A2 | O | C-B108 | O | F7-96 | A2 | O | C-B124 | O. |

17. A compound combination, comprising the compound of claim 1.

18. An electroluminescent device, comprising:

an anode, a cathode and an organic layer disposed between the anode and the cathode, wherein the organic layer comprises the compound of claim 1.

19. The electroluminescent device according to claim 18, wherein the organic layer is a hole injection layer or a hole transporting layer, and the hole injection layer or the hole transporting layer is formed by the compound alone.

20. The electroluminescent device according to claim 18, wherein the organic layer is a hole injection layer or a hole transporting layer, wherein the hole injection layer or the hole transporting layer further comprises at least one hole transporting material; wherein a molar doping ratio of the compound to the hole transporting material is 10000:1 to 1:10000.

21. The electroluminescent device according to claim 20, wherein the hole transporting material comprises a compound having a triarylamine unit, a spirobifluorene compound, a pentacene compound, an oligothiophene compound, an oligomeric phenyl compound, an oligomeric phenylene vinyl compound, an oligofluorene compound, a porphyrin complex or a metallic phthalocyanine complex.

22. The electroluminescent device according to claim 18, wherein the electroluminescent device comprises at least two emissive units and the organic layer is a charge generation layer and disposed between the at least two emissive units, wherein the charge generation layer comprises a p-type charge generation layer and an n-type charge generation layer.

23. The electroluminescent device according to claim 22, wherein the charge generation layer further comprises a buffer layer disposed between the p-type charge generation layer and the n-type charge generation layer, and the buffer layer comprises the compound.

* * * * *